United States Patent
Shtil et al.

(10) Patent No.: US 6,171,786 B1
(45) Date of Patent: Jan. 9, 2001

(54) METHODS FOR PREVENTING MULTIDRUG RESISTANCE IN CANCER CELLS

(75) Inventors: Alexander A. Shtil, Chicago; Igor B. Roninson, Wilmette, both of IL (US)

(73) Assignee: Board of Trustees of University of Illinois, Urbana, IL (US)

( * ) Notice: Under 35 U.S.C. 154(b), the term of this patent shall be extended for 0 days.

(21) Appl. No.: 08/659,877

(22) Filed: Jun. 7, 1996

Related U.S. Application Data

(63) Continuation-in-part of application No. PCT/US96/00422, filed on Jan. 10, 1996, which is a continuation-in-part of application No. 08/370,724, filed on Jan. 10, 1995, which is a continuation-in-part of application No. 07/947,659, filed on Sep. 18, 1992, now abandoned.

(51) Int. Cl.[7] ........................................... C12Q 1/68
(52) U.S. Cl. .................. 435/6; 514/44; 514/283; 424/145.1
(58) Field of Search .................. 514/44, 283; 424/154.1; 435/6

(56) References Cited

FOREIGN PATENT DOCUMENTS

| 564409 | 10/1993 | (EP) . |
|---|---|---|
| WO 94/06938 | 3/1994 | (WO) . |
| WO9406938 | 3/1994 | (WO) . |

OTHER PUBLICATIONS

Anderson et al., "Enhancement of Merocyanine 540–mediated Phototherapy by Salicylate," *Cancer Res.* 53:806–809 (1993).
Angel et al., 1987, "Phorbol Ester–inducible Genes Contain a Common Cis Element Recognized by a TPA Modulated Trans–Acting Factor," *Cell* 49:729–739.
Aquino et al., 1990, "Enhanced Ca$^{2+}$–dependent Proteolysis correlated with Adriamycin–resistant HL–60 cells," *Cancer Commun.* 2:243–247.
Arceci et al., 1990, "Multidrug resistance gene expression is controlled by steroid hormones in the secretory epithelium of the uterus," *Mol. Repro. Dev.* 25:101–109.
Bates et al., 1989, "Expression of a Drug Resistance Gene in Human Neuroblastoma Cell Lines: Modulation by Retinoic Acid–induced Differentiation," *Mol. Cell. Biol.* 9:4337–4344.
Berdel et al.,1988, "Phase I studies of the thioether phospholipid analog ilmofosine in cancer patients," *Proc. Amer. Cancer. Res.* 29:Abs. 2050.
Bishop et al., 1990, "Inhibition of protein kinase C by the tyrosine kinase inhibitor erbstatin," *Biochem. Pharmacol.* 40:2129–2135.
Budworth, et al., 1994, "Multidrug–resistant MCF–7 breast carcinoma cells are cross–resistant towards the protein kinase C (PKC) inhibitor RO 31–8220, but not towards staurosporine (Meeting abstract)," *Br. J. Cancer* 69(Suppl. 21):17.

Bunn et al., "Tyrosine Hydorxylase Phosphorylation in Bovine Adrenal Chromaffin Cells: The Role of Intracellular Ca$^{2+}$ in the Histamine H$_1$ Receptor–Stimulated Phosphorylation of Ser$^8$, Ser$^{19}$, Ser$^{31}$, and Ser$^{40}$," *J. Neurochem.* 64:1370–1378 (1995).
Chakrabarti et al., "T Cell Receptor–Mediated Ca$^{2+}$ Signaling: Release and Influx Are Independent Events Linked to Different Ca$^{2+}$ Entry Pathways in the Plasma Membrane," *J. Cell. Biochem.* 58:344–359.
Chambers et al., 1990, "Correlation of protein kinase C translocation, P–glycoprotein phosphorylation and reduced drug accumulation in multidrug resistant human KB cells," *Biochem. Biophys. Res. Commun.* 169:253–259.
Chambers et al., 1990, "Protein Kinase C Phosphorylates P–glycoprotein in Multidurg Resistant Human KB Carcinoma Cells," *J. Biol. Chem.* 265:7679–7686.
Chan et al., 1990, "Immunohistochemical Detection of P–Glycoprotein: Prognostic Correlation in Soft Tissue Sarcoma of Childhood," *J. Clin. Oncol.* 8:689–704.
Chan et al., 1991, "P–Glycoprotein Expression as a Predictor of the Outcome of Terapy for Nueroblstoma," *N. Eng. J. Med.* 325:1608–1614.

(List continued on next page.)

*Primary Examiner*—Scott W. Houtteman
(74) *Attorney, Agent, or Firm*—McDonnell Boehnen Hulbert & Berghoff

(57) ABSTRACT

This invention is directed to methods for preventing the emergence of multidrug resistance in tumor cells during cancer chemotherapy. In particular, it relates to the use of cytoplasmic calcium antagonists and calmodulin inhibitors, phosphoinositol-dependent phospholipase C inhibitors, and substances that inhibit activation of the transcription factor NF-κB to prevent the induction of expression of the multidrug resistance gene (MDR1) encoding P-glycoprotein by chemotherapeutic drugs. MDR1 expression, which results in tumor cell resistance to subsequent treatment with certain chemotherapeutic drugs, is shown herein to be induced in response to treatment with various cytotoxic agents, including such agents that are or are not substrates for P-glycoprotein-mediated efflux from cancer cells. Cytoplasmic calcium antagonists and calmodulin inhibitors, phosphoinositol-dependent phospholipase C inhibitors, and substances that inhibit activation of the transcription factor NF-κB are shown herein to suppress this cellular response. The invention also provides methods for identifying cytoplasmic calcium antagonists and calmodulin inhibitors, phosphoinositol-dependent phospholipase C inhibitors, and substances that inhibit activation of the transcription factor NF-κB that suppress induction of MDR1 gene expression by cytotoxic drugs. Thus, the invention provides useful methods and reagents for preventing the emergence of multidrug resistance in tumor cells treated with cytotoxic and chemotherapeutic drugs in cancer patients undergoing chemotherapy, when cytoplasmic calcium antagonists and calmodulin inhibitors, phosphoinositol-dependent phospholipase C inhibitors, and substances that inhibit activation of the transcription factor NF-κB are administered prior to or simultaneously with cytotoxic drug treatment in such individuals.

25 Claims, 33 Drawing Sheets

OTHER PUBLICATIONS

Chaudhary and Roninson, 1991, "Expression and Activity of P–plycoprotein, a Multidrug efflux pump, in Human Hematopoietic Stem Cells," *Cell* 66:85–94.

Chauhan et al., 1990, "Regulation of protein kinase C by the inositide shuttle: neomycin," *FASEB J.* 4:A1779.

Chin et al., 1990, "Heat Shock and Arsenite Increase Expression of the Multidrug Resistance (MDR1) Gene in Human Renal Carcinoma Cells," *J. Biol. Chem.* 265:221–226.

Chin et al., 1990, "Regulation of mdr RNA Levels in Response to Cytotoxic Drugs in Rodent Cells," *Cell Growth Diff.* 1:361–365.

Choi et al., 1991, "Multidrug resistance after retroviral transfer of the human MDR1 gene correlates with P–glycoprotein density in the plasma membrane and is not affected by cytotoxic selection," *Proc. Natl. Acad. Sci. USA* 88:7386–7390.

Cockroft et al., "Two G–Proteins Act in Series to Control Stimulus–Secretion Coupling in Mast Cells: Use of Neomycin to Distinguish between G–Proteins Controlling Polyphosphoinositide Phosphodiesterase and Exocytosis," *J. Cell. Biol.* 105:2745–2758 (1987).

Cordon–Cardo et al., 1990, "Expression of Multidrug Resistance Gene Product (P–Glycoprotein) in Human Normal and Tumor Tissues," *J. Histochem. Cytochem.* 38:1277–1287.

Dalton et al., 1989, "Drug–Resistance in Multiple Myeloma and Non–Hodgkin's Lymphoma: Detection of P–Glycoprotein and Potential Circumvention by Addition of Verapamil to Chemotherapy," *J. Clin. Oncol.* 7:415–424.

Fairchild et al., 1987, "Carcinogen–induced mdr overexpression is associated with xenobiotic resistance in rat preneoplastic liver nodules and hepatocellular carcinomas " *Proc. Natl. Acad. Sci. USA* 84:7701–7705.

Ferguson and Cheng, 1987, "Transient Protection of Cultured Human Cells against Antitumor Agents by 12–O–Tetradecanolyphorbol–13–acetate," *Cancer Res.* 47: 433–441.

Fine et al., 1988, "Phorbol esters induce multidrug resistance in human breast cancer cells," *Proc. Natl. Acad. Sci. USA* 85:582–586.

Ford and Hait, 1990, "Pharmacology of drugs that alter multidrug resistance in cancer," *Pharmacol. Rev.* 42:155–199.

Ford et al., 1990, "Cellular and Biochemical Characterization of Thioxanthenes for Reversal of Multidrug Resistance in Human and Murine Cell Lines," *Cancer Res.* 50:1748–1756.

Gandhi et al., "Platelet–activating factor–mediated synthesis of prostablandins in rat Kupffer cells," *Biochim. Biophys. Acta* 1136:68–74 (1992).

Geng et al., "Increased Intracellular $Ca^{2+}$ Selectively Suppresses IL–1–induced NO Production by Reducing iNOS mRNA Stability," *J. Cell Biol.* 129:1651–1657 (1995).

Goldstein et al., 1989, "Expression of a Multidrug Resistance gene in Human Cancers," *J. Natl. Cancer Inst.* 81:116–124.

Gollapudi et al., 1992, "Effect of Calphostin, A Specific Inhibitor of Protein Kinase C (PKC), on Daunorubicin Transport and Cytotoxicity in Multidrug–Resistant (MDR) 388/ADR and HL60/AR Cells (Meeting Abstract)," *Proc. Annu. Meet. Am. Assoc. Cancer Res.* 33:A2734.

Grant et al., 1994, "Overexpression of Multidrug Resistance–associated Protein (MRP) Increases to Natural Product Drugs," *Cancer Res.* 54:357–361.

Grunicke et al., 1989, "The Phospholipid– and calcium–dependent protein kinase C as a target of tumor chemotherapy," *Adv. Enzyme Regul.* 28:201–216.

Gschwendt et al., 1984, "Calcium and phospholipid–dependent protein kinase activity in mouse epidermis cytosol: Stimulation by complete and incomplete tumor promoters and inhibition by various compounds," *Biochem. Biophys. Res. Commun.* 124:63.

Gupta et al., 1994, "Effect of calphostin C (PKC inhibitor) on daunorubicin resistance in P388–ADR and HL60–AR cells: Reversal of drug resistance possibly via P–glycoprotein," *Cancer Letters* 76(2–3):139–145.

Hamada et al., 1987, "Phosphorylation of the M 170,000 to 180,000 Glycoprotein to Multidrug–resistant Tumor Cells: Effects of Verapamil, Trifluoperazine, and Phorbol Ester," *Cancer Res.* 47:2860–2865.

Heemskerek et al., "Indirect regulation of $Ca^{2+}$ entry by cAMP–dependent and cGMP–dependent protein kinases and phospholipase C in rat platelets," *Eur. J. Biochem.* 223:543–551 (1994).

Herrmann et al., 1987, "Phase 1 Trial of the Thioether Phospholipid Analogue BM 41.440 in Cancer Patients," *Lipids* 22:962–966.

Hidaka et al., 1984, "Isoquinolinesulfonamides, Novel and Potent Inhibitors of Cyclic Nucleotide Dependent Protein Kinase and Protein Kinase C," *Biochemistry* 23:5036–5041.

Hsu et al., 1990, "Structural Analysis of the Mouse mdr1a (P–glycoprotein) Promoter Reveals the Basis for Differential transcription Heterogeneity in Multidrug resistant J774.2 Cells," *Mol. Cell Biol.* 10:3596–3606.

Ikeguchi et al., 1991, "Structural and Functional Analyses of the Promoter of the Murine Multidrug Resistance Gene mdr3/mdr1a Reveal a Negative Element Containing the Ap–1 Binding Site," *DNA Cell Biol.* 10:639–649.

Imoto et al., 1987, "Antitumor activity of erbstatin, a tyrosine protein kinase inhibitor," *Japanese J. Cancer Res.* 78:329–332.

Kaina et al., 1989, "An update of the mammalian UV response: gene regulation and induction of a protective function," in Lambert and Laval (eds.), *DNA Repair Mechanisms and Their Biological Implications in Mammalian Cells*, Plenum Press, New York.

Kantengwa and Polla, 1991, "Flavinoids, but not protein kinase C inhibitors, prevent stress protein synthesis during erythrophagocytosis," *Biochem. Biophys. Res. Commun.* 180:308–314.

Kharbanda et al., 1991, Camptothecin and Its Derivatives Induce Expression of the c–jun Protooncogene in Human Myeloid Leukemia Cells, *Cancer Res.* 51:6636–6642.

Kharbanda et al., 1991, "Regulation of c–jun Gene Expression in HL–60 Leukemia Cells by 1–β–D–Arabinofuranosylcytosine. Potential Involvement of a Protein Kinase C Dependent Mechanism," *Biochemistry* 30:7947–7952.

Kioka et al., 1992, "Quercetin, a bioflavinoid, inhibits the increase of human multidrug resistance gene (MDR1) expression caused by arsenite," *FEBS Lett.* 301:307–309.

Kohno et al., 1989, "The Direct Activation of Human Multidrug Resistance Gene (MDR1) by Anticancer Agents," *Biochem. Biophys. Res. Commun.* 165:1415–1421.

Kopp et al., "Inhibition of NF–κB by Sodium Salicylate and Aspirin," *Science* 265:956–959 (1994).

Krug and Berger, 1987, "First–strand cDNA synthesis primer with oligo(dl)," *Meth. Enzymol.* 152:316–324.

Laredo et al., 1993, "Implication of protein kinase C in the resistance of myeloid leukemia cells to daunorubicin (Meeting abstract)," *Proc. Annu. Meet. Am. Assoc. Cancer Res.* 34:A1905.

Laredo et al., 1994, "Effect of the protein kinase C inhibitor staurosporine on chemosensitivity to daunorubicin of normal and leukemic fresh myeloid cells," *Blood* 84(1):229–237.

Lee et al., 1987, "Purified Transcription Factor AP–1 Interacts with TPA–Inducible Enhancer Elements," *Cell* 49:741–752.

Licht et al., 1991, "Induction of multiple–drug resistance during anti–neoplastic chemotherapy in vitro," *Int. J. Cancer* 49:630–637.

Ma et al., Mar. 25, 1991, *J. Biol. Chem.* 266(9):5593–5599.

Marnett, "Aspirin and the Potential Role of Prostaglandins in Colon Cancer," *Cancer Res.* 52:5575–5589 (1992).

Mechetner and Roninson, 1992, "Efficient inhibition of P–glycoprotein–mediated multidrug resistance with a monoclonal antibody," *Proc. Natl. Acad. Sci. USA* 89: 5824–5828.

Meyer et al., 1989, "A derivative of staurosporine (CGP 41 251) shows selectivity for protein kinase C inhibition and in vitro anti–proliferative as well as in vivo anti–tumor activity," *Int. J. Cancer* 43:851–856.

Mickely et al., 1989, "Modulation of the Expression of a Multidrug Resistance Gene (mdr1–P–glycoprotein) by Differentiating Agents," *J. Biol. Chem.* 264:18031–18040.

Musto et al., 1991, "High Risk of early resistance relapse for leukamic patients with presence of multidrug resistance associated P–glycoprotein positive cells in complete remission," *Brit. J. Haematol.* 77:50–53.

Neyfakh et al., 1989, "Multidrug–Resistance Phenotype of a Subpopulation of T–Lymphocytes without Drug Selection," *Exp. Cell Res.* 185:496–505.

Noonan and Roninson, 1991, "Quantitative Estimation of MDR1 mRNA Levels by Polymerase Chain Reaction," pp. 319–333 in Roninson (ed.), *Molecular and Cellular Biology of Multidrug Resistance in Tumor Cells*, Plenum Press, New York.

Noonan et al., 1990, "Quantitative analysis of MDR1 (multidrug resistance) gene expression in human tumors by polymerase chain reaction," *Proc. Natl. Acad. Sci. USA* 87:7160–7164.

O'Brian et al., 1989, "Level of protein kinase C activity correlates directly with resistance to adriamycin in murine fibrosarcoma cells," *FEBS Lett.* 246:78–82.

O'Brian et al., "Transient Enhancement of Multidrug Resistance by the Bile Acid Deoxycholate in Murine Fibrosarcoma Cells In Vitro," Mar. 1, 1991, *Biochem. Pharmacol.* 41(5):797–806.

Palayoor et al., 1987, "Inhibition of protein kinase C by antineoplastic agents: Implications for drug resistance," *Biochem. Biophys. Res. Commun.* 148:718–725.

Papathanasiou and Fornace, 1991, "DNA–damaging inducible genes," pp. 13–36 in Ozols (ed.), *Molecular and Clinical Advances in Anticancer Drug Resistance*, Kluwer Academic Publishers, Boston, MA.

Pastan and Gottesman, 1991, "Multridrug Resistance," *Annu. Rev. Med.* 42:277–286.

Pauwels et al., 1988, "Rapid and automated tetrazolium––based colorimetric assay for the detection of anti–HIV compounds," *J. Virol. Meth.* 20:309–321.

Pelosin et al., 1990, "Differential inhibition of protein kinase C subtypes," *Biochem. Biophys. Res. Commun.* 169:1040–1048.

Peppel and Baglioni, 1990, "A simple and fast method to extract RNA from tissue culture cells," *BioTechniques* 9:711–713.

Pinedo et al., 1992, "Suramin Awakes?," *J. Clin. Oncol.* 10:875–877.

Posada et al., 1989, "Human Multidrug Resistant KB Cells Overexpress Protein Kinase C: Involvement in Drug Resistance," *Cancer Commun.* 1:285–292.

Posada et al., 1989, "Protein Kinase C in Adriamycin Action and Resistance in Mouse Sarcoma 180 Cells," *Cancer Res.* 49:6634–6639.

Powis and Kozikowski, 1991, "Growth Factor and Oncogene Signaling Pathways as Targets for Rational Anticancer Drug Development," *Clin. Biochem.* 24:385–397.

Rao et al., "Chemoprevention of Colon Carcinogenesis by Sulindac, a Nonsteroidal Anti–inflammatory Agent," *Cancer Res.* 55:1464–1472 (1995).

Roninson (ed.), 1991, *Molecular and Cellular Biology of Multidrug Resistance in Tumor Cells*, Plenum Press, New York.

Rüegg and Burgess, 1989, "Staurosporine, K–252 and UCN–01: potent but nonspecific inhibitors of protein kinases," *Trends Pharmac. Sci.* 10:218–220.

Sampson et al., 1993, "Staurosporine Reduces P–Glycoprotein Expression and Modulates Multidrug Resistance," *Cancer Letters* 68(1):7–14.

Sato et al., 1990, "Staurosporine: A potent inhibitor of C–kinase, enhances drug accumulation in multidrug resistant cells," *Biochem. Biophys. Res. Commun.* 173:1252–1257.

Schinkel and Borst, 1991, "Multidrug resistance mediated by P–glycoprotein," *Seminars in Cancer Biology* 2:213–226.

Schurig et al., 1990, "Experimental antitumor activity of BMY–27557, a new antitumor agent," *Proc. Amer. Assoc. Cancer Res.* 31:Abs. 2469.

Siebenlist et al., "Structure, Regulation and Function of NF–κB," *Annu. Rev. Cell. Biol.* 10:405–455 (1994).

Sikic, 1993, "Modulation of Multidrug Resistance: At the Threshold", *J. Clin. Oncol.* 11:1629–1635.

Silver et al., "Modulation of Vascular and Cardiac Contractile Protein Regulatory Mechanisms by Calmodulin Inhibitors and Related Compounds," *Biochem. Pharmacol.* 35:2545–2551 (1986).

Takahashi et al., 1987, "UCN–01, a selective inhibitor of protein kinase C from Streptomyces," *J. Antibiot.* 40:1782–1784.

Tanimura et al., 1992, "The human multidrug resistance 1 promoter has an element that responds to serum starvation," *Biochem. Biophys. Commun.* 183:917–924.

Teeter et al., 1991, "Analysis of the Chinese Hamster P–Glycoprotein/Multidrug Resistance Gene pgp1 Reveals that the Ap–1 Site is Essential for Full Promoter Acitivity," *Cell Growth Diff.* 2:429–437.

Thiebaut et al., 1987, "Cellular localization of the multidrug–resistance gene product P–glycoprotein in normal human tissues," *Proc. Natl. Acad. Sci. USA* 84:7735–7738.

Thorgeirsson et al., 1987, "Expression of the Multidrug Resistant Gene in Hepatocarcinogenesis and Regenerating Rat Liver," *Science* 236:1120–1122.

Toi et al., 1990, "Antineoplastic effect of erbstatin on human mammary and esophageal tumors in athymic nude mice," *Eur. J. Cancer* 26:722–724.

Ueda et al., 1987, "The Human Multidrug Resistance (mdr1) Gene," *J. Biol. Chem.* 262:505–508.

Umezawa and Imoto, 1991, "Use of Erbstsatin as Protein––Tyrosin Kinase Inhibitor," *Meth. Enzymol.* 201:379–385.

Unger et al., 1990, "Hexadecylphosphocholine in the topical treatment of skin metastases in breast cancer patients," *Cancer Treat. Rev.* 17:243–246.

Vogler et al., 1991, "A phase I trial of bone marrow purging in acute leukemia with alkyl–lysophospholipid (ALP)," *Exp. Hematol.* 99:557 Abs.

Wiegmann et al., "Functional Dichotomy of Neutral and Acidic Sphingon yelinases in Tumor Necrosis Factor Signaling," *Cell* 78:1005–1015 (1994).

Wiegmann et al., "Functional Dichotomy of Neutral and Acidic Sphingonyelinases in Tumor Necrosis Factor Signaling," *Cell* 78:1005–1015 (1994).

Anderson et al., "Enhancement of Merocyanine 540–mediated Phototherapy by Salicylate," *Cancer Res.* 53:806–809 (1993).

Angel et al., 1987, "Phorbol Ester–inducible Genes Contain a Common *Cis* Element Recognized by a TPA Modulated *Trans*–Acting Factor," *Cell* 49:729–739.

Aquino et al., 1990, "Enhanced $Ca^{2+}$–dependent Proteolysis correlated with Adriamycin–resistant HL–60 cells," *Cancer Commun.* 2:243–247.

Arceci et al., 1990, "Multidrug resistance gene expression is controlled by steroid hormones in the secretory epithelium of the uterus," *Mol. Repro. Dev.* 25:101–109.

Bates et al., 1989, "Expression of a Drug Resistance Gene in Human Neuroblastoma Cell Lines: Modulation by Retinoic Acid–induced Differentiation," *Mol. Cell, Biol.* 9:4337–4344.

Berdel et al., 1988, "Phase I studies of the thioether phospholipid analog ilmofosine in cancer patients," *Proc. Amer. Cancer. Res.* 29:Abs. 2050.

Bishop et al., 1990, "Inhibition of protein kinase C by the tyrosine kinase inhibitor erbstatin," *Biochem. Pharmacol.* 40:2129–2135.

Budworth, et al., 1994, "Multidrug–resistant MCF–7 breast carcinoma cells are cross–resistant towards the protein kinase C (PKC) inhibitor RO 31–8220, but not towards staurosporine (Meeting abstract)," *Br. J. Cancer* 69(Suppl. 21):17.

Bunn et al., "Tyrosine Hydorxylase Phosphorylation in Bovine Adrenal Chromaffin Cells: The Role of Intracellular $Ca^{2+}$ in the Histamine $H_1$ Receptor–Stimulated Phosphorylation of $Ser^8$, $Ser^{19}$, $Ser^{31}$, and $Ser^{40}$," *J. Neurochem.* 64:1370–1378 (1995).

Chakrabarti et al., "T Cell Receptor–Mediated $Ca^{2+}$ Signaling: Release and Influx Are Independent Events Linked to Different $Ca^{2+}$ Entry Pathways in the Plasma Membrame," *J. Cell. Biochem.* 58:344–359.

Chambers et al., 1990, "Correlation of protein kinase C translocation, P–glycoprotein phosphorylation and reduced drug accumulation in multidrug resistant human KB cells," *Biochem. Biophys. Res. Commun.* 169:253–259.

Chambers et al., 1990, "Protein Kinase C Phosphorylates P–glycoprotein in Multidrug Resistant Human KB Carcinoma Cells," *J. Biol. Chem.* 265:7679–7686.

Chan et al., 1990, "Immunohistochemical Detection of P–Glycoprotein: Prognostic Correlation in Soft Tissue Sarcoma of Childhood," *J. Clin. Oncol.* 8:689–704.

Chan et al., 1991, "P–Glycoprotein Expression as a Predietor of the Outcome of Terapy for Neuroblstoma," *N. Eng. J. Med.* 325:1608–1614.

Chaudhary and Roninson, 1991, "Expression and Activity of P–plycoprotein, a Multidrug efflux pump, in Human Hematopoietic Stem Cells," *Cell* 66:85–94.

Chauhan et al., 1990, "Regulation of protein kinase C by the inositide shuttle: neomycin," *FASEB J.* 4:A1779.

Chin et al., 1990, "Heat Shock and Arsenite Increase Expression of the Multidrug Resistance (MDRI) Gene in Human Renal Carcinomna Cells," *J. Biol. Chem.* 265:221–226.

Chin et al., 1990, "Regulation of *mdr* RNA Levels in Response to Cytotoxic Drugs in Rodent Cells," *Cell Growth Diff.* 1:361–365.

Choi et al., 1991, "Multidrug resistance after retroviral transfer of the human *MDR1* gene correlates with P–glycoprotein density in the plasma membrane and is not affected by cytotoxic selection," *Proc. Natl. Acad. Sci. USA* 88:7386–7390.

Cockroft et al., "Two G–Proteins Act in Series to Control Stimulus–Secretion Coupling in Mast Cells: Use of Neomycin to Distinguish between G–Proteins Controlling Polyphosphoinositide Phosphodiesterase and Exocytosis," *J. Cell. Biol.* 105:2745–2758 (1987).

Cordon–Cardo et al., 1990, "Expression of Multidrug Resistance Gene Product (P–Glycoprotein) in Human Normal and Tumor Tissues," *J. Histochem. Cytochem.* 38:1277–1287.

Dalton et al., 1989, "Drug–Resistance in Multiple Myeloma and Non–Hodgkin's Lymphoma: Detection of P–Glycoprotein and Potential Circumvention by Addition of Verapamil to Chemotherapy," *J. Clin. Oncol.* 7:415–424.

Fairchild et al., 1987, "Carcinogen–induced *mdr* overexpression is associated with xenobiotic resistance in rat preneoplastic liver nodules and hepatocellular carcinomas," *Proc. Natl. Acad. Sci. USA* 84:7701–7705.

Ferguson and Cheng, 1987, "Transient Protection of Cultured Human Cells against Antitumor Agents by 12–O–Tetradecanolyphorbol–13–acetate," *Cancer Res.* 47:433–441.

Fine et al., 1988, "Phorbol esters induce mulitdrug resistance in human breast cancer cells," *Proc. Natl. Acad. Sci. USA* 85:582–586.

Ford and Hait, 1990, "Pharmacology of drugs that alter multidrug resistance in cancer," *Pharmacol. Rev.* 42:155–199.

Ford et al., 1990, "Cellular and Biochemical Characterization of Thioxanthenes for Reversal of Multidrug Resistance in Human and Murine Cell Lines," *Cancer Res.* 50:1748–1756.

Gandhi et al., "Platelet–activating factor–mediated synthesis of prostablandins in rat Kupffer cells," *Biochim. Biophys. Acta* 1136:68–74 (1992).

Geng et al., "Increased Intracellular $Ca^{2+}$ Selectively Suppresses IL–1–induced NO Production by Reducing iNOS mRNA Stability," *J. Cell Biol.* 129:1651–1657(1995).

Goldstein et al., 1989, "Expression of a Multidrug Resistance gene in Human Cancers," *J. Natl. Cancer Inst.* 81:116–124.

Gollapudi et al., 1992, "Effect of Calphostin, A Specific Inhibitor of Protein Kinase C (PKC), on Daunorubicin Transport and Cytotoxicity in Multidrug–Resistant (MDR) l'388/ADR and HL60/AR Cells (Meeting Abstract)," *Proc. Annu. Meet. Am. Assoc. Cancer Res.* 33:A2734.

Grant et al., 1994, "Overexpression of Multidrug Resistance–associated Protein (MRP) Increases to Natural Product Drugs," *Cancer Res.* 54:357–361.

Grunicke et al., 1989, "The Phospholipid–and calcium–dependent protein kinase C as a target of tumor chemotherapy," *Adv. Enzyme Regul.* 28:201–216.

Gschwendy et al., 1984, "Calcium and phospholipid–dependent protein kinase activity in mouse epidermis cytosol: Stimulation by complete and incomplete tumor promoters and inhibition by various compounds," *Biochem. Biophys. Res. Commun.* 124:63.

Gupta et al., 1994, "Effect of calphostin C (PKC inhibitor) on daunorubicin resistance in P388–ADR and HL60–AR cells: Reversal of drug resistance possibly via P–glycoprotein," *Cancer Res.* 47:2860–2865.

Hamada et al., 1987, "Phosphorylation of the M 170,000 to 180,000 Glycoprotein to Multidrug–resistant Tumor Cells: Effects of Verapamil, Trifluoperazine, and Phorbol Esters," *Cancer Res.* 47:2860–2865.

Heemskerek et al., "Indirect regulation of $Ca^{2+}$ entry by cAMP–dependent protein kinases and phospholipase C in rat platelets," *Eur. J. Biochem.* 223:543–551 (1994).

Herrmann et al., 1987, "Phase 1 Trial of the Thioether Phospholipid Analogue BM 41.440 in Cancer Patients," *Lipids* 22:962–966.

Hidaka et al., 1984, "Isoquinolinesulfonamides, Novel and Potent Inhibitors of Cyclic Nucleotide Dependent Protein Kinase and Protein Kinase C," *Biochemistry* 23:5036–5041.

Hsu et al., 1990, "Structuaral Analysis of the Mouse *mdr*1a (P–glycoprotein) Promoter Reveals the Basis for Differential transcription Heterogeneity in Multidrug resistant J774.2 Cells," *Mol. Cell Biol.* 10:3596–3606.

Ikeguchi et al., 1991, "Structural and Functional Analyses of the Promoter of the Murine Multidrug Resistance Gene *mdr3/mdr1a* Reveal a Negative Element Containing the Ap–1 Binding Site," *DNA Cell Biol.* 10:639–649.

Imoto et al., 1987, "Antitumor acitivity of erbstatin, a tyrosine protein kinase inhibitor," *Japanese J. Cancer Res.* 78:329–332.

Kaina et al., 1989, "An update of the mammalian UV response: gene regulation and induction of a protective function," *in* Lambert and Laval (eds.), *DNA Repair Mechanisms and Their Biological Implications in Mammalian Cells*, Plenum Press, New York.

Kantengwa and Polla, 1991, "Flavinoids, but not protein kinase C inhibitors, prevent stress protein synthesis during erythrophagocytosis," *Biochem. Biophys. Res. Commun.* 80:308–314.

Kharbanda et al., 1991, Camptothecin and Its Derivatives Induce Expression of the c–*jun* Protooncogene in Human Myeloid Leukemia Cells, *Cancer Res.* 51:6636–6642.

Kharbanda et al., 1991, "Regulation of c–jun Gene Expression in HL–60 Leukemia Cells by 1–β–D–Arabinofuranosylcytosinc. Potential Involvement of a Protein Kinase C Dependent Mechanism," *Biochemistry* 30:7947–7952.

Kioka et al., 1992, "Quercetin, a bioflavinoid, inhibits the increase of human multidrug resistance gene (*MDR1*) expression caused by arsenite," *FEBS Lett.* 301:307–309.

Kohno et al., 1989, "The Direct Activation of Human Multidrug Resistance Gene (MDR1) by Anticancer Agents," *Biochem. Biophys. Res. Commun.* 165:1415–1421.

Kopp et al., "Inhibition of NF–κB by Sodium Salicylate and Aspirin," *Science* 265:956–959 (1994).

Krug and Berger, 1987, "First–strand cDNA synthesis primer with oligo(dT)," *Meth, Enzymol.* 152:316–324.

Laredo et al., 1993, "Implication of protein kinase C in the resistance of myeloid leukemia cells to daunorubicin (Meeting abstract)," *Proc. Annu. Meet. Am. Assoc. Cancer Res.* 34:A1905.

Laredo et al., 1994, "Effect of the protein kinase C inhibitor staurosporine on chemosensitivity ot daunorubicin of normal and leukemic fresh myeloid cells," *Blood* 84(1):229–237.

Lee et al., 1987, "Purified Transcription Factor AP–1 Interacts with TPA–Inducible Enhancer Elements," *Cell* 49:741–752.

Licht et al., 1991, "Induction of multiple–drug resistance during anti–neoplastic chemotherapy *in vitro,*" *Int. J. Cancer* 49:630–637.

Ma et al., Mar. 25, 1991, *J. Biol. Chem.* 266(9):5593–5599.

Marnett, "Aspirin and the Potential Role of Prostaglandins in Colon Cancer," *Cancer Res.* 52:5575–5589 (1992).

Mechetner and Roninson, 1992, "Efficient inhibition of P–glycoprotein–mediated multidrug resistance with a monoclonal antibody," *Proc. Natl. Acad. Sci. USA* 89:5824–5828.

Meyer et al., 1989, "A derivative of staurosporine (CGP 41 251) shows selectivity for protein kinase C inhibition and *in vitro* anti–proliferative as well as *in vivo* anti–tumor activity," *Int. J. Cancer* 43:851–856.

Mickely et al., 1989, "Modulation of the Expression of a Multidrug Resistance Gene (*mdr*1–P–glycoprotein) by Differentiating Agents," *J. Biol. Chem.* 264:18031–18040.

Musto et al., 1991, "High Risk of early resistance relapse for leukemic patients with presence of multidrug resistance associated P–glycoprotein positive cells in complete remission," *Brit. J. Haematol.* 77:50–53.

Neyfakh et al., 1989, "Multidrug–Resistance Phenotype of a Subpopulation of T–Lymphocytes without Drug Selection," *Exp. Cell Res* 185:496–505

Noonan and Roninson, 1991, "Quantitative Estimation of MDR1 mRNA Levels by Polymerase Chain Reaction," pp. 319–333 *in* Roninson (ed.), *Molecular and Cellular Biology of Multidrug Resistance in Tumor Cells*, Plenum Press, New York.

Noonan et al., 1990, "Quantitative analysis of *MDR1* (multidrug resistance) gene expression in human tumors by polymerase chain reaction," *Proc. Natl. Acad. Sci. USA* 87:7160–7164.

O'Brian et al., 1989, "Level of protein kinase C activity correlates directly with resistance to adriamycin in murine fibrosarcoma cells," *FEBS Lett.* 246:78–82.

O'Brian et al., "Transient Enhancement of Multidrug Resistance by the Bile Acid Deoxycholate in Murine Fibrosarcoma Cells *In Vitro,*" Mar. 1, 1991, *Biochem. Pharmacol.* 41(5):797–806.

Palayoor et al., 1987, "Inhibition of protein kinase C by antineoplastic agents: Implications for drug resistance," *Biochem. Biophys. Res. Commun.* 148:718–725.

Papathanasiou and Fornace, 1991, "DNA–damaging inducible genes,"pp. 13–36 *in* Ozols (ed.), *Molecular and Clinical Advances in Anticancer Drug Resistance*, Kluwer Academic Publishers, Boston, MA.

Pastan and Gottesman, 1991, "Multridrug Resistance," *Annu. Rev. Med.* 42:277–286.

Pauwels et al., 1988, "Rapid and automated tetrazolium–based colorimetric assay for the detection of anti–HIV compounds," *J. Virol. Meth.* 20:309–321.

Pelosin et al., 1990, "Differential inhibition of protein kinase C subtypes," *Biochem. Biophys. Res. Commun.* 169:1040–1048.

Peppel and Baglioni, 1990, "A simple and fast method to extract RNA from tissue culture cells," *BioTechniques* 9:711–713.

Pinedo et al., 1992, "Suramin Awakes?," *J. Clin. Oncol.* 10:875–877.

Posada et al., 1989, "Human Multidrug Resistant KB Cells Overexpress Protein Kinase C: Involvement in Drug Resistance," *Cancer Commun.* 1:285–292.

Posada et al., 1989, "Protein Kinase C in Adriamycin Action and Resistance in Mouse Sarcoma 180 Cells," *Cancer Res.* 49:6634–6639.

Powis and Kozikowski, 1991, "Growth Factor and Oncogene Signaling Pathways as Targets for Rational Anticancer Drug Development," *Clin. Biochem.* 24:385–397.

Rao et al., "Chemoprevention of Colon Carcinogenesis by Sulindac, a Nonsteroidal Anti–inflammatory Agent," *Cancer Res.* 55:1464–1472 (1995).

Roninson (ed.), 1991, *Molecular and Cellular Biology of Multidrug Resistance in Tumor Cells*, Plenum Press, New York.

Rüegg and Burgess, 1989, "Staurosporine, K–252 and UCN–01: potent but nonspecific inhibitors of protein kinases," *Trends Pharmac. Sci.* 10:218–220.

Sampson et al., 1993, "Staurosporine Reduces P–Glycoprotein Expression and Modulates Multidrug Resistance," *Cancer Letters* 68(1):7–14.

Sato et al., 1990, "Staurosporine: A potent inhibitor of C–kinase, enhances drug accumulation in multidrug resistant cells," *Biochem. Biophys. Res. Commun.* 173:1252–1257.

Schinkel and Borst, 1991, "Multidrug resistance mediated by P–glycoprotein," *Seminars in Cancer Biology* 2:213–226.

Schurig et al., 1990, "Experimental antitumor activity of BMY–27557, a new antitumor agent," *Proc. Amer. Assoc. Cancer Res.* 31:Abs. 2469.

Siebenlist et al., "Modulation of Multidrug Resistance: At the Threshold", *J. Clin. Oncol.* 11:1629–1635.

Silver et al., "Modulation of Vascular and Cardiac Contractile Protein Regulatory Mechanisms by Calmodulin Inhibitors and Related Compounds," *Biochem. Pharmacol.* 35:2545–2551 (1986).

Takahashi et al., 1987, "UCN–01, a selective inhibitor of protein kinase C from *Streptomyces*," *J. Antibiot.* 40:1782–1784.

Tanimura et al., 1992, "The human multidrug resistance 1 promoter has an element that responds to serum starvation," *Biochem, Biophys. Commun.* 183:917–924.

Teeter et al., 1991, "Analysis of the Chinese Hamster P–Glycoprotein/Multidrug Resistance Gene *pgp1* Reveals that the Ap–1 Site is Essential for Full Promoter Activity," *Cell Growth Diff.* 2:429–437.

Thiebaut et al., 1987, "Cellular localization of the multidrug–resistance gene product P–glycoprotein in normal human tissues," *Proc. Natl. Acad. Sci. USA* 84:7735–7738.

Thorgeirsson et al., 1987, "Expression of the Multidrug Resistant Gene in Hepatocarcinogenesis and Regeneration Rat Liver," *Science* 236:1120–1122.

Toi et al., 1990, "Antineoplastic effect of erbstatin on human mammary and esophageal tumors in athymic nude mice," *Eur. J. Cancer* 26:722–724.

Ueda et al., 1987, "The Human Multidrug Resistance (*mdr1*) Gene," *J. Biol. Chem.* 262:505–508.

Umezawa and Imoto, 1991, "Use of Erbstsatin as Protein Tyrosin Kinase Inhibitor," *Meth. Enzymol.* 201:379–385.

Unger et al., 1990, "Hexadecylphosphocholine in the topical treatment of skin metastases in breast cancer patients," *Cancer Treat. Rev.* 17:243–246.

Vogler et al., 1991, "A phase I trial of bone marrow purging in acute leukemia with alkyl–lysophospholipid (ALP)," *Exp. Hematol.* 99:557 Abs.

Wiegmann et al., "Functional Dichotomy of Neutral and Acidic Sphingomyelinases in Tumor Neorosis Factor Signaling," *Cell* 78:1005–1015 (1994).

Yu et al., 1991, "Transfection with Protein Kinase Cα Confers Increased Multidrug Resistance to MCF–7 Cells Expressing P–Glycoprotein," *Cancer Commun.* 3:181–189.

Figure 4B

|  16 hr | 3 dy | 2 dy |
| - DAU ADR VBL VP | DAU VBL VP MTX | - CDDP CHL 5FU HU |

MDR1

B2M 1  2  3

METHODS FOR PREVENTING MULTIDRUG RESISTANCE IN CANCER CELLS

This is a continuation-in-part of International patent application Ser. No. PCT/US96/00422, filed Jan. 10, 1996, which is a continuation-in-part of U.S. Ser. No. 08/370,724, filed Jan. 10, 1995, now abandoned, which is a continuation-in-part of U.S. Ser. No. 07/947,659, filed Sep. 18, 1992, now abandoned, the specifications of each of which are hereby incorporated by reference in their entireties.

This invention was made with support under Grant Nos. 1-R01-CA62099 and 2-R37-CA40333 from the National Institutes of Health. The government has certain rights in this invention.

BACKGROUND OF THE INVENTION

1. Field of the Invention

This invention is directed to methods for preventing the emergence of multidrug resistance in tumor cells during cancer chemotherapy. In particular, it relates to the use of inhibitors of particular pathways of signal transduction to prevent the induction of the multidrug resistance (MDR1) gene by chemotherapeutic drugs. MDR1 gene expression, which results in tumor cell resistance to subsequent treatment with certain chemotherapeutic drugs is shown herein to be induced in response to treatment with various cytotoxic agents. Inhibitors of protein kinases, cytoplasmic calcium antagonists and calmodulin inhibitors, phosphoinositol-dependent phospholipase C inhibitors, and substances that inhibit activation of the transcription factor NF-κB (each of which have been implicated in intracellular eukaryotic signal transduction) are also shown herein to suppress this cellular response. Therefore, such inhibitors are useful in preventing MDR1 induction by chemotherapeutic drugs in a variety of tumor cells, when administered prior to and/or simultaneously with cytotoxic drug treatment in cancer patients.

2. Summary of the Related Art

Chemotherapy is a primary form of conventional cancer treatment. However, a major problem associated with cancer chemotherapy is the ability of tumor cells to develop resistance to the cytotoxic effects of anti-cancer drugs during the course of treatment. It has been observed that tumor cells can become simultaneously resistant to several chemotherapeutic drugs with unrelated chemical structures and mechanisms of action. This phenomenon is referred to as multidrug resistance. The best documented and clinically relevant mechanism for multidrug resistance in tumor cells is correlated with the expression of P-glycoprotein, the product of the MDR1 gene.

P-glycoprotein is a broad specificity efflux pump located in the cell membrane, and functions by decreasing the intracellular accumulation of many lipophilic cytotoxic drugs, including some widely used anticancer agents such as anthracyclines, vinca alkaloids, epipodophyllotoxins, actinomycin D and taxol, thereby rendering cells resistant to these drugs (Pastan and Gottesman, 1991, *Annu. Rev. Med.* 42: 277–286; Roninson (ed.), 1991, *Molecular and Cellular Biology of Multidrug Resistance in Tumor Cells*, Plenum Press, New York; Schinkel and Borst, 1991, *Sem. Cancer Biol.* 2: 213–226).

Human P-glycoprotein is expressed in several types of normal epithelial and endothelial tissues (Cordon-Cardo et al., 1990, *J. Histochem. Cytochem.* 38: 1277–1287; Thiebaut et al., 1989, *Proc. Natl. Acad. Sci. USA* 84: 7735–7738), as well as in hematopoietic stem cells (Chaudhary and Roninson, 1991, *Cell* 66: 85–94), and a subpopulation of mature lymphocytes (Neyfakh et al., 1989, *Exp. Cell Res.* 185: 496–505). More importantly, MDR1 mRNA or P-glycoprotein have been detected in most types of human tumors, both before and after chemotherapeutic treatment (Goldstein et al., 1989, *J. Natl. Cancer Inst.* 81: 116–124; Noonan et al., 1990, *Proc. Natl. Acad. Sci. USA* 87: 7160–7164). The highest levels of MDR1 expression are usually found in tumors derived from MDR1-expressing normal tissues; e.g., renal, adrenocortical or colorectal carcinomas. In other types of solid tumors and leukemias, MDR1 expression prior to treatment is usually relatively low or undetectable, but a substantial fraction of such malignancies express high levels of MDR1 after exposure to chemotherapy (Goldstein et al., 1989, ibid.). Prior to the present invention, the increase in MDR1 expression after chemotherapy was believed to result from in vivo selection for rare, pre-existing tumor cells that were already inherently resistant to chemotherapeutic drugs due to MDR1 expression.

Even low levels of MDR1 expression have been correlated with the lack of response to chemotherapy in several different types of cancer (Chan et al., 1990, *J. Clin. Oncol.* 8: 689–704; Chan et al., 1991, *N. Engl. J. Med.* 325: 1608–1614; Musto et al., 1991, *Brit. J. Haematol.* 77: 50–53), indicating that P-glycoprotein-mediated multidrug resistance represents an important component of clinical drug resistance. Whereas many clinical and pre-clinical studies have addressed pharmacological strategies for inhibiting P-glycoprotein function (Ford and Hait, 1990, *Pharmacol. Rev.* 42: 155–199), prior to the present invention, little was known about the factors that are responsible for the induction or up-regulation of P-glycoprotein expression in tumor cells under conditions relevant to cancer chemotherapy. Understanding such factors provides insight into the development of methods for preventing the appearance of P-glycoprotein in human tumors, thus reducing the incidence of multidrug resistance in cancer, and leading to more effective chemotherapy of cancer.

Numerous gene transfer studies have demonstrated that elevated expression of the MDR1 gene is sufficient to confer the multidrug resistance phenotype (Roninson, 1991, ibid.). For instance, mouse NIH 3T3 cells infected with a recombinant retrovirus carrying human MDR1 cDNA became multidrug-resistant in proportion to the density of human P-glycoprotein on their surface; the correlation was not affected by the presence or absence of cytotoxic selection (Choi et al., 1991, *Proc. Natl. Acad. Sci. USA* 88: 7386–7390).

Nevertheless, consistent association of other biochemical changes with multidrug-resistant cells suggested that these alterations may also play a role in multidrug resistance, possibly by affecting the expression or function of P-glycoprotein. The most prominent of such changes is the increased activity of protein kinase C (PKC), found in many, but not all, multidrug-resistant cell lines obtained after multiple steps of cytotoxic selection (Aquino et al., 1990, *Cancer Commun.* 2: 243–247; Fine et al., 1988, *Proc. Natl. Acad. Sci. USA* 85: 582–586; O'Brian et al., 1989, *FEBS Lett.* 246: 78–82; Posada et al., 1989, *Cancer Commun.* 1: 285–292). PKC activation has been shown to increase the level of drug resistance in some drug-sensitive and multidrug-resistant cells lines (Ferguson and Cheng, 1987, *Cancer Res.* 47: 433–441; Fine et al., 1988, ibid.; Yu et al., 1991, *Cancer Commun.* 3: 181–189). Although PKC is reported to be capable of phosphorylating P-glycoprotein (Chambers et al., 1990, *Biochem. Biophys. Res. Commun.* 169: 253–259; Chambers et al., 1990, *J. Biol. Chem.* 265:

7679–7686; Hamada et al., 1987, *Cancer Res.* 47: 2860–2865), it is not known whether such phosphorylation is responsible for the observed changes in drug resistance. While it has been shown that certain PKC inhibitors reversed multidrug resistance in some P-glycoprotein expressing cell lines (O'Brian et al., 1989, ibid.; Posada et al., 1989, *Cancer Commun.* 1: 285–292; Palayoor et al., 1987, *Biochem. Biophys. Res. Commun.* 148: 718–725), the available evidence suggests that at least some of the observed effects were due to direct inhibition of P-glycoprotein function by the tested compounds rather than inhibition of PKC-mediated phosphorylation (Ford et al. 1990, *Cancer Res.* 50: 1748–1756; Sato et al., 1990, *Biochem. Biophys. Res. Commun.* 173: 1252–1257). These studies have provided no indication that PKC-interactive agents could have an effect on expression, rather than phosphorylation or function, of P-glycoprotein.

Several laboratories have investigated the factors that regulate MDR1 gene expression in normal and malignant cells. One example of normal physiological regulation of an MDR1 homolog was found in mouse uterine endometrium, where the expression of a mouse mdr gene was induced by steroid hormones at the onset of pregnancy (Arceci et al., 1990, *Molec. Repro. Dev.* 25: 101–109; Bates et al., 1989, *Molec. Cell. Biol.* 9: 4337–4344). In rat liver, the expression of an mdr gene was found to be inducible by several carcinogenic or cytotoxic xenobiotics; similar induction was also observed during liver regeneration (Fairchild et al., 1987, *Proc. Natl. Acad. Sci. USA* 84: 7701–7705; Thorgeirsson et al., 1987, *Science* 236: 1120–1122). Further, a rodent homolog of MDR1 was induced in several cell lines in response to treatment with certain cytotoxic drugs (Chin et al., 1990, *Cell Growth Diff.* 1: 361–365). In contrast, no induction of the human MDR1 gene by cytotoxic drugs was detected in any of the human cell lines tested in the same study. Other investigators have also failed to detect MDR1 induction upon treatment with cytotoxic drugs (Schinkel and Borst, 1991, *Sem. Cancer Biol.* 2: 213–226).

Several studies have indicated, however, that the human MDR1 gene may be susceptible to stress induction, under certain conditions. Thus MDR1 expression in some human cell lines was increased by treatment with heat shock, arsenite (Chin et al., 1990, *J. Biol. Chem.* 265: 221–226) or certain differentiating agents (Mickley et al., 1989, *J. Biol. Chem.* 264: 18031–18040; Bates et al., ibid.). Some cytotoxic P-glycoprotein substrates were reported to stimulate transcription of a reporter gene from the human MDR1 promoter (Kohno et al., 1989, *Biochem. Biophys. Res. Commun.* 165: 1415–1421; Tanimura et al., 1992, *Biochem. Biophys. Res. Commun.* 183: 917–924) and to increase P-glycoprotein expression in a mesothelioma cell line after prolonged exposure (Light et al., 1991, *Int. J. Cancer* 49: 630–637). Despite such reports of MDR1 induction, however, it has never been determined whether short-term exposure to any agents used in cancer chemotherapy could induce expression of the MDR1 gene in human cells, and whether MDR1 induction could be prevented.

Recently, Kiowa et al. (1992, *FEBS Lett.* 301: 307–309) have reported that the addition of a flavonoid, quercetin, can prevent an increase in MDR1 expression in a hepatocarcinoma cell line induced by arsenite, a compound which is not used in cancer treatment, but is known to activate the transcriptional pathway mediated by the heat shock response element in the MDR1 promoter. Although not disclosed by Kiowa et al., inhibition of PKC activity is one of the biological effects of quercetin (Gschwendt et al., 1984, *Biochem. Biophys. Res. Commun.* 124: 63). It is possible therefore that PKC inhibition by quercetin could be responsible, in part, for the observed inhibition of MDR1 induction by arsenite. However, it is noteworthy that the ability of quercetin to inhibit a transcriptional response mediated by the heat shock response element is believed to those skilled in the art to be unrelated to PKC inhibition. (see, e.g., Kantengwa and Polla, 1991, *Biochem. Biophys. Res. Commun.* 180: 308–314). Furthermore, Kiowa et al. provide no suggestion that non-flavonoid PKC inhibitors would be able to inhibit MDR1 induction by arsenite, or that quercetin would be able to inhibit the induction of MDR1 expression when used in combination with chemotherapeutic drugs or any other agents that are not known to activate the heat shock response element-mediated pathway.

In addition to MDR1, another pleiotropic drug transporter has been recently discovered (Grant et al., 1994, *Cancer Res.* 54: 357–361)). This protein, termed the Multidrug Resistance-associated Protein (MRP), has been shown to confer a pattern of resistance to cytotoxic, particularly chemotherapeutic, drugs similar to the P-glycoprotein transporter encoded by the MDR1 gene. No inhibitors of MRP expression have been previously reported.

SUMMARY OF THE INVENTION

The present invention relates to the use of inhibitors of particular pathways of signal transduction inhibitors for preventing the emergence of multidrug resistance in cancer cells, and an in vitro method for identifying these inhibitors which would be useful towards the same goal.

This invention is based, in part, on the discovery that anticancer drugs, whether or not transported by P-glycoprotein, can induce the expression of the MDR1 gene in human tumor cells of diverse tissue origins. The increase in MDR1 gene expression is observed at both the mRNA and protein levels. MDR1 induction is also observed upon treatment of cells with PKC agonists. Further, this induction by either a cytotoxic drug or a PKC agonist can be prevented by treatment of cells with a protein kinase inhibitor, indicating that a protein kinase-mediated pathway is involved in MDR1 gene induction, and that protein kinase inhibitors may be useful in preventing the expression of MDR1 gene in cancer cells exposed to chemotherapeutic agents. More specifically, this inhibitory effect is associated with inhibition of PKC, since protein kinase inhibitors that are inactive against PKC fail to suppress MDR1 induction, while protein kinase inhibitors which have potent effects on PKC efficiently inhibit the response.

In addition, certain other substances which interfere with signal transduction in eukaryotic, particularly mammalian, cells have been found to prevent MDR1 induction by cytotoxic drugs or PKC agonists. These include cytoplasmic calcium antagonists and calmodulin inhibitors, phosphoinositol-dependent phospholipase C inhibitors, as well as substances that inhibit activation of the transcription factor NF-κB.

The ability of chemotherapeutic drugs to induce MDR1 expression in human cells upon short-term exposure in vitro indicates that cancer chemotherapy induces multidrug resistance directly, rather than through selection of pre-existing rare variants. Such direct induction is likely to occur during a patient's course of drug treatment, and it would account, at least in part, for the observed increased incidence of MDR1 expression in treated relative to untreated malignancies. Hence, administration of signal transduction inhibitors as disclosed herein prior to and/or simultaneously with the chemotherapy involving cytotoxic drugs may be useful in preventing MDR1 induction, and thus prevent the emergence of multidrug resistant cancer cells, leading to a more favorable therapeutic outcome.

The invention is illustrated by way of examples in which PKC agonists are shown to induce MDR1 expression in normal peripheral blood lymphocytes (PBL) and tumor cells. Additionally, various cytotoxic anticancer drugs are also described to be capable of activating the MDR1 gene. Importantly, protein kinase inhibitors, cytoplasmic calcium antagonists and calmodulin inhibitors, phosphoinositol-dependent phospholipase C inhibitors, and inhibitors of transcription factor NF-κB activation, are shown herein to prevent this MDR1 induction mediated by PKC agonists or cytotoxic drugs, especially in tumor cells that have little or no detectable P-glycoprotein prior to treatment.

For the purposes of this invention, the term "little or no P-glycoprotein" is intended to describe low levels of mRNA or protein expression such as are found in certain, well-characterized drug-sensitive cell lines, for example, KB-3-1 (see Noonan et al., ibid.). A variety of uses are encompassed by the invention described herein, including but not limited to, the prevention of the appearance of multidrug resistant tumor cells during chemotherapy of cancer.

In another aspect, the present invention provides a method for decreasing multidrug resistance in cancer cells, and an in vitro method for identifying protein kinase inhibitors which would be useful towards this goal. This aspect of the invention is based, in part, on the discovery that certain protein kinase inhibitors can inhibit expression of a multidrug-resistance associated protein, termed MRP (Grant et al., 1994, ibid.), in cancer cells that express this protein in the absence of the inhibitor. This aspect of the invention is shown by way of examples in which protein kinase inhibitors are shown to inhibit MRP expression in tumor cells expressing this protein. A variety of uses are encompassed by this aspect of the invention as described herein, including but not limited to, decreasing expression levels of this protein in multidrug resistant tumor cells during cancer chemotherapy.

Specific preferred embodiments of the present invention will become evident from the following more detailed description of certain preferred embodiments and the claims.

BRIEF DESCRIPTION OF THE DRAWINGS

FIG. 1. Effects of phorbol ester (TPA), diacylglycerol (DOG) and staurosporine (Staur) on P-glycoprotein function and expression of H9 cell line.

FIG. 2A: Effects of TPA or DOG, with or without staurosporine treatment, on MDR1 mRNA expression in H9 cells.

FIG. 2B: Time course of induction of MDR1 mRNA in H9 cells by TPA. The two negative control (neg. con.) lanes correspond to PCR carried out with water or reverse transcriptase mixture without RNA in place of cDNA.

FIG. 2C: Induction of MDR1 mRNA in K562 cells by TPA or DOG and in MCF-7 cells by TPA.

FIG. 4. cDNA-PCR analysis of MDR1 mRNA expression in drug-treated cells. In each lane, the upper band (167 bp) corresponds to MDR1, and the lower band (120 bp) to $\beta_2$-microglobulin specific PCR products, amplified in separate tubes.

FIG. 4B. MDR1 induction in K562 cells treated with different drugs. The times of drug exposure are indicated. The drugs and their concentrations are as follows: (−), untreated cells; DAU, 250 ng/mL daunorubicin; ADR, 500 ng/mL Adriamycin; VBL, 20 ng/mL vinblastine; VP, 1 $\mu$g/mL etoposide; MTX, 200 ng/mL methotrexate; CDDP, 3 $\mu$g/mL cisplatin; CHL, 50 $\mu$M chlorambucil; 5FU, 2 $\mu$g/mL 5-fluorouracil; HU, 30 $\mu$M hydroxyurea.

FIG. 5. Effect of protein kinase inhibitors on MDR1 mRNA induction by cytotoxic drugs in H9 cells. In each experiment, the inhibitors staurosporine (ST), H7, Iso-H7 (IH7) or HA1004 (HA) were added twice, the first time immediately prior to the addition of the corresponding drug and the second time after the specified period of time.

FIG. 6. Vinblastine resistance in Ara-C or Adriamycin-treated K562 cell.

FIG. 7. cDNA-PCR analysis of inhibition by protein kinase inhibitors of MDR1 mRNA expression induced by treatment with Ara-C or TPA. In each lane, the upper band (167 bp) corresponds to MDR1, and the lower band (120 bp) to $\beta_2$-microglobulin specific PCR products, amplified in separate tubes.

FIG. 8. cDNA-PCR analysis of inhibition by cytoplasmic calcium antagonists and calmodulin inhibitors, phosphoinositol-dependent phospholipase C inhibitors, and inhibitors of transcription factor NF-κB activation of MDR1 mRNA expression induced by treatment with Ara-C or any of a variety of cytotoxic drugs. In each lane, the upper band (167 bp) corresponds to MDR1, and the lower band (120 bp) to $\beta_2$-microglobulin specific PCR products, amplified in separate tubes.

FIG. 9. cDNA-PCR analysis of inhibition by protein kinase inhibitors of MRP mRNA expression. In each lane, the upper band (292 bp) corresponds to MRP, and the lower band (120 bp) to β$_2$-microglobulin specific PCR products, amplified in separate tubes.

DETAILED DESCRIPTION OF THE INVENTION

Figure 1A:
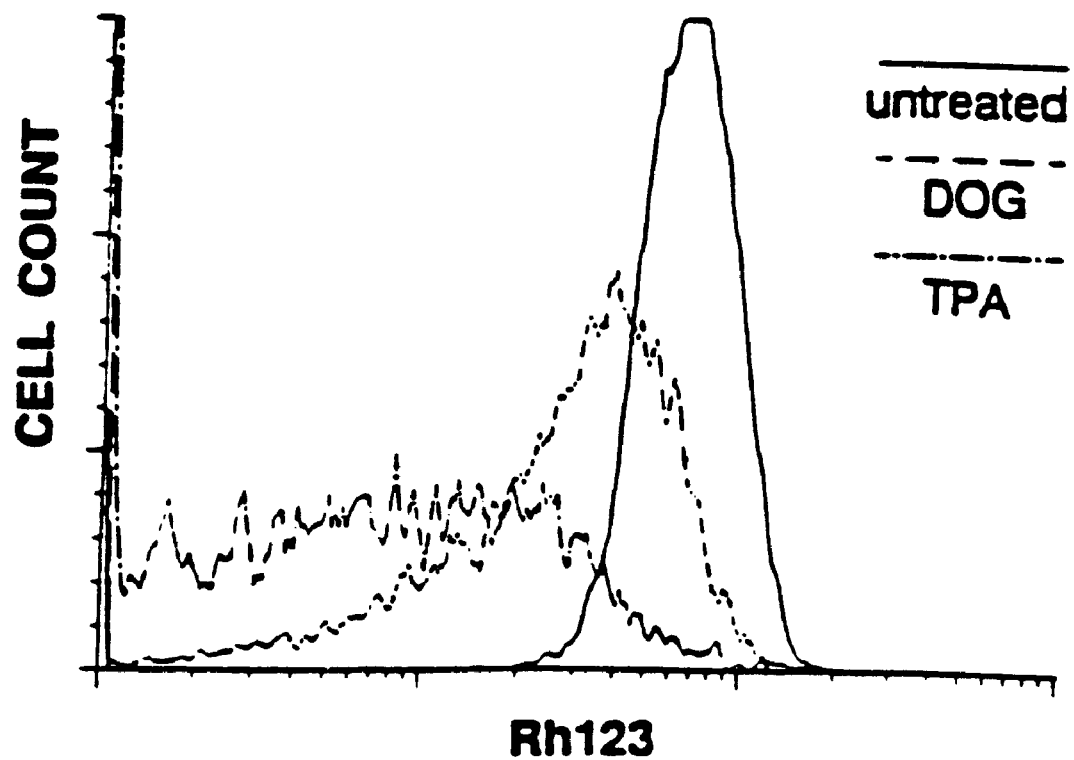
FIG. 1A: Three hr Rh123 accumulation by untreated and TPA- or DOG-treated cells.
Figure 1B:
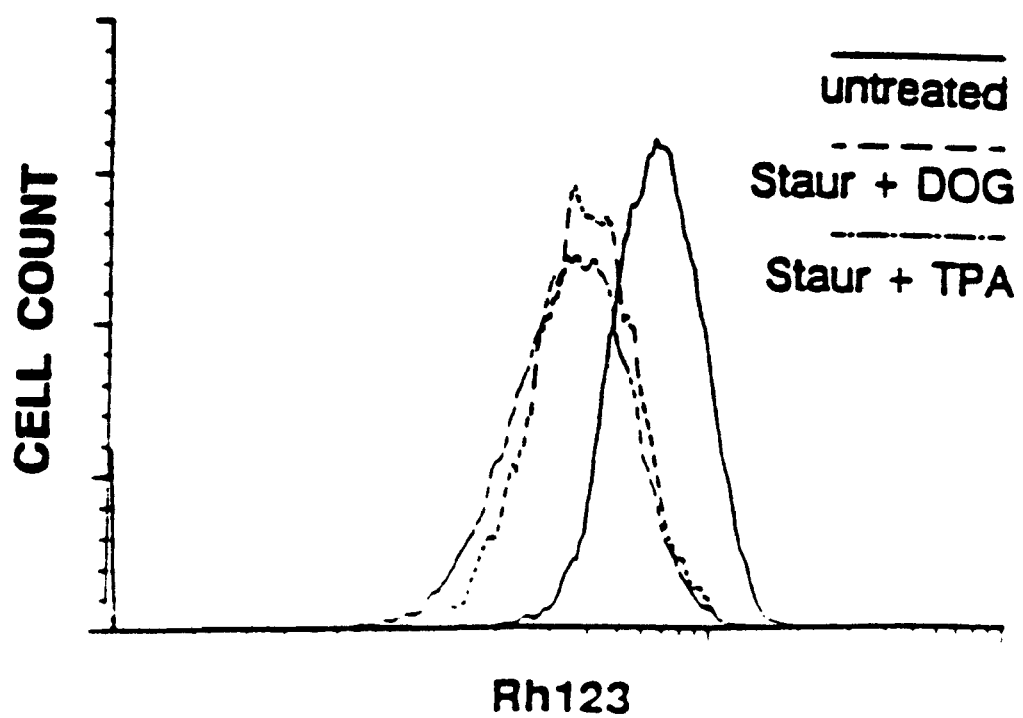
FIG. 1B: Three hr RH123 accumulation by untreated cells and cells treated with TPA or DOG pretreatment with staurosporine.
Figure 1C:
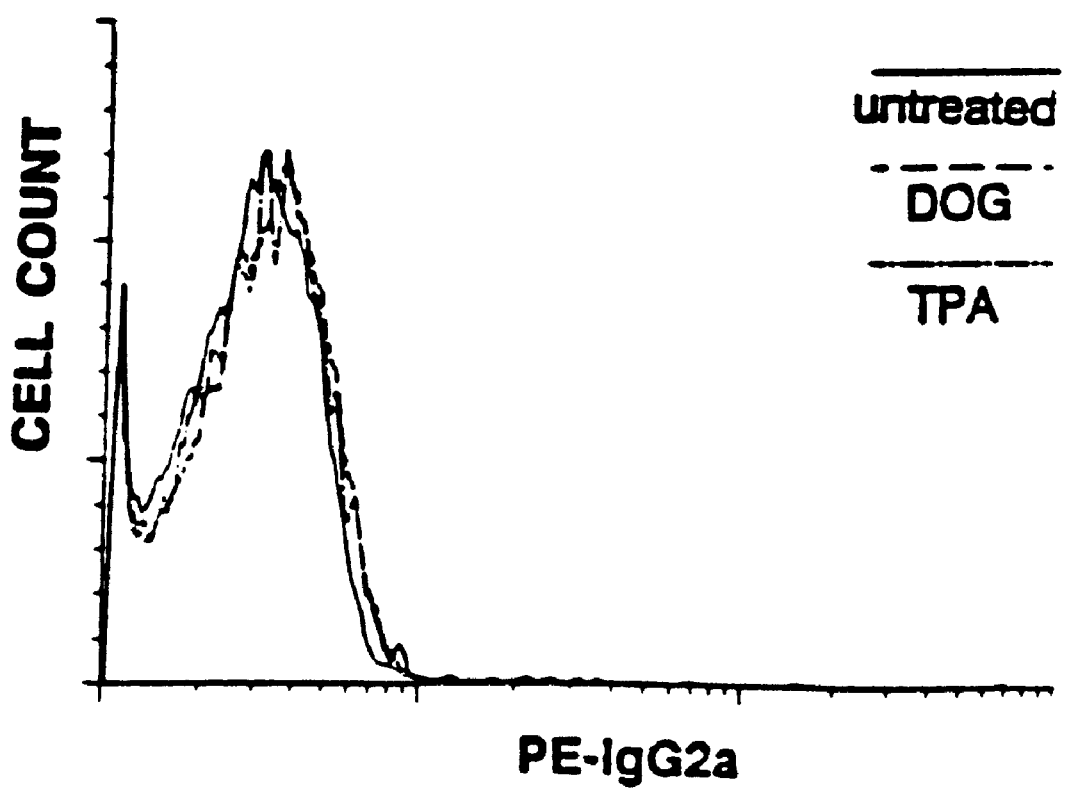
FIG. 1C: Staining of untreated and TPA- or DOG-treated cells with IgG2a isotype control.
Figure 1D:
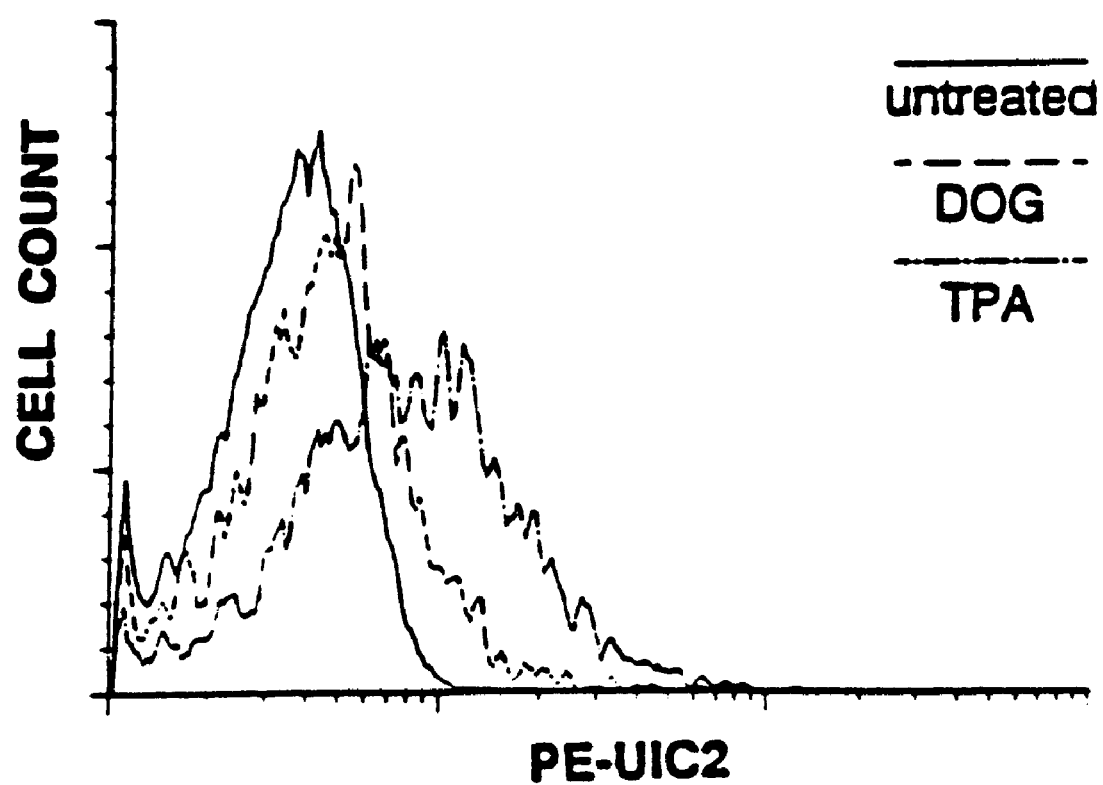
FIG. 1D: Same as in C, stained with UIC2 antibody.
Figure 1E:
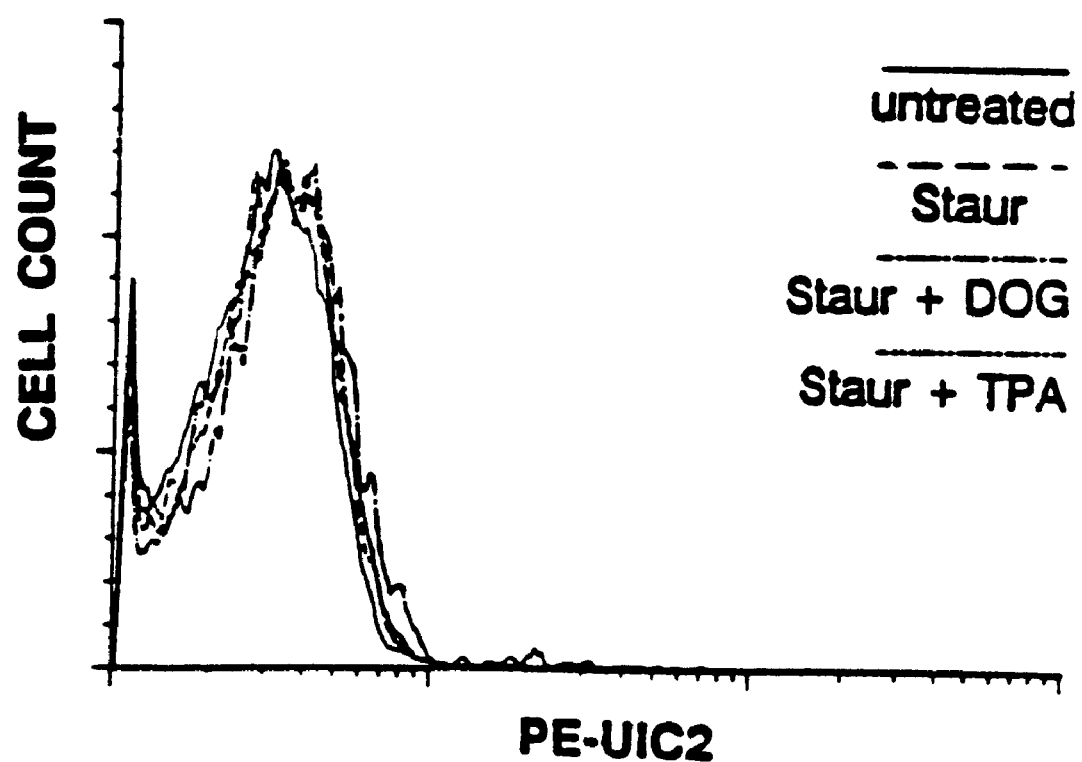
FIG. 1E: UIC2 staining of untreated cells or cells treated with staurosporine alone or with TPA or DOG pretreatment with staurosporine.

The present invention relates to the use of particular inhibitors of intracellular signal transduction in eukaryotic, particularly mammalian, cells to prevent the emergence of the multidrug resistance phenotype in cancer cells. The discovery of MDR1 induction by cytotoxic drugs and the ability of the inhibitors disclosed herein to prevent such induction are fully described and exemplified in the Examples below. For clarity of discussion, the invention is described in terms of a variety of signal transduction inhibitors, including protein kinase inhibitors, cytoplasmic calcium antagonists and calmodulin inhibitors, phosphoinositol-dependent phospholipase C inhibitors, and inhibitors of transcription factor NF-κB activation, which have potent effects, for example, on PKC activity in a panel of human tumor cell lines. However, the invention can be analogously applied to a wide variety of in vitro cell lines and in vivo tumors treated with other chemotherapeutic drugs, using any of the inhibitors of the invention, as well as analogues and derivatives thereof and additional compounds not explicitly disclosed herein which act at the same or equivalent signal transduction targets. Specific embodiments of certain inhibitors are exemplified as described below. It will be understood that any of a variety of analogues of the specific inhibitors disclosed herein, known in the art or prepared using methods known in the art, are also encompassed by the invention as herein described.

1. Induction of MDR1 Gene Expression

TPA (12-o-tetradecanoylphorbol-13-acetate), an efficient PKC activator, and diacylglycerol, a physiological stimulant of PKC, are shown in Examples 1 and 2, below, to increase MDR1 gene expression in normal human PBL, and in cell lines derived from different types of leukemias or solid tumors. The effect of TPA is observed in all the tested cell lines that expressed P-glycoprotein prior to treatment, and in some but not all other cell lines without detectable P-glycoprotein expression prior to treatment. It is possible, however, that MDR1 expression could be induced in the non-responsive cell lines by higher concentrations of TPA than those tested as described herein. The observed effects of TPA and diacylglycerol indicate that MDR1 expression in human cells may be regulated through a PKC-mediated signal transduction pathway.

The increase in MDR1 expression in cells treated with the PKC agonists is observed at the level of both P-glycoprotein and steady-state levels of MDR1 mRNA, which may reflect either increased transcription or decreased mRNA degradation. It is known that the major ("downstream") promotor of the human MDR1 gene (Ueda et al., 1987, *J. Biol. Chem.* 262: 505–508) contains an AP-1 site responsible for the stimulation of transcription by TPA (Angel et al., 1987, *Cell* 49: 729–739; Lee et al., 1987, *Cell* 49: 741–752). The AP-1 site and its surrounding sequences are conserved between the human MDR1 gene and its rodent homologs (Hsu et al., 1990, *Molec. Cell Biol.* 10: 3596–3606; Teeter et al., 1991, *Cell Growth Diff.* 2: 429–437). The AP-1 sequence of the hamster pgpl gene was shown to be an essential positive regulator of its promoter (Teeter et al., 1991, *Cell Growth Diff.* 2: 429–437), although the corresponding element of the homologous mouse mdrla (mdr3) gene may have a negative regulatory effect (Ikeguchi et al., 1991, *DNA Cell Biol.* 10: 639–649). Thus, it is possible that the AP-1 element of the human MDR1 promoter is directly responsible for the stimulation of MDR1 expression by PKC agonists.

The induction of MDR1 gene expression by a PKC-mediated pathway is consistent with previous observations that multidrug-resistant cell lines selected for increased P-glycoprotein expression frequently contained elevated levels of PKC (Aquino et al., ibid.; Fine et al., ibid.; O'Brian et al., ibid.; Posada et al., ibid.). An increase in PKC activity could represent an early event responsible for increased MDR1 gene expression during the selection of such cell lines. This interpretation does not preclude, however, that the phosphorylation of the induced P-glycoprotein by PKC could further increase P-glycoprotein activity. Evidence for the latter hypothesis comes from the study of Yu et al. (1991, *Cancer Commun.* 3: 181–189), who found that the level of drug resistance in a multidrug-resistant subline of MCF-7 cells, obtained after transfection with MDR1 cDNA transcribed from a heterologous promoter, could be increased by the introduction of a vector expressing high levels of PKCα. The increased resistance in the PKCα transfectants was accompanied by increased P-glycoprotein phosphorylation, without apparent changes in expression levels.

PKC plays a central role in various signal transduction pathways, associated with different adaptive, proliferative and differentiative processes. Even though PKC agonists have been found to induce MDR1 expression in normal and malignant hematopoietic cells, the same result has not been achieved using hematopoietic growth factors that may also act through PKC-mediated pathways. Furthermore, PKC agonists induce MDR1 expression in cell lines of not only hematopoietic but also epithelial origin, indicating that PKC-mediated regulation of MDR1 expression may have a general physiological role.

PKC-mediated mechanisms have been implicated in the transcriptional response to DNA damage by UV irradiation or alkylating agents (Kaina et al., 1989, in M. W. Lambert and J. Laval (ed.), *DNA Repair Mechanisms and Their Biological Implications in Mammalian Cells*, Plenum Press, New York; Papathanasiou and Fornace, 1991, pp. 13–36 in R. F. Ozols (ed.), *Molecular and Clinical Advances in Anticancer Drug Resistance*, Kluwer Academic Publishers, Boston, Mass.). PKC activation has also been associated with cellular responses to other cytotoxic drugs, such as cytosine arabinoside (Kharbanda et al., 1991, *Biochemistry Cancer Res.* 49: 6634–6639). Thus, PKC-mediated induction of MDR1 expression could be a part of a general stress response to different types of cellular damage, including the damage produced by cytotoxic chemotherapeutic drugs.

The present invention discloses that MDR1 expression in human leukemia and solid-tumor derived cell lines can be induced by short-term exposure to a number of different cytotoxic drugs that are used in cancer chemotherapy (see Example 3, below). MDR1 induction, both at the mRNA and at the protein levels, was observed in a subpopulation of cells treated with either P-glycoprotein-transported agents (Adriamycin, daunorubicin, vinblastine, etoposide) or chemotherapeutic drugs that are not transported by P-glycoprotein (such as methotrexate, 5-fluorouracil, chlorambucil, cisplatinum, hydroxyurea and 1-β-D-arabinofuranosylcytosine (Ara-C), an effective anti-leukemic drug (Kharbanda et al., 1991, *Biochemistry* 30: 7947–7952)). Since MDR1 expression does not provide resistance to drugs of the second group, and because MDR1 induction could be achieved after short times of drug exposure (less than one cell generation in many cases), these findings indicate that cytotoxic selection for MDR1-expressing cells was not responsible for the observed increase in MDR1 expression. MDR1 induction became detectable at the same time as visible cell damage, indicating that expression was more likely to be an indirect consequence of such damage, rather than a direct response to specific agents.

Most importantly, MDR1 expression induced by treatment with cytotoxic drugs did not disappear after the removal of the drug, but was maintained for at least several weeks in cells cultured in drug-free media. P-glycoprotein-positive cells, growing in the absence of the drugs, showed no change in differentiation state. This result indicates that drug-induced MDR1 expression is a stable phenomenon which is not limited to dying or terminally differentiating cells. In addition to increased MDR1 expression, drug-treated cells displayed a 2–3 fold increase in resistance to vinblastine, a P-glycoprotein transported drug; such resistance was specifically associated with MDR1-expressing cells. Drug-treated cells also showed increased resistance to chlorambucil, a chemotherapeutic drug which is not transported by P-glycoprotein. The latter finding suggests that some other clinically relevant mechanisms of drug resistance may be co-induced with MDR1 expression after treatment with cytotoxic drugs.

Taken together, these findings suggested that treatment of human tumor cells with various drugs used in cancer chemotherapy could induce MDR1 expression directly, rather than by selection of preexisting genetic variants, as previously believed. The resulting increase in multidrug resistance was found to be stable and could be sufficient to reduce the response to chemotherapeutic drugs both in vitro and in vivo. It is likely that drug-mediated induction of MDR1 expression could occur during cancer chemotherapy, and could account, at least in part, for the observed increase in the incidence of MDR1 expression in drug-treated human tumors. This invention therefore provides the first demonstration of MDR1 induction under clinically relevant conditions and suggests that PKC may play a central role in such induction. This provides a basis for chemotherapeutic protocols that would prevent MDR1 induction during cancer chemotherapy through the inhibition of PKC.

2. Use of Protein Kinase Inhibitors to Prevent MDR1 Induction

The present invention demonstrates that protein kinase inhibitors, especially those with potent activity against PKC, are capable of preventing the induction of MDR1 gene expression in cancer cells. For example, staurosporine, a potent but non-selective inhibitor of PKC (Rüegg and Burgess, 1989, *Trends Pharmacol. Sci.* 10: 218–220), was found (at a concentration of 30 nM) to prevent MDR1 induction in P-glycoprotein-negative cells treated with TPA, diacylglycerol and a number of chemotherapeutic cytotoxic drugs, including Ara-C, vinblastine, methotrexate and Adriamycin. A variety of other protein kinase inhibitors, including H7 (50 $\mu$M), calphostin C (at a concentration of 1 $\mu$M, used in conjunction with white light illumination), and chelerythrine (5 $\mu$M), are also shown to prevent MDR1 induction by chemotherapeutic drugs.

Inhibition of MDR1 expression induced by treatment with Ara-C has also been demonstrated using inhibitors that have not previously been understood to have specificity for protein kinase C. Examples of such inhibitors include erbstatin and analogues of erbstatin, and neomycin sulfate. Erbstatin and its analogues, such as methyl-2,5-dihydroxycinnamate, are known to be capable of inhibiting the epidermal growth factor receptor tyrosine kinase (Umezawa and Imoto, 1991, *Meth. Enzymol.* 201: 379–385). This erbstatin analog was found to completely inhibit Ara-C induced MDR1 expression at a concentration of 32 $\mu$M (see, Example 4, below). This erbstatin analog was also found to inhibit MDR1 expression induced by treatment of sensitive cells with TPA, a known PKC agonist, consistent with anti-PKC activity (see Example 4 and FIG. 7F, infra). In addition to the erbstatin analogue, two other compounds known as inhibitors of protein tyrosine kinase, tyrphostin A25 and tyrphostin B46, were also found to inhibit Ara-C induced MDR1 expression, at concentrations of 50–100 $\mu$M.

The antibacterial compound, neomycin sulfate, was found to inhibit Ara-C induced MDR1 expression, when contacted with induced cells at a concentration of 10 mM. This concentration of neomycin showed no cellular toxicity on human H9 cells, and appears to be within the range of clinically-achievable concentrations. This compound has the advantage of being of general benefit to patients undergoing chemotherapy, and has been widely used for the treatment of bacterial intestinal infections in humans.

Interestingly, both erbstatin (Bishop et al., 1990, *Biochem. Pharmacol.* 40: 2129–2135) and neomycin sulfate (Chauhan et al., 1990, *FASEB J.* 4: A1779) have been reported to be protein kinase C inhibitors. Neomycin sulfate is also known to be an inhibitor of phosphoinositol-dependent phospholipase C (Cockroft et al., 1987, *J. Cell Biol.* 105: 2745–2758).

These findings provide evidence that protein kinase inhibitors, and in particular PKC inhibitors, are involved in MDR1 induction and suggest the possibility of using protein kinase inhibitors to prevent MDR1 gene activation.

Other protein kinase inhibitors, however, were found to be ineffective in inhibiting Ara-C induced MDR1 expression.

These include the PKC inhibitor D,L-threo-sphingosine (when used at 5 µM concentration; higher concentrations induced cellular toxicity). This was the only PKC inhibitor tested that did not inhibit MDR1 induction, suggesting that the observed cellular toxicity prevented administration of this compound at an effective inhibitory concentration. The tyrosine kinase inhibitor, herbimycin A, was also found to be ineffective at inhibiting MDR1 induction by Ara-C at concentrations ranging from 0.35–3 µM. Another tyrosine kinase inhibitor, genistein, only weakly inhibited Ara-C induced MDR1 expression, at a concentration of 150 µM.

Staurosporine is a P-glycoprotein inhibitor that may bind directly to P-glycoprotein (Sato et al., 1990, *Biochem. Biophys. Res. Commun.* 173: 1252–1257). In some P-glycoprotein-positive cell lines, however, staurosporine, when used alone, significantly increased P-glycoprotein expression. Additionally, two other P-glycoprotein binding compounds, cyclosporine A and verapamil, also known PKC inhibitors, increased P-glycoprotein expression in some of the P-glycoprotein-positive cell lines. These results suggest that protein kinase inhibitors may be more effectively used to prevent an increase in MDR1 in P-glycoprotein-negative or nearly negative tumors than in tumors already expressing P-glycoprotein in a large fraction of tumor cells. It should be noted, however, that the finding that staurosporine increased P-glycoprotein expression in a small number of hematopoietic that augmentation of P-glycoprotein expression by PKC inhibitors is a general property of P-glycoprotein-positive tumor cells, and that patients with P-glycoprotein-positive tumors cannot benefit from the use of protein kinase inhibitors to prevent further drug-induced increase of multidrug resistance in tumor cells.

P-glycoprotein negative solid tumors or leukemias can be identified by the analysis of biopsy material, surgical or hematological specimens of patients'tumors using techniques well known in the art (Roninson, ibid.). These techniques include but are not limited to immunocytochemical, immunohistochemical or immunofluorescent assays with P-glycoprotein-specific antibodies; vital staining with P-glycoprotein transported fluorescent dyes; Northern blot, dot blot or slot blot hybridization with MDR1-specific nucleic acid probes; or cDNA-PCR analysis of MDR1 mRNA. Working examples of some of the above assays are described in Examples 1 and 3, below. It should be noted that some cell lines that appear to be P-glycoprotein negative by protein or function-based assays are described in levels of MDR1 mRNA when assayed by cDNA-PCR (see Table I). This indicates that protein or function-based assays would be preferable as the primary criterion for the identification of tumors that are likely to benefit from the use of protein kinase inhibitors. Alternatively, cDNA-PCR or other methods for MDR1 mRNA measurement may be used with the understanding that MDR1 mRNA expression at the level of K562 cells or slightly (e.g. 2-fold) higher may still be indicative of P-glycoprotein negative tumors.

Although the protein kinase inhibitors tested herein are known to be non-selective in their inhibitory activities, i.e., their action is not specific for PKC, the studies described herein provide evidence that their ability to inhibit PKC activity may be a critical factor in the prevention of MDR1 induction. For example, a number of potent PKC inhibitors, including staurosporine, H7, chelerythrine, neomycin sulfate and calphostin C, are capable of inhibiting MDR1 induction by cytotoxic drugs. In contrast, HA1004, a protein kinase inhibitor that is inactive against PKC, is shown to be totally ineffective in preventing MDR1 induction. Hence, it is likely that any protein kinase inhibitor that is capable of inhibiting PKC, irrespective of its specificity for PKC, would be useful in preventing MDR1 induction in cancer cells.

Accordingly, any protein kinase inhibitor capable of preventing the induction of MDR1 by chemotherapeutic drugs as measured by any method described in Example 3, below, such as fluorescent dye accumulation, cDNA-PCR for MDR1 mRNA or staining with P-glycoprotein specific antibody, may be used in the practice of the method of the invention. Such inhibitors may be administered in a cancer patient bearing a solid tumor or leukemia prior to and/or simultaneously with treatment by chemotherapeutic drugs. Any anti-cancer drug commonly used in cancer chemotherapy is encompassed within the scope of this regimen, including, but not limited to, Ara-C, Adriamycin, daunorubicin, vinblastine, etoposide, methotrexate, 5-fluorouracil, chlorambucil, cisplatin, and hydroxyurea.

Prior to the present invention, a number of compounds capable of inhibiting PKC have been investigated in vitro and in vivo for potential use in cancer chemotherapy. However, it should be noted that while such compounds were found to show selective growth inhibition for tumor relative to normal cells (Powis and Kozikowski, 1991, *Clin. Biochem.* 24: 385–397; Grunicke et al., 1989, *Adv. Enzyme Regul.* 28: 201–216) they have not been shown or suggested to be capable of preventing MDR1 expression in cancer cells. In vitro studies have shown that the anti-proliferative effects of PKC inhibitors occurred at approximately the same dose as their PKC inhibitory activity (Grunicke et al., ibid.). Compounds tested in vivo include staurosporine and its benzoyl derivative CGP 41 251, which were found in nude mice to show anti-tumor effect at one-tenth of their maximum tolerated doses (MTD) (MTD was 1 mg/kg for staurosporine and 250 mg/kg for CGP 41 251) (Meyer et al., 1989, *Int. J. Cancer* 43: 851–856). Other staurosporine analogs shown to have antitumor activity in vivo include UCN-01 (Takahashi et al., 1987, *J. Antibiot.* 40: 1782–1784) and 8-N-(diethylaminoethyl) rebeccamycin (BMY 27557) (Schurig et al., 1990, *Proc. Amer. Assoc. Cancer Res.* 31: Abs. 2469). For the latter compound, optimal doses for i.p. administration ranged from a total of 108 mg/kg administered over nine injections/day at 12 mg/kg/injection to a single dose of 64 mg/kg.

Another group of PKC inhibitors actively investigated as anticancer agents comprises ether lipid analogues, including hexadecylphosphocholine, ET-18-OCH3, ilmofosine, SRI 62–834 and BM41440 (Powis and Kozikowski, 1991, *Clin. Biochem.* 24: 385–397; Grunicke et al., ibid.). Some of these agents have been used in clinical trials. The MTDs established in these trials for oral administration are 200 mg/day for ilmofosine (Berdel et al., 1988, *Proc. Amer. Assoc. Cancer Res.* 29: Abs. 2050) and 5 mg/kg body weight for BM41440 (Hermann et al., 1987, *Lipids* 22: 962–966). Hexadecylphosphocholine was also used topically for treatment of skin metastases of breast cancer, at a dose range of 0.2 to 38.5 g per patient, administered over 3 to 128 weeks (Unger et al., 1990, *Cancer Treat. Rev.* 17: 243–246). Compounds of this group were also tested as purging agents for autologous bone marrow transplantation (Vogler et al., 1991, *Exp. Hematol.* 99: 557 Abs.).

Another PKC inhibitor, suramin, has been used in the treatment of parasitic diseases, and is being evaluated in clinical trials as an antineoplastic agent. Continuous infusion of suramin at a rate designed to reach a peak of 300 µg/mL at the end of 14 days has shown activity in hormone-refractory prostate cancer (Myers et al., 1992, *J. Clin. Oncol.* 10: 875–877). A member of another class of PKC inhibitors, the flavonoid quercetin, was shown to potentiate the antitumor effect of cisplatin, a drug which is not transported by P-glycoprotein, in nude mice when administered i.p. at 20 mg/kg (Grunicke et al., ibid.).

The epidermal growth factor receptor tyrosine kinase inhibitor erbstatin has been reported to have antitumor activity in vivo (Imoto et al., 1987, *Japanese J. Cancer Res.* 78: 329–332; Toi et al., 1990, *Eur. J. Cancer* 26: 722–724). No evidence has been reported that erbstatin has any capacity to inhibit MDR1 induction by cytotoxic drugs.

While none of the above compounds (with the exception of staurosporine described in Examples 2 and 4, below) have been tested for the ability to prevent MDR1 induction by cytotoxic drugs, the results disclosed in the present invention strongly indicate that they are likely to possess such an effect, since all of them are capable of inhibiting PKC. The availability of in vivo animal and clinical trial data for these and other PKC inhibitors enables those skilled in the art to use such compounds in combination with conventional anticancer drugs to prevent the emergence of multidrug resistance during chemotherapy. These compounds may be administered with chemotherapeutic drug treatment at a dose range of about 1–250 mg/kg body weight, either by repeated injections, by continuous infusion, or as topical treatment.

In addition to these aspects of the present invention, an in vitro assay is disclosed for rapid identification of any compound which is capable of preventing the induction of MDR1 gene expression by chemotherapeutic drugs. For example, H-9 or K562 leukemia cell lines are treated with a test compound for about 30 minutes for 10–36 hours (though any time of culture over 1 hour may be sufficient, see FIG. 2B) prior to exposure to 10–25 $\mu$M Ara-C or 200 ng/mL vinblastine under standard tissue culture conditions, followed by evaluation of MDR1 induction by the drugs in cultures treated with the test compound, as compared to controls. Test compounds identified by such assays as being capable of preventing MDR1 induction by chemotherapeutic drugs, are used for patient treatment in the same manner as protein kinase inhibitors described herein.

3. Use of Phosphoinositol-dependent Phospholipase C Inhibitors to Inhibit MDR1 Expression The present invention also demonstrates that inhibitors of phosphoinositol-dependent phospholipase C (PI-PLC) are capable of preventing induction of MDR1 gene expression in cancer cells. The antibiotic neomycin sulfate, an inhibitor of PI-PLC, was found to completely prevent cytotoxic drug and PKC agonist induction of MDR1 expression at a concentration of 10 mM (see FIG. 8A). The present invention discloses the use of another inhibitor of PI-PLC, 1-(6-((1$\beta$-3-methoxyestra-1,3,5(10)-trien-17-y1)amino)hexyl)-1-H-pyrrole-2,5-dione (U73122; see Heemskerek et al., 1994, *Eur. J. Biochem.* 223: 543–551), that reduced the steady-state levels of MDR1 mRNA in Ara C-treated H9 cells. U73122 was active at significantly lower concentrations (10 $\mu$M) than neomycin sulfate.

In contrast, the inhibitor of phosphatidylcholine-specific phospholipase C (PC-PLC), D609 (tricyclodecan-9-yl-xanthogenate potassium) was without an effect when added at concentrations up to 100 $\mu$g/ml, the dose which has been shown to inhibit PC-PLC (see Wiegmann et al., 1994, *Cell* 78: 1005–1015). The high activity and specificity of U73122, including analogues and derivatives thereof that are specific inhibitors of PI-PLC, are advantageous for use in combined regimens of chemotherapeutic drug treatment to prevent the induction of MDR1 mediated drug resistance in cancer cells.

These results indicate that any inhibitor of PI-PLC may be used to prevent induction of MDR1 gene expression by cytotoxic, particularly chemotherapeutic, drugs. PI-PLC inhibitors capable of preventing the induction of MDR1 by chemotherapeutic drugs as measured by any method described in Example 3, below, such as fluorescent dye accumulation, cDNA-PCR for MDR1 mRNA or staining with P-glycoprotein specific antibody, may be used in the practice of the method of the invention. Such inhibitors may be administered in a cancer patient bearing a solid tumor or leukemia prior to and/or simultaneously with treatment by chemotherapeutic drugs. Any anti-cancer drug commonly used in cancer chemotherapy is encompassed within the scope of this regimen, including, but not limited to, Ara-C, Adriamycin, daunorubicin, vinblastine, etoposide, methotrexate, 5-fluorouracil, chlorambucil, cisplatin, and hydroxyurea.

4. Use of Cytoplasmic Calcium Antagonists and Calmodulin Inhibitors to Inhibit MDR1 Expression The present invention also demonstrates that cytoplasmic calcium antagonists and calmodulin inhibitors are capable of preventing induction of MDR1 gene expression in cancer cells. As used herein, the term "cytoplasmic calcium antagonist" will be understood to encompass calcium-specific chelators, agents which inhibit the intracellular release of calcium ions from cytoplasmic stores, and any agent which inhibits an increase in free cytoplasmic calcium concentration.

Figure 8A:
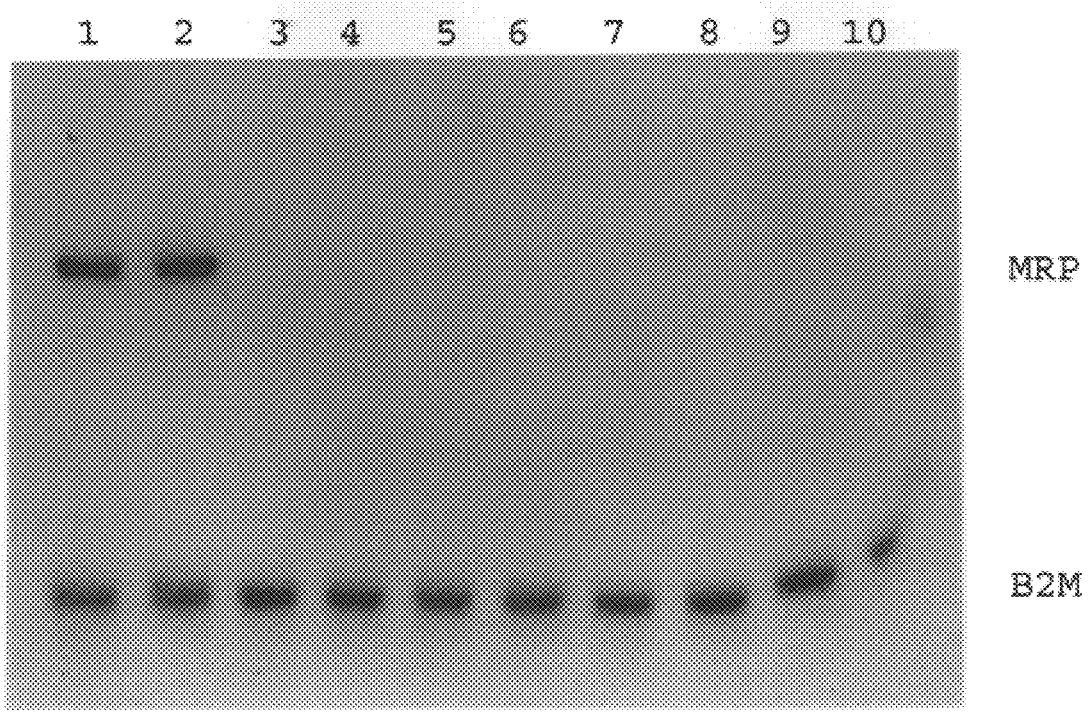
FIG. 8A. Effect of phosphoinositol-dependent phospholipase C inhibitor 1-(6-((1β-3-methoxyestra-1,3,5(10)-trien-17-yl)amino)hexyl)-1-H-pyrrole-2,5-dione (U73122) on AraC-induced MDR1 activation. H9 cells were treated (lanes 2 and 3) or untreated (lane 1) with 25 μM Ara C in the absence of (lane 2) or in the presence of 1 μM (lane 3) or 10 μM (lane 4) of U 73122 for 10 hrs at 37° C., 5% $CO_2$ in a humidified atmosphere. The inhibitor was added 45 min. prior to the addition of Ara C. After the completion of the treatment, the steady-state levels of MDR1 and $\beta_2$-microglobulin mRNA were determined by RT-PCR.
Figure 8B:
FIG. 8B. Induction of MDR1 expression by agents that cause intracellular $Ca^{2+}$ release. H9 cells were either untreated (lane 1) or treated with A23187 (10 μM, lane 2) or thapsigargin (10 μg/ml, lane 3) for 10 hrs at 37° C., 5% $CO_2$ in a humidified atmosphere. After the completion of the treatment, the steady-state levels of MDR1 and $\beta_2$-microglobulin mRNA were determined by RT-PCR.
Figure 8C:
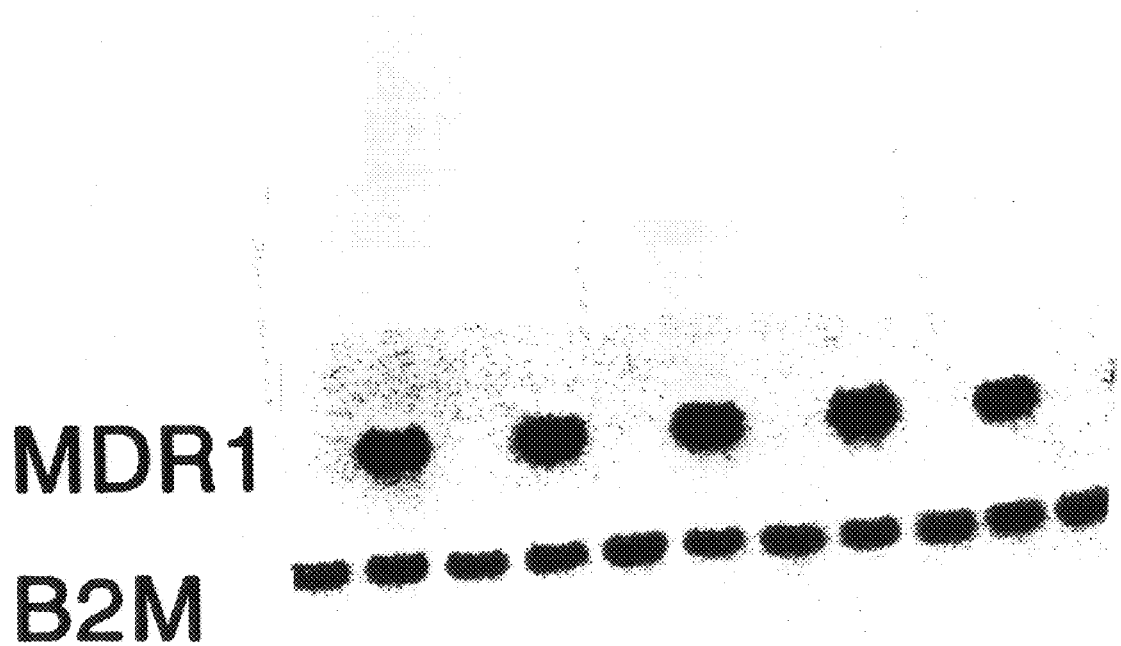
FIG. 8C. Effects of intracellular $Ca^{2+}$ chelator on MDR1 induction by cytotoxic drugs. H9 cells were treated with Ara C(25 μM shown in lanes 2 and 3, where lane 1 on the extreme left is a negative control lane receiving neither drug nor BAPTA/AM), Adriamycin (2 μM; shown in lanes 4 and 5) bleomycin (100 μg/ml; shown in lanes 6 and 7), 2-deoxyglucose (10 mM; shown in lanes 8 and 9) or nocodazole (2.5 μM; shown in lanes 10 and 11) for 10 hrs in Ca$^{2+}$-free RPMI-1640 media/10% dialyzed fetal bovine serum as indicated. BAPTA/AM was given 45 min. prior to the addition of cytotoxic drugs. Results of assays performed in the presence of BAPTA/AM are shown in lanes 3, 5, 9 and 11. Levels of MDR1 mRNA were determined by quantitative RT-PCR.

Two types of agents which increase the level of intracellular $Ca^{2+}$, namely the specific $Ca^{2+}$ ionophore A23187 (see Geng et al., 1995, *J. Cell Biol.* 129: 1651–1657) and an inhibitor of $Ca^{2+}$-dependent ATPase, thapsigargin (see Chakrabarti et al., *J. Cell. Biochem.* 58: 344–359) are capable of inducing MDR1 gene expression in H9 cells (FIG. 8B). A highly-specific $Ca^{2+}$ ion chelator, 1,2-bis(o-aminophenoxy)ethane-N,N,N',N'-tetraacetic acid, tetra (acetoxymethyl)ester (BAPTA/AM; see Bunn et. al., 1995, *J. Neurochem.* 64: 1370–1378) was found to inhibit induction of MDR1 gene expression by cytotoxic drugs. Pretreatment of H9 cells with BAPTA/AM at concentrations as low as 5 $\mu$M were found to completely abrogate the induction of MDR1 expression by different cytotoxic agents, such as Ara C(25 $\mu$M), Adriamycin (2 $\mu$M), bleomycin (100 $\mu$g/ml), 2-deoxyglucose (10 mM) and nocodazole (2.5 $\mu$M) (FIG. 8C). This inhibitory effect of BAPTA/AM was detectable when the chelator was given to the cells within the first 3 hrs prior to the addition of MDR1 inducing agents.

An inhibitor of intracellular release of calcium ions from cytoplasmic stores, 8-(dimethylamino)octyl-3,4,5-trimethoxybenzoate hydrochloride (TMB-8; Gandhi et al., 1992, *Biochim. Biophys. Acta* 1136: 68–74), was found to completely abrogate the ability of AraC to induce MDR1 gene expression in H9 cells when present at a concentration of 200 $\mu$M.

In addition, a calmodulin inhibitor (calmidazolium chloride; see Silver et al., 1986, *Biochem. Pharmacol.* 35: 2545–2551) was found to inhibit AraC-induced MDR1 gene expression when H9 cells were treated with the inhibitor at a concentration of 10 $\mu$M (see FIG. 8D).

These results indicate that cytoplasmic calcium antagonists and calmodulin inhibitors may be used to prevent induction of MDR1 gene expression by cytotoxic, particularly chemotherapeutic, drugs. Such inhibitors include calcium ion-specific chelators, calmodulin inhibitors and inhibitors of the intracellular effectors of calcium ion release, particularly from intracellular calcium stores such as endoplasmic reticulum. Inhibitors capable of preventing the induction of MDR1 by chemotherapeutic drugs as measured by any method described in Example 3, below, such as fluorescent dye accumulation, cDNA-PCR for MDR1 mRNA or staining with P-glycoprotein specific antibody, may be used in the practice of the method of the invention. Such inhibitors may be administered in a cancer patient bearing a solid tumor or leukemia prior to and/or simultaneously with treatment by chemotherapeutic drugs. Any anti-cancer drug commonly used in cancer chemotherapy is encompassed within the scope of this regimen, including, but not limited to, Ara-C, Adriamycin, daunorubicin, vinblastine, etoposide, methotrexate, 5-fluorouracil, chlorambucil, cisplatin, and hydroxyurea.

5. Use of Inhibitors of Transcription Factor NF-κB Activation to Inhibit MDR1 Expression The present invention also demonstrates that inhibitors of activation of eukaryotic transcription factor NF-κB are capable of preventing induction of MDR1 gene expression in cancer cells. It has been shown that AraC treatment of mammalian cells results in release of transcription factor NF-κB from an inhibitory subunit, followed by translocation of the active NF-κB to the nucleus (see Siebenlist et al., 1994, *Annu. Rev. Cell Biol.* 10: 405–455; Kopp et al., 1994, *Science* 265: 956–959). A variety of agents known to inhibit the activation of NF-κB as the result of stress stimuli were found to prevent induction of MDR1 gene expression by chemotherapeutic drugs. Pretreatment of H9 cells with pyrrolidone dithiocarbamate (100 $\mu$M), N-tosyl-L-phenylalanine chloromethyl ketone (25 $\mu$M), sodium salicylate (20 mM) or aspirin (acetylsalicylic acid, 10 mM) was found to completely abrogate induction of MDR1 gene expression by either Ara C (25 $\mu$M) or Adriamycin (2 $\mu$M).

These results indicate that inhibitors of NF-κB activation may be used to prevent induction of MDR1 gene expression by cytotoxic, particularly chemotherapeutic, drugs. Such inhibitors include aspirin, a commonly-used analgesic with a long record of accepted clinical use. This compound is now understood as being advantageous to patients undergoing cancer chemotherapy by preventing the induction of resistance to chemotherapeutic drugs.

NF-κB activation inhibitors capable of preventing the induction of MDR1 by chemotherapeutic drugs as measured by any method described in Example 3, below, such as fluorescent dye accumulation, cDNA-PCR for MDR1 mRNA or staining with P-glycoprotein specific antibody, may be used in the practice of the method of the invention. Such inhibitors may be administered in a cancer patient bearing a solid tumor or leukemia prior to and/or simultaneously with treatment by chemotherapeutic drugs. Any anti-cancer drug commonly used in cancer chemotherapy is encompassed within the scope of this regimen, including, but not limited to, Ara-C, Adriamycin, daunorubicin, vinblastine, etoposide, methotrexate, 5-fluorouracil, chlorambucil, cisplatin, and hydroxyurea.

6. Use of Protein Kinase Inhibitors to Inhibit MRP Expression

The present invention demonstrates that protein kinase inhibitors are also capable of inhibiting expression of a protein, termed the multidrug resistance-associated protein (MRP; Grant et al., ibid.). In contrast to MDR1, certain human tumor cells, such as H9 human T-cell leukemia cells, display robust expression of the MRP gene, as evidenced by cDNA-PCR experiments as disclosed in Example 8 and FIG. 9A, below. Treatment of such cells with certain protein kinase inhibitors results in a dramatic reduction of MRP expression. Compounds shown to be capable of inhibiting MRP expression in H-9 cells include staurosporine (at a concentration of 100 nM), neomycin sulfate (10 mM), chelerythrine (1–5 $\mu$M), and the erbstatin analogue, methyl-2,5-dihydroxycinnamate (32 $\mu$M).

The present invention thus provides a number of agents having related activities of benefit to cancer chemotherapy patients. These agents prevent the activation of the MDR1 gene by chemotherapeutic drugs, thereby suppressing the emergence of MDR1-mediated multidrug resistance during chemotherapy of patients bearing MDR1-negative tumors. In addition, these agents reduce MRP expression, thereby decreasing multidrug resistance mediated by MRP in MRP-positive tumors. One of these agents, neomycin sulfate, has the additional advantage of being a commonly-used antibiotic, which has been well-characterized clinically and whose use may have added benefits for combating adventitious bacterial infections in cancer chemotherapy patients.

The Examples which follow are illustrative of specific embodiments of the invention, and various uses thereof. They set forth for explanatory purposes only, and are not to be taken as limiting the invention.

EXAMPLE 1

A Protein Kinase Inhibitor Prevents Protein Kinase C Agonist-mediated MDR1 Induction in Normal and Tumor Cells 1. Materials and Methods 1.1 Cell Lines and Drug Treatment Normal human PBL were obtained from healthy volunteers by venipuncture after informed consent, followed by the isolation of low-density mononuclear cells by density gradient centrifugation in Histopaque-1077 (Sigma Chemical Co., St. Louis, Mo.). KG1 cell line was maintained in Iscove's modified Dulbecco medium with 20% fetal calf serum (FCS) and 2 mM L-glutamine, 100 units/mL penicillin and 100 $\mu$g/mL streptomycin (GIBCO Laboratories, Grand Island, N.Y.). MCF-7, EJ, KB-3-1, HeLa, and HT-1080 cell lines were maintained in DMEM with 10% FCS and 2 mM L-glutamine, 100 units/mL penicillin and 100 $\mu$g/mL streptomycin.

A stock solution of 1 mM Ara-C (Sigma) was prepared in sterile phosphate buffered saline (pH 7.2) and stored at −20° C. until use. Stock solutions of 100–1000 $\mu$g/mL TPA (Sigma) and 30 mM 1,2-dioctanoylglycerol (DOG or DiC$_8$) (Molecular Probes, Eugene, Oreg.) were prepared in dimethylsulfoxide (DMSO) and stored at −30° C. Stock solutions of chelerythrine, calphostin C, methyl-2,5-dihydroxycinnamate, tyrphostin A25, tyrphostin B46, herbimycin A and genistein (all obtained from Calbiochem, LaJolla, Calif.) and D,L-threo-sphingosine, staurosporine and H7 (all obtained from Sigma) were prepared in DMSO at appropriate concentrations. Neomycin sulfate (Calbiochem) was dissolved in sterile, deionized water. Control experiments with DMSO solutions showed that DMSO had no effect on P-glycoprotein function or expression. Different concentrations of TPA were used for the treatment of different cell lines, depending on the observed cytotoxicity. PBL were treated with 1 ng/mL TPA; H9 and K562 cells with 10 ng/mL TPA; KG1a and KG1 cells with 100 ng/mL TPA and the other cell lines with 10 ng/mL TPA. Similarly, different concentrations of DOG were used for different cell lines. Thus, PBL were treated with 75 $\mu$M DOG, whereas H9 and K562 cells were treated with two 75 $\mu$M doses of DOG give 2 hr apart. Cells were exposed to TPA or DOG for 8–12 hr before flow cytometric analysis or RNA extraction. Staurosporine (Sigma) was used at 100 nM concentration for KG1a cells and 30 nM for the other cell lines; it was added to the cells 30 minutes prior to the addition of TPA or DOG.

Doxorubicin (Adriamycin), 2-deoxyglucose, nocodazole, pyrrolidone, dithiocarbamate (PDTC), N-tosyl-L-phenylalanine chloromethyl ketone (TPCK; obtained from Sigma); sodium salicylate (obtained from Aldrich Chemical Company); bleomycin (obtained from Invitrogen, San Diego, Calif.) and tricyclodecan-9-yl-xanthogenate potassium (D609) were dissolved in deionized water. A23187, U73122 (obtained from LC Laboratories, Woburn, Mass.), BAPTA/AM, calmidazolium chloride, thapsigargin (obtained from Calbiochem, La Jolla, Calif.) and aspirin (Sigma) were reconstituted in dimethyl sulfoxide. Each of these compounds was dissolved from 100–1000× stock solutions immediately prior to each experiment.

1.2. Flow Cytometric Assays

P-glycoprotein activity was assayed by the rhodamine 123 (Rh123) accumulation assay. For this assay, drug-treated or untreated cells were washed three times and incubated for 1.5–2 hours at 37° C. in media containing 100 ng/mL Rh123 (Sigma). Cells were then washed, stained with propidium iodide (PI) and kept on ice until analysis. Cells growing in monolayer were suspended with 20 mM ethylenediaminetetraacetic acid (Sigma) in phosphate buffered saline (PBS) at pH 7.4 and washed three times prior to Rh123 staining. In some experiments a Rh123 efflux assay (Chaudhary and Roninson, 1991, *Cell* 66: 85–94) was used instead of Rh123 accumulation.

P-glycoprotein expression on the cell surface was analyzed using a P-glycoprotein-specific mouse IgG2a monoclonal antibody (mAb), UIC2 (Mechetner and Roninson, 1992, *Proc. Natl. Acad. Sci. USA* 89: 5824–5828). Mouse IgG2a isotype control antibody was obtained from Sigma. For staining of PBL with UIC2 mAb or isotype control, $10^6$ cells were stained at 4° C. with 10 μg of the antibody for 30 minutes and, after two washes, stained for 30 minutes with 10 μg of FITC-conjugated goat anti-mouse IgG2a antibody (Fisher Scientific, Fairlawn, N.J.), diluted 1:2 with PBS plus 2% FCS. Cells were then washed twice with ice-cold PBS plus 2% FCS, stained with PI and kept on ice until analysis. Essentially the same protocol was used for staining of other cell types except that 2 μg of the secondary antibody were used per $10^6$ cells. In some experiments, phycoerythrine (PE)-conjugated goat anti-mouse IgG2a was used as the secondary antibody; no PI was added in such cases. Flow cytometric analysis was conducted on a Coulter Epics 753 Flow Cytometer.

1.3 RNA Extraction and cDNA-PCR Analysis

RNA was extracted from approximately $10^6$ cells by a small-scale sodium dodecyl sulfate extraction procedure (Peppel and Baglioni, 1990, *BioTechniques* 9: 711–713). In the alternative, RNA was isolated from cells using the TRIzol method (commercially available from GIBCO/BRL). cDNA synthesis and polymerase chain reaction (PCR) amplification of MDR1 and $\beta_2$-microglobulin cDNA sequences were carried out essentially as described (Noonan et al., 1990, *Proc. Natl. Acad. Sci. USA* 87: 7160–7164; Noonan and Roninson, 1991, in Roninson (ed.), *Molecular and Cellular Biology of Multidrug Resistance in Tumor Cells*, Plenum Press, New York, pp. 319–333). Briefly, cDNA was prepared using the method of Krug and Berger (1987, *Meth. Enzymol.* 152: 316–324), with the modification that random hexamers were substituted for oligo(dT) as primers for cDNA synthesis. (Commercially-available kits (for example, from GIBCO/BRL, Gaithersburg, Md.) can be advantageously modified for making cDNA using random hexamers.) PCR is then performed using the following primers:

| | | |
|---|---|---|
| $\beta_2$M (sense) | 5'-ACCCCCACTGAAAAAGATGA-3' | (SEQ ID No.: 1) |
| $\beta_2$M (antisense) | 5'-ATCTTCAAACCTCCATGATG-3' | (SEQ ID No.: 2) |
| MDR1 (sense) | 5'-CCCATCATTGCAATAGCAGG-3' | (SEQ ID No.: 3) |
| MDR1 (antisense) | 5'-GTTCAAACTTCTGCTCCTGA-3' | (SEQ ID No.: 4) |

(where $\beta_2$M represents $\beta_2$microglobulin). PCR was performed for $\beta_2$M experiments under a regime consisting of 1 cycle comprising denaturation at 94° C. for 3 minutes, primer annealing at 60° C. for 30 seconds, and primer extension at 72° C. for 1 minute, followed by 19 cycles comprising denaturation at 94° C. for 30 seconds, primer annealing at 60° C. for 30 seconds, and primer extension at 72° C. for 1 minute, followed by a final cycle comprising denaturation at 94° C. for 30 seconds, primer annealing at 60° C. for 30 seconds, and primer extension at 72° C. for 5 minutes. MDR1 cDNA sequences were amplified using the identical protocol as for $\beta_2$M, but extending the amplification from 19 cycles to 25 cycles. In addition, the cDNA-PCR amplification protocol contained the following modifications: (i) Taq DNA polymerase was added to the PCR mixtures after initial heating of the samples to 94° C. (ii) The yield of the $\beta_2$-microglobulin-specific band, obtained after 22–28 cycles of PCR, was used as the primary criterion for equalizing the starting amounts of the cDNA templates in different preparations, in order to account for differential RNA degradation in cells subjected to different types of treatment. $^{32}$P-labeled PCR products were detected by autoradiography.

EXAMPLE 2

Functional Assays of P-Glycoprotein Expression in Cells Treated with Lymphoid Cell Differentiation Inducing Agents A functional assay was used to detect changes in P-glycoprotein activity in human PBL treated with different agents that induce lymphoid differentiation or activation, based on flow cytometric analysis of cellular accumulation of Rh123, which is a P-glycoprotein-transported fluorescent mitochondrial dye. In this assay, cells expressing little or no P-glycoprotein stain brightly with Rh123, whereas cells with higher levels of P-glycoprotein activity appear Rh123-dull. No apparent effects on P-glycoprotein were observed in cells treated with calcium ionophore A23187, IL-1α or IL-2. In contrast, treatment of PBL with the phorbol ester TPA caused a significant increase in the number of Rh123-dull cells. The increase in the Rh123-dull population could be prevented by the addition of 30 μM verapamil, a P-glycoprotein inhibitor. Since the best-known cellular effect of TPA is the stimulation of PKC, DOG (a cell-permeable diacylglycerol and a physiological stimulant of PKC) was also tested to determine its effects on Rh123 accumulation in PBL. Treatment of PBL with DOG was found to decrease Rh123 accumulation by PBL.

To determine if the observed effect of PKC stimulants on P-glycoprotein activity was due to an increase in P-glycoprotein expression, untreated and TPA-treated PBL were stained by indirect immunofluorescence labeling with mAb UIC2 that recognized an extracellular epitope of P-glycoprotein encoded by the human MDR1 gene. TPA treatment markedly increased the levels of P-glycoprotein on the cell surface. The increase in P-glycoprotein was accompanied by a corresponding increase in MDR1 mRNA levels in the total population of TPA-treated PBL, as detected by polymerase chain reaction (PCR) amplification of MDR1 cDNA sequence. Thus, the TPA-induced increase in P-glycoprotein activity was due at least in part to the activation of MDR1 gene expression at the mRNA and protein levels.

Since PBL comprise a heterogeneous population of many different subtypes, a series of leukemia-derived clonal cells lines were tested for changes in P-glycoprotein expression after treatment with TPA. As summarized in Table I, all the cell lines that were positive for P-glycoprotein prior to TPA treatment showed a large increase in their P-glycoprotein expression after exposure to TPA. This group included human KG1 and KG1a (stem-cell like leukemia cell lines), whose relatively high level of P-glycoprotein was likely to reflect the expression of this protein in normal hematopoietic stem cells (Chaudhary and Roninson, ibid.), as well as murine E14 thymoma and LBRM 33 lymphoma cell lines.

Figure 2:
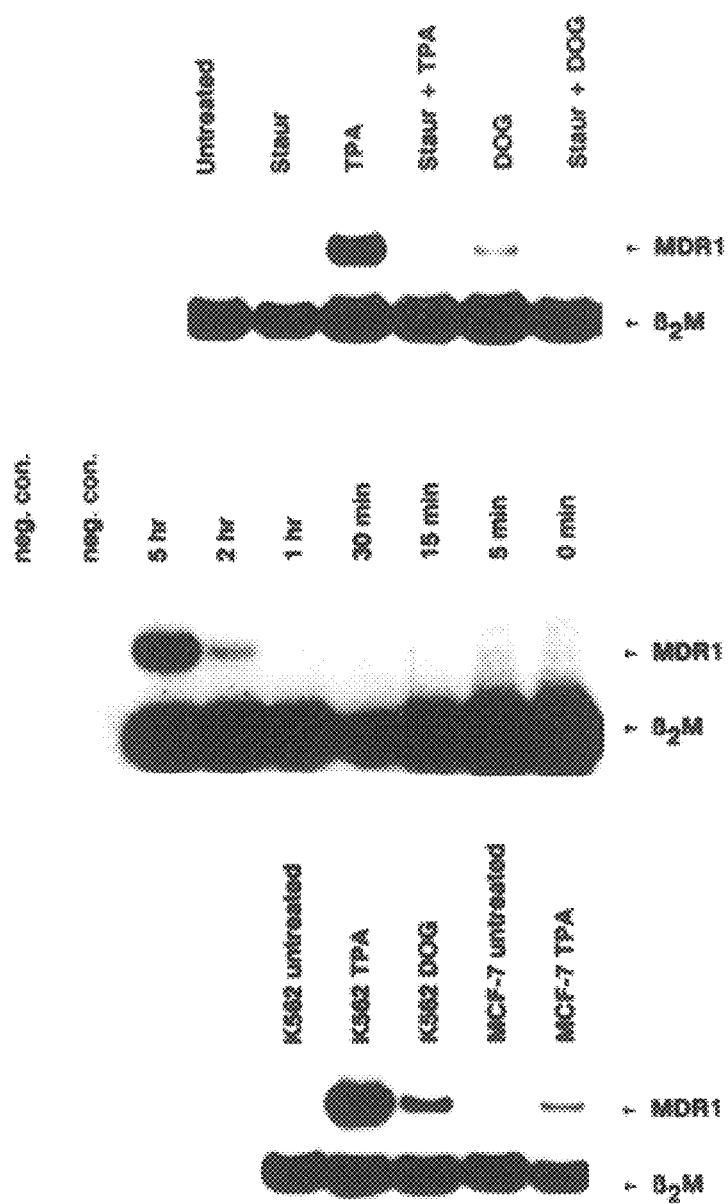
FIG. 2. cDNA-PCR analysis of the effects of TPA, DOG and staurosporine on MDR1 mRNA expression in different cell lines. In each lane, the upper band (167 bp) corresponds to MDR1, and the lower band (120 bp) to $\beta_2$-microglobulin specific PCR products.

Among the cell lines that expressed no detectable P-glycoprotein, H9 and K562 leukemia cell lines showed clear-cut induction of MDR1 mRNA and P-glycoprotein by either TPA or DOG. Flow cytometric assays showed that the treatment of these cell lines with TPA or DOG resulted in the appearance of a major cell population that expressed P-glycoprotein (FIGS. 1A through 1E). These changes were paralleled by an increase in steady-state levels of MDR1 mRNA in TPA- or DOG-treated cells (FIGS. 2A and 2B). As shown in FIG. 2B, MDR1 mRNA became detectable in H9 cells 2 hrs after the addition of TPA and continued to increase until at least 5 hr, indicating a rapid response to TPA, consistent with transcriptional activation of MDR1 by TPA in these cells.

The increase of MDR1 expression after TPA treatment was not limited to hematopoietic cells, but was also observed in some solid tumor-derived cell lines, including EJ bladder carcinoma cells that expressed a low level of P-glycoprotein, and MCF-7 breast carcinoma cells where MDR1 expression was undetectable without TPA treatment (FIG. 2C). As summarized in Table I, most of the tested P-glycoprotein negative cell lines were only treated with a fixed concentration (20 ng/mL) of TPA, and were not tested for their ability to respond to higher TPA concentrations.

In an attempt to interfere with the induction of MDR1 gene expression by PKC agonists, a potent protein kinase inhibitor, staurosporine, was used to treat various cell lines. Unexpectedly, staurosporine alone caused a significant increase in P-glycoprotein expression in the cell lines that were already positive for P-glycoprotein (KG1, KG1a, mouse EL4 and LBRM 33 cell lines). Two additional compounds, cyclosporine A and verapamil, which are known to be P-glycoprotein inhibitors as well as inhibitors of PKC, have also been found to increase P-glycoprotein expression and/or dye efflux in KG1 and EL4 cells. The effect of PKC inhibitors on P-glycoprotein expression in the P-glycoprotein-positive cell lines made it difficult to analyze the interactions between staurosporine and PKC agonists in such cells.

TABLE I

EFFECT OF TPA ON MDR1 EXPRESSION

| Cell Line | Untreated | TPA-Treated | Assays |
|---|---|---|---|
| Normal Cells | | | |
| PBL | + | ++ | F,A,R |
| Human Hematopoietic Cell Lines | | | |
| KG1 (acute myelogenous leukemia) | ++ | +++ | F,A |
| KG1a (acute myelogenous leukemia) | ++ | +++ | F,A |
| K562 (chronic myelogenous leukemia) | − | ++ | F,A,R |
| H9 (T-cell leukemia) | − | ++ | F,A,R |
| HL-60 (promyelocytic leukemia) | − | − | F |
| THP-1 (promyelocytic leukemia) | − | − | F |
| Jurkat, clone E6-1 (T-cell leukemia) | − | − | F |
| Molt-4 (T-cell leukemia) | − | − | F |
| U937 (histiocytic leukemia) | − | − | F |
| Mouse Hematopoietic Cell Lines | | | |
| EM (thymoma) | ++ | +++ | F |
| LBRM 33, clone 4A2 (lymphoma) | + | ++ | F |
| Human Solid Tumor Cell Lines | | | |
| EJ (bladder carcinoma) | + | ++ | F |
| MCP-7 (breast carcinoma) | − | + | R |
| HeLa (cervical carcinoma) | − | − | F,R |
| KB-3-1 (HeLa subline) | − | − | F,R |
| HT 1080 (fibrosarcoma) | − | − | F,R |

MDR1 gene expression was evaluated by a functional assay for Rh123 accumulation (F), UIC2 antibody staining (A) or cDNA-PCR assay for MDR1 mRNA (R), and expressed as relative values. Cells were considered negative if they expressed no P-glycoprotein detectable by the Rh123 or UIC2 staining assays and had MDR1 mRNA level no higher than that of KB-3-1 cells.

However, staurosporine did not induce MDR1 expression in P-glycoprotein-negative H9 cells. The addition of staurosporine to H9 cells 30 minutes prior to TPA or DOG treatment completely abolished MDR1 induction by these agents, as evidenced by flow cytometric (FIGS. 1A through 1E) and cDNA-PCR assays (FIG. 2A). Staurosporine also inhibited the effects of TPA and DOG in normal PBL.

EXAMPLE 3

Protein Kinase Inhibitors Prevent Cytotoxic Drug-mediated MDR1 Induction in Tumor Cells 1. Materials and Methods 1.1 Flow Cytometric Assays K562 cells were stained for 10 minutes at 37° C. with 100 ng/mL Rh123 or with 10 ng/mL of $DiOC_2(3)$, another P-glycoprotein-transported dye (Chaudhary and Roninson, ibid.), in 5 mL of DMEM supplemented with 10% fetal calf serum. After two washes, the cells were allowed to efflux the dye for 3 hrs (for Rh123) or 2 hrs (for $DiOC_2(3)$) at 37° C. in 5 mL of dye-free media, as previously described (Chaudhary and Roninson, ibid.). In double-labeling experiments, 3 ng/mL of $DiOC_2(3)$ in 5 mL of media were used for staining. Each efflux assay was carried out in the presence and in the absence of 30 $\mu$M verapamil. KG1 cells were stained with 100 ng/mL Rh123 in 5 mL of media for 3 hours at 37° C. and analyzed without efflux. Indirect immunofluorescence labeling (as described in Chaudhary and Roninson, ibid.) was carried out using 2 $\mu$g of the primary antibody (UIC2 or mouse IgG2a isotype control from Sigma) and 10 $\mu$g of the secondary antibody (PE-conjugated $F(ab')_2$ fragments of sheep anti-mouse IgG (Sigma)) per $2 \times 10^5$ KG1 cells. Flow cytometric analysis and flow sorting were carried out as described (Chaudhary and Roninson, ibid.); nonviable cells were excluded from analysis on the basis of abnormal size or granularity or, in experiments not utilizing phycoerythrine, by accumulation of propidium iodide.

1.2. Growth Inhibition Assays

Cells were plated in duplicate in 96-well microtiter plates at 3,000 cells per well, and allowed to grow in increasing concentrations of different drugs. Cell growth after 7–10 days was analyzed by MTT assay (Pauwels et al., 1988, *J. Virol. Meth.* 20: 309–321).

1.3. MDR1 Induction Inhibition Assays using PKC Inhibitors

Cells were plated in 6-well Falcon tissue culture plates at 3,300 cells per well, and incubated in the appropriate concentrations of drugs. Each of the protein kinase inhibitors to be tested were added at the appropriate final concentration 45 minutes prior to MDR1 induction by the addition of Ara-C or TPA, with the exception of herbimycin A, which was added 12 hours prior to Ara-C or TPA, and tyrphostins A25 and B46, which were each added 16 hours prior to MDR1 induction by the addition of Ara-C or TPA. Cells were incubated overnight (TPA) or for 10 hours (Ara-C) at 37° C./ 5% $CO_2$ after the addition of the MDR1 inducing agents before harvesting for cDNA-PCR analysis.

In addition, the analysis of certain drugs imposed added requirements. For experiments using calphostin C, cells were incubated under direct white light illumination. For experiments using D,L-threo-sphingosine, the cell culture medium was pre-treated with the appropriate concentration of the drug for one hour at 37° C. with continuous gentle mixing. After this pretreatment, cells were resuspended in media supplemented with drug and incubated for 45 minutes as described above.

After the completion of the incubation period, each culture was treated with 25 µM Ara-C and incubated for an additional 10 hours. Alternatively, each culture was treated with 16 nM (10 ng/mL) TPA and incubated for 12 hours or overnight.

cDNA-PCR analyses on each culture treated with drugs, or in control cultures incubated in the absence or presence of Ara-C or TPA alone, were performed as described in Example 1 above.

EXAMPLE 4

Figure 3A:
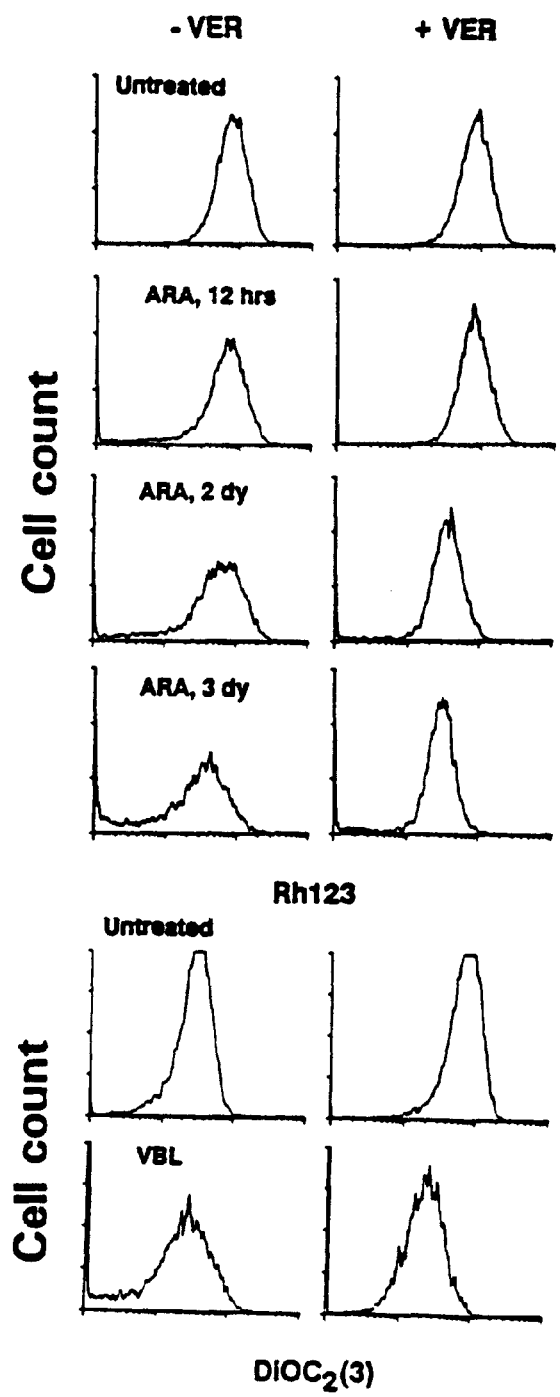
FIG. 3A. Efflux of P-glycoprotein-transported fluorescent dyes from K562 cells in the absence (left) or in the presence (right) of 30 $\mu$M verapamil (VER). Top panel: Rh123 efflux from untreated cells (−) and from cells treated with 50 $\mu$M Ara-C (ARA) for 12 hours or with 10 $\mu$M Ara-C for 2 to 3 days. Bottom panel: DiOC$_2$(3) efflux from untreated cells and from cells treated with 1 $\mu$g/mL vinblastine (VBL) for 36 hrs.
Figure 3B:
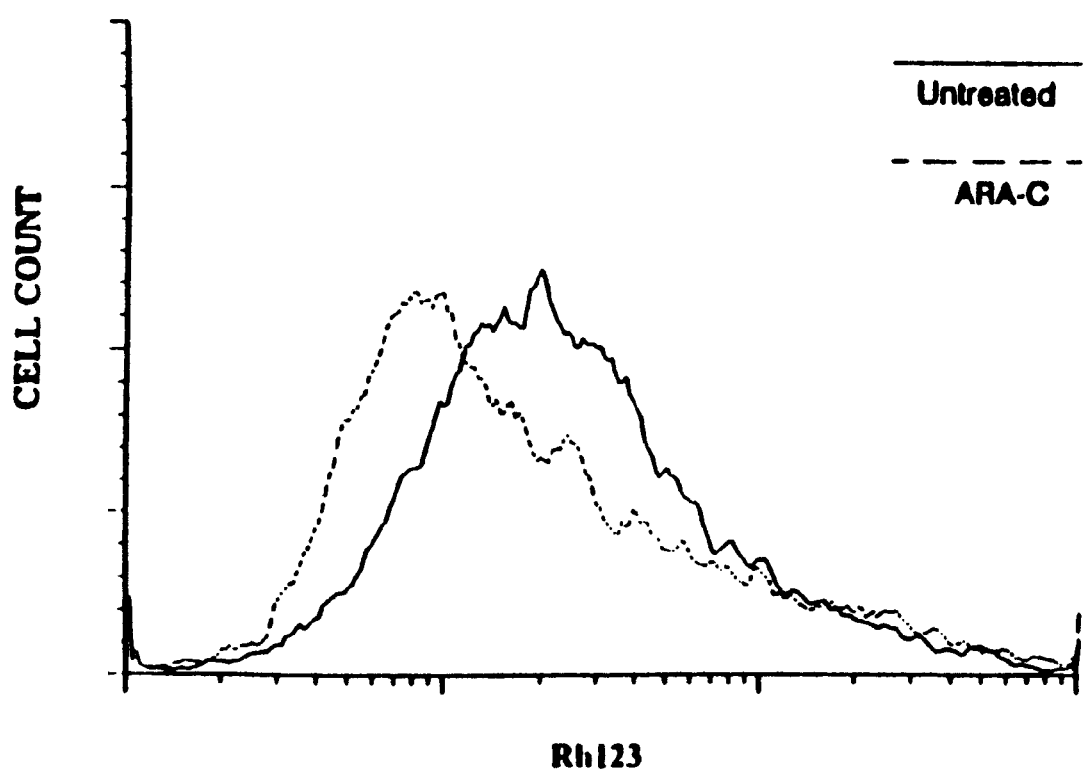
FIG. 3B. Increased P-glycoprotein expression of Ara-C treated KG1 leukemia cells. Left: Rh123 accumulation in untreated cells or cells treated with 10 $\mu$M Ara-C for 1.5 days. Right: indirect immunofluorescence labeling of the same cells with anti-P-glycoprotein UIC2 antibody or IgG2a isotype control.
Figure 4A:
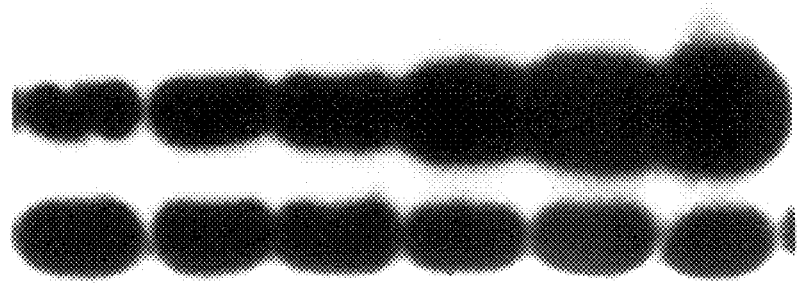
FIG. 4A. MDR1 induction in K562 cells by Ara-C. Cells were exposed to the indicated concentrations of Ara-C for 4.5 days. Cell growth relative to untreated cells was determined by the MTT assay in parallel with RNA extraction.

Functional Assays of P-Glycoprotein Expression in Cells Treated with Protein Kinase Activators and Inhibitors The studies described in Examples 1 and 2, above, demonstrate that PKC agonists can induce MDR1 expression, suggesting an important role in PKC in the activation of the multidrug resistance response in tumor cells. PKC has also been implicated in cellular responses to different types of cytotoxic stress (Papathanasiou and Fornace, 1991, in R. F. Ozols (ed.), *Molecular and Clinical Advances in Anticancer Drug Resistance*, Kluwer Academic Publishers, Boston, Mass., pp. 13–36). In particular PKC is activated by treatment with Ara-C. Therefore, experiments were performed to test whether Ara-C, which is not transported by P-glycoprotein, would have any effect on P-glycoprotein function in K562 leukemia cells. As illustrated in FIG. 3A, exposure to K562 cells to Ara-C for 12–72 hours led to the emergence of a subpopulation of 3–17% cells that effluxed Rh123. Rh123 efflux was sensitive to the P-glycoprotein inhibitor verapamil. The appearance of Rh123-dull cells was paralleled by a dose-dependent increase in MDR1 mRNA expression relative to $\beta_2$-glycoprotein in Ara-C treated K562 cells, as detected by polymerase chain reaction amplification of cDNA sequences (FIG. 4A).

A number of other chemotherapeutic drugs were also tested for their ability to induce MDR1 expression in K562 cells. Adriamycin, daunorubicin, vinblastine, cisplatin and hydroxyurea were all found to induce MDR1 mRNA expression (FIG. 4B) and Rh123 or $DiOC_2(3)$ efflux by 3–10% of the treated cells (FIG. 3A). Only the first four of these drugs are transported by P-glycoprotein (Roninson, ibid.). This result, together with the short times of drug exposure required for MDR1 induction, indicates that cytotoxic selection for MDR1-expressing cells was not responsible for the emergence of the P-glycoprotein-positive subpopulations.

Figure 4C:
FIG. 4C. MDR1 induction in KB-3-1 carcinoma cells, untreated or treated for 2 days with 200 ng/mL Adriamycin or 10 $\mu$M Ara-C.
Figure 4D:
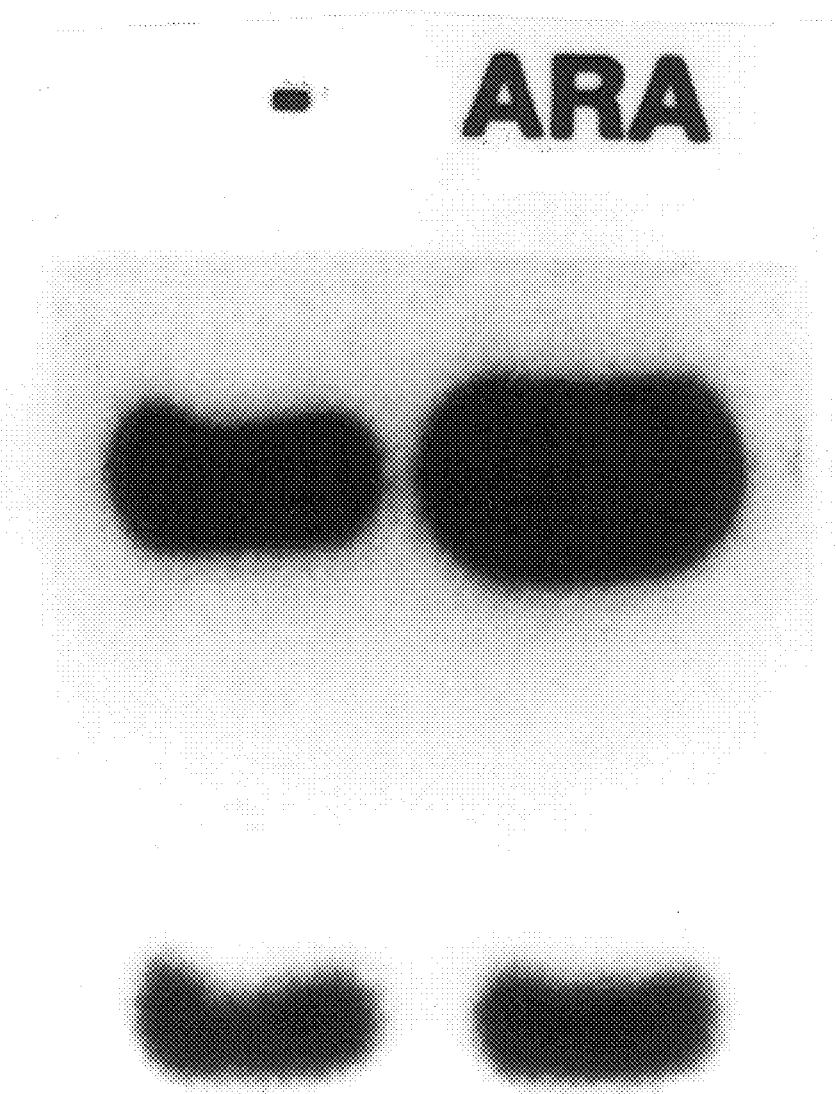
FIG. 4D. MDR1 induction in EJ carcinoma cells, untreated (−) or treated for 4 days with 10 $\mu$M Ara-C.

The ability of cytotoxic drugs to induce MDR1 expression was not limited to K562 cells. Ara-C increased P-glycoprotein expression in KG1 leukemia cells, which contained a significant amount of P-glycoprotein prior to drug treatment, as detected by Rh123 accumulation or immunoreactivity with monoclonal antibody UIC2 (FIG. 3A). Ara-C also activated MDR1 mRNA expression in H9 T-cell leukemia (FIGS. 5A through 5C), KB-3-1 epidermoid carcinoma (FIG. 4C), and EJ bladder carcinoma (FIG. 4D), though the magnitude of induction was somewhat lower in carcinoma cell lines. In addition, MDR1 mRNA expression was induced in H9 cells by treatment with Adriamycin, vinblastine and methotrexate (FIGS. 5A through 5C), and in KB-3-1 cells with Adriamycin (FIG. 4C). However, P-glycoprotein induction was not detected in HL60 leukemia cells treated with these drugs. In all cases, MDR1 induction became detectable at the same time as visible cell damage, which was evidenced by cell swelling, increased granularity, altered cell shape, and growth inhibition (FIG. 4A). In addition, continuous passage of some cell lines in the absence of drugs for several months also led to a small increase in MDR1 expression, accounting for the variability in the basal levels of MDR1 mRNA in untreated cells.

Figure 3C:
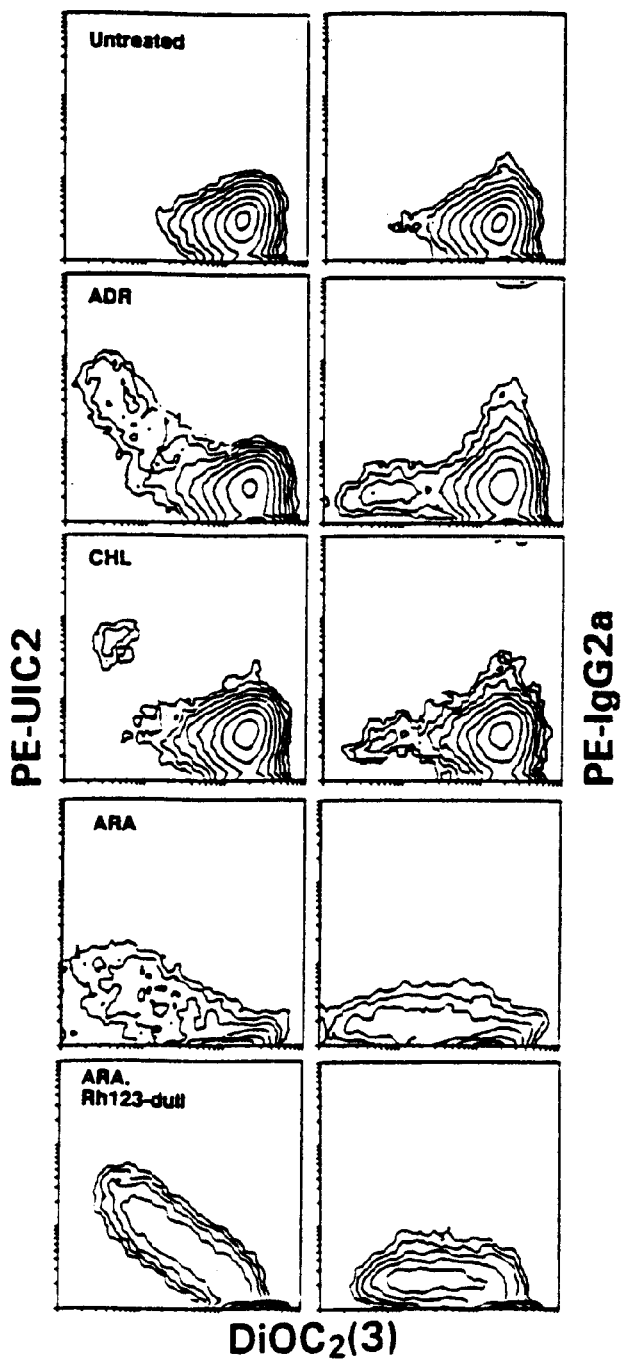
FIG. 3C. Contour density maps of K562 cells maintained in drug-free media after exposure to different drugs and analyzed by double labeling using DiOC$_2$(3) (horizontal axis) and UIC2 antibody (left) or IgG2a isotype control (right) indirectly labeled with phycoerythrine (PE) (vertical axis). Top to bottom: untreated cells, cells treated with 60 ng/mL Adriamycin for 3 days and grown without drug for 5 weeks, cells treated with 30 $\mu$M chlorambucil (CHL) for 5 days and grown without drug for 2 weeks, cells treated with 10 $\mu$M Ara-C for 3 days and grown without drug for 5 weeks (this experiment utilized one-half the amount of the secondary antibody used in the other assays); Rh123-dull population of cells treated with Ara-C as above and isolated by fluorescence-activated cell sorting six weeks after removal from the drug.
Figure 3D:
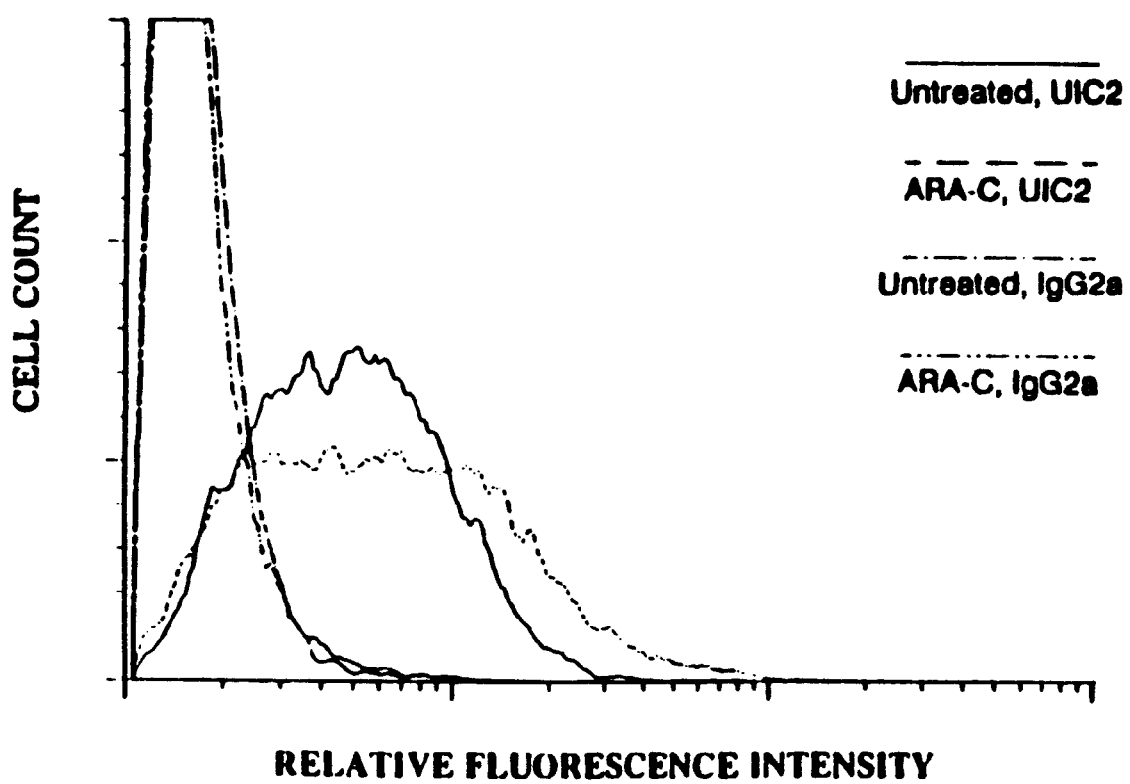
FIG. 3. Flow cytometric analysis of drug-induced MDR1 expression.
Figure 4E:
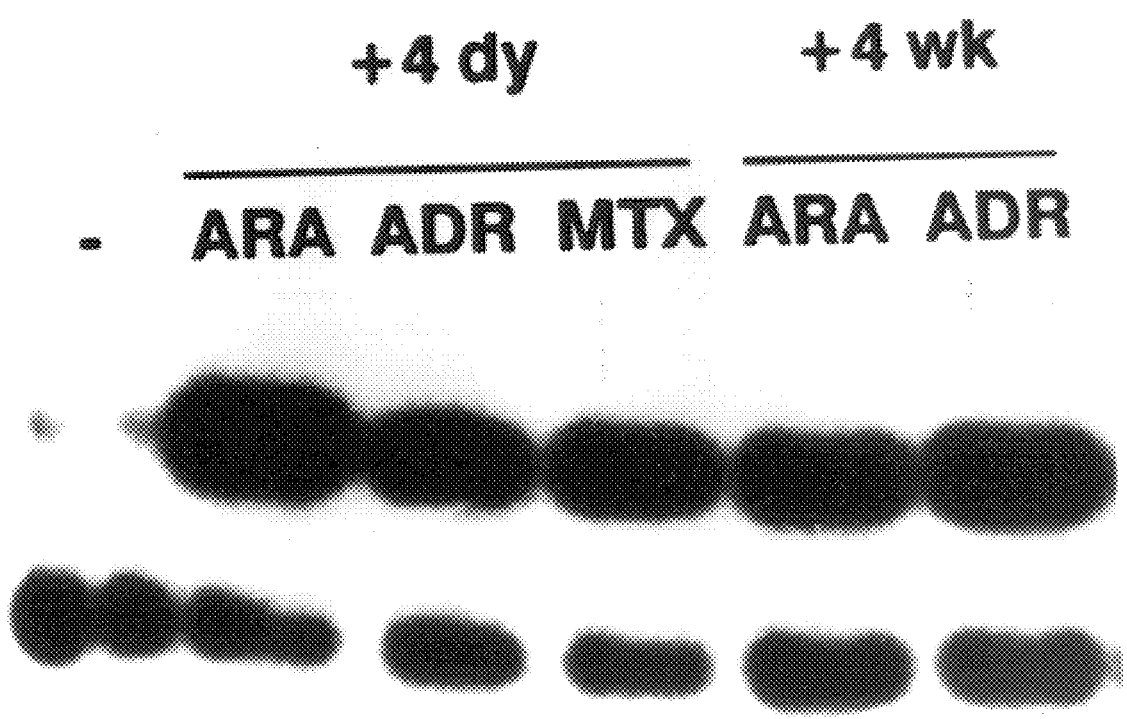
FIG. 4E. Maintenance of drug induced MDR1 expression in K562 cells. Cells were treated for 3 days with 60 ng/mL Adriamycin, 10 $\mu$M Ara-C or 200 ng/mL methotrexate and cultured in drug-free medium for the indicated period of time.
Figure 6A:
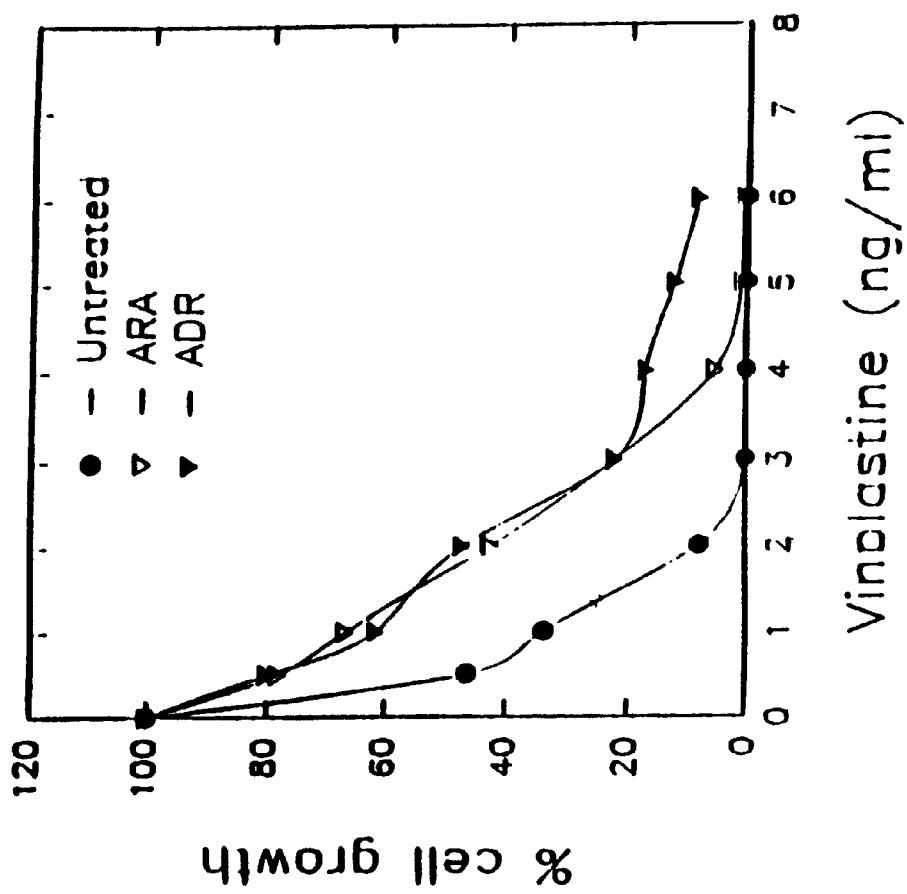
FIG. 6A. Growth inhibition by vinblastine in untreated and Ara-C (ARA)- or Adriamycin (ADR)-treated cells. Cells were treated as in FIG. 3C and grown in the absence of drugs for six weeks. Vinblastine inhibition assay was carried out for 10 days.
Figure 6B:
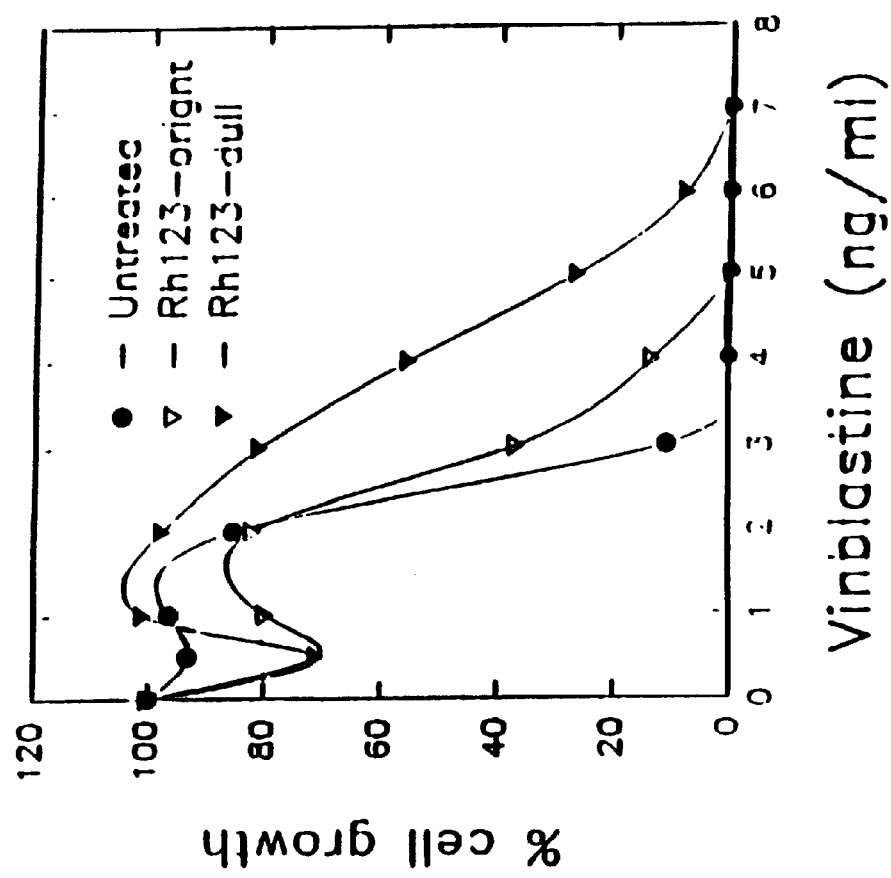
FIG. 6B. Growth inhibition by vinblastine in untreated cells and Rh123-dull and Rh123-bright populations of Ara-C treated cells. Ara-C treated cells, six weeks after removal from the drug, were stained by the Rh123 efflux procedure and separated into Rh123-dull and Rh-123 bright populations by fluorescence-activated cell sorting. The Rh123-dull population was >60% pure (FIG. 3C), and the Rh123-bright population was 90–95% pure. One week after sorting, vinblastine inhibition assay was carried out for 7 days.

Also assayed was whether drug-induced MDR1 expression was maintained after cytotoxic drug treatment. For this purpose, K562 cells were treated with cytotoxic concentrations of Ara-C, Adriamycin, chlorambucil or methotrexate for 3–5 days, and then allowed to grow in the absence of the drugs. At different times, MDR1 expression in the surviving cells was analyzed by dye efflux and immunofluorescence labeling with UIC2 (FIG. 3C) or by cDNA-PCR (FIG. 4E). MDR1 expression in a subpopulation of treated cells was maintained for a least several weeks after the removal of drug (up to 11 weeks in the Ara-C treated population). P-glycoprotein-positive K562 cells showed no significant changes in their size, granularity and expression of differentiation-related antigenic markers. The presence of multidrug-resistant cells six weeks after the removal of Ara-C or Adriamycin was also demonstrated by a growth inhibition assay with vinblastine, a P-glycoprotein substrate. Vinblastine resistance, characterized by approximately 2–3 fold increase in the $ID_{10}$ value, was specifically associated with the Rh123-dull subpopulation of cells (FIGS. 6A and 6B). Thus, drug treatment leads to sustained induction of MDR1 expression and its associated drug resistance in a subpopulation of treated cells. It was also found that Ara-C and Adriamycin-treated K562 cells were more resistant than the untreated cells to the cytotoxic effect of chlorambucil, a chemotherapeutic alkylating agent which is not transported by P-glycoprotein. This result indicates that other pathways or mechanism of clinically relevant drug resistance are co-induced with MDR1 expression after treatment with chemotherapeutic drugs.

Figure 5A:
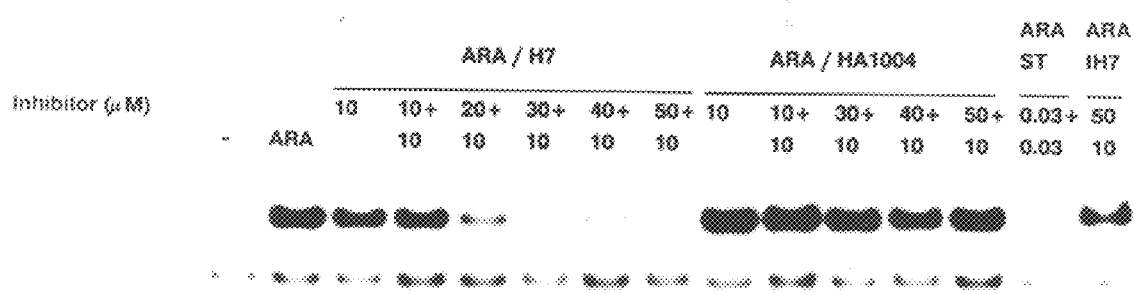
FIG. 5A. H9 cells, untreated or treated with 50 μM Ara-C for 22 hr. The inhibitors were added at the indicated concentrations at the beginning of the experiment and 16 hr. later.
Figure 5B:
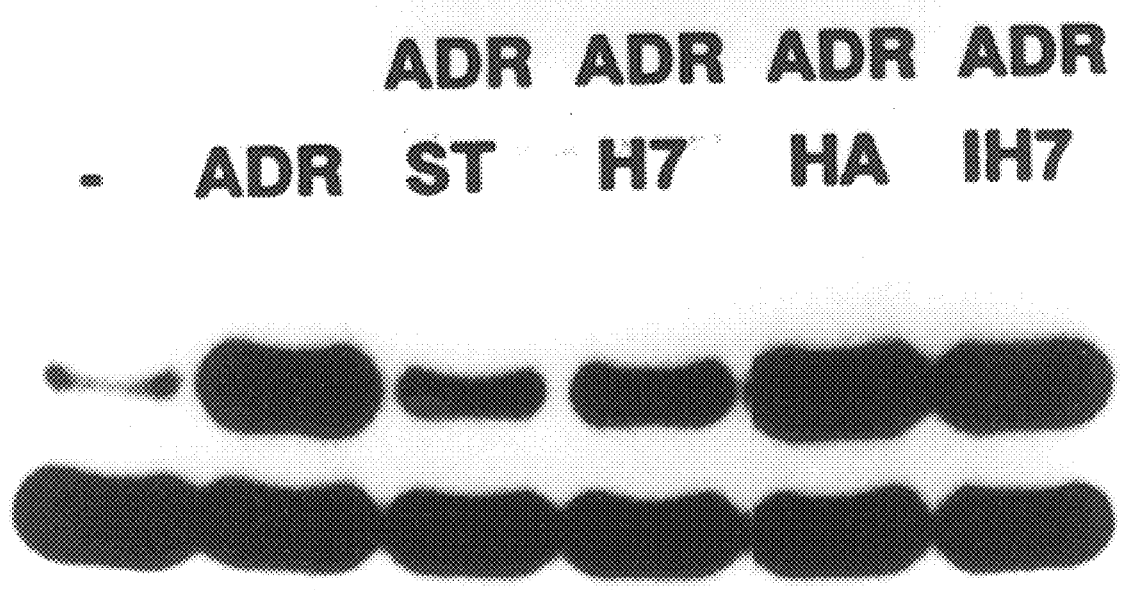
FIG. 5B. H9 cells, untreated or treated with 200 ng/mL Adriamycin for 22 hrs. Equal amounts of inhibitors (0.03 μM staurosporine, 10 μM H7, HA-1004 and Iso-H7) were added at the beginning of the experiment and 16 hrs later.
Figure 5C:
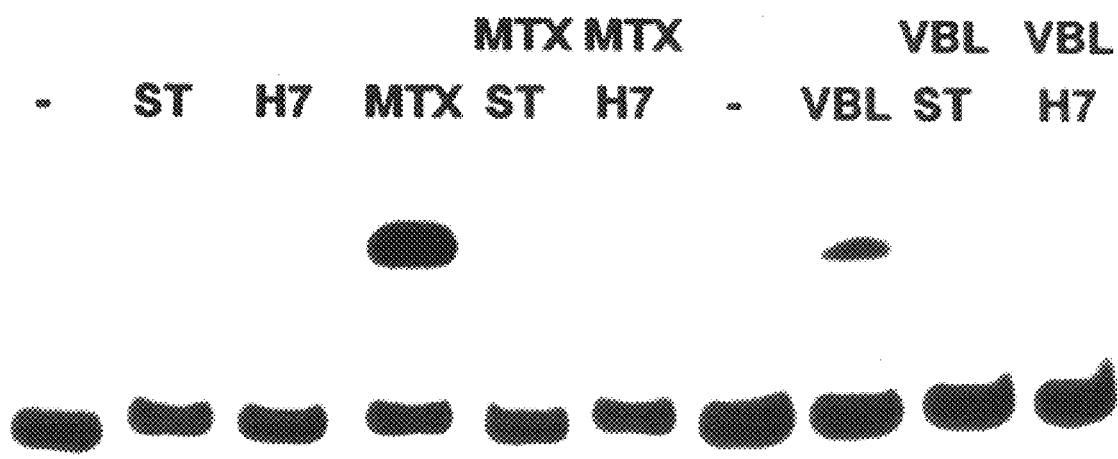
FIG. 5C. H9 cells, untreated or treated with 40 ng/mL vinblastine or 200 ng/mL methotrexate for 36 hours. Equal amounts of inhibitors (0.1 μM staurosporine, 50 μM H7) were added at the beginning of the experiment and 24 hrs later.

To demonstrate that PKC was involved in MDR1 induction by cytotoxic drugs, a variety of PKC inhibitors were used to block MDR1 mRNA induction in H9 cells. The addition of certain these compounds effectively blocked MDR1 induction by Ara-C, Adriamycin, methotrexate and vinblastine, as detected by cDNA-PCR (FIGS. 5A through 5C) and dye efflux assays with Ara-C treated cells. To investigate the specificity of the observed inhibition for PKC, effects of increasing doses of H7 ($IC_{50}$=6.0 μM for PKC, 3.0 μM for protein kinase A) and HA1004, a non-PKC specific protein kinase inhibitor ($IC_{50}$=40 μM for PKC, 2.3 μM for protein kinase A) (Hidaka et al., 1984, *Biochemistry* 23: 5036–5041) were compared. As shown in FIG. 5A, H7 inhibited MDR1 induction by Ara-C at 10 μM or higher concentration, but HA1004 showed no significant inhibition even at 60 μM. These results were consistent with a role for PKC in MDR1 induction by cytotoxic drugs.

To further evaluate the capacity of protein kinase inhibitors to suppress MDR1 induction by cytotoxic drugs and PKC agonists, H-9 human T-cell leukemia cells were used in cDNA-PCR assays to examine induced MDR1 mRNA expression levels in the presence of protein kinase inhibitors. The results of these assays are shown in FIGS. 7A through 7F and are summarized in accompanying Table II. MDR1 was induced in cells represented in FIG. 7F by overnight incubation in 10 ng/mL TPA; 10 hour incubation with 25 μM Ara-C was used to induce MDR1 expression in all other cell cultures analyzed as in FIG. 7A through 7E.

Figure 7A:
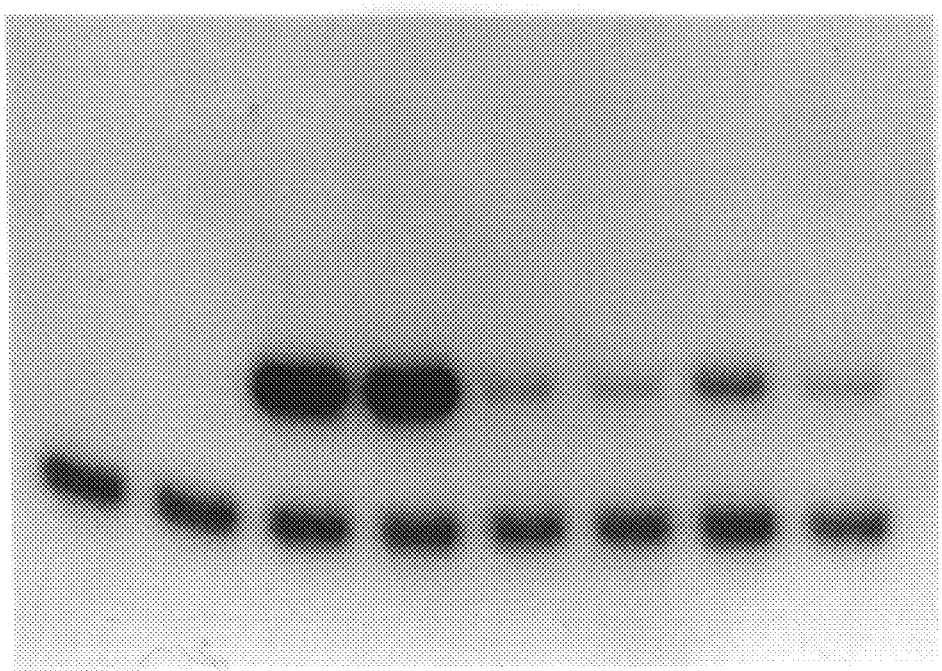
FIG. 7A. Effect of tyrphostins on MDR1 induction in H-9 cells by Ara-C. Cells were incubated for 10 hours with 25 μM Ara-C (Lanes 3 and 4) or with Ara-C and 50 μM tyrphostin A25 (Lanes 5 and 6) or with Ara-C and 50 μM tyrphostin B46 (Lanes 7 and 8). Each of the tyrphostins were added to their respective H-9 cell cultures 16 hours prior to the addition of Ara-C. Negative control lanes (Lanes 1 and 2) represent H-9 cell cultures incubated overnight in the absence of Ara-C and either protein kinase inhibitor.

Two erbstatin analogues (the tyrphostins A25 and B46) were tested for the ability to inhibit Ara-C induced MDR1 mRNA expression, as shown in FIG. 7A. Both of these compounds (tyrphostin A25, Lanes 5 and 6; tyrphostin B46, Lanes 7 and 8) demonstrated the capacity to strongly inhibit Ara-C induced MDR1 expression when incubated with H-9 cells at concentrations of 50–100 μM.

Figure 7B:
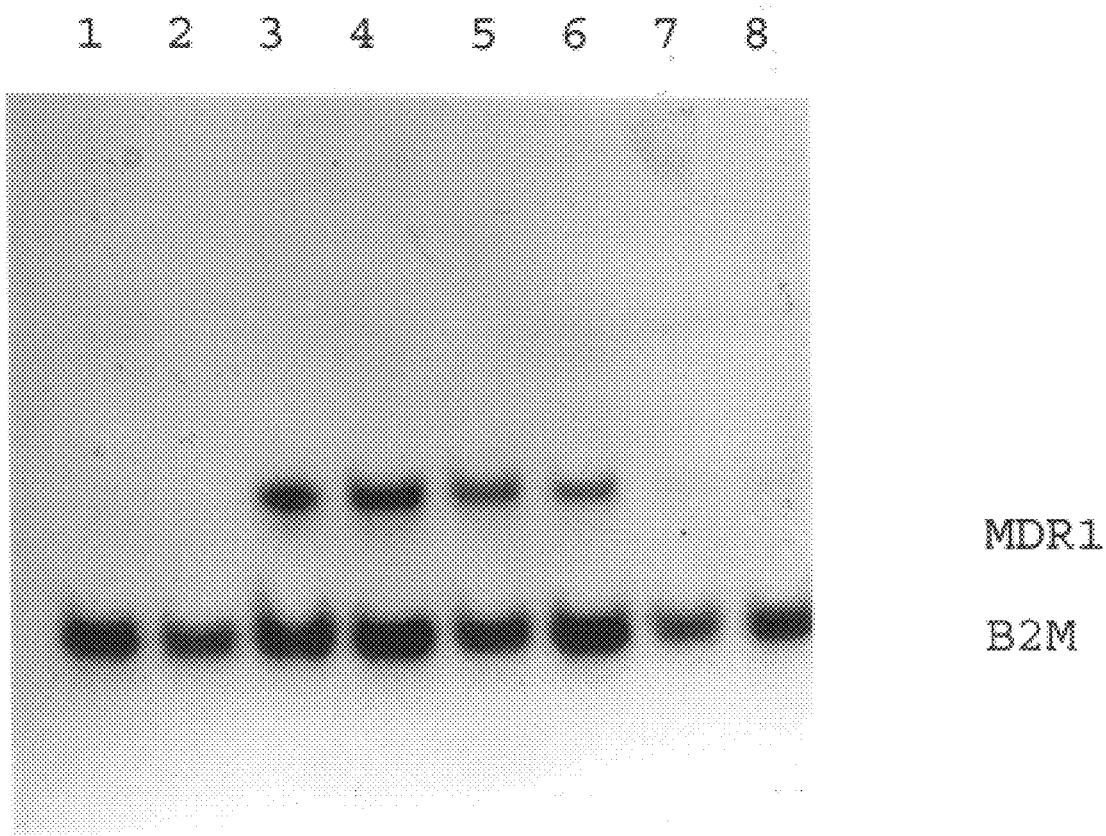
FIG. 7B. Effect of neomycin sulfate on MDR1 induction in H-9 cells by Ara-C. Cells were incubated for 10 hours with 25 μM Ara-C (Lanes 3 and 4) or with Ara-C and 4 mM (Lanes 5 and 6) or 10 mM (Lanes 7 and 8) neomycin sulfate. Neomycin sulfate at each concentration was added to the respective H-9 cell cultures 45 minutes prior to the addition of Ara-C. Negative control lanes (Lanes 1 and 2) represent H-9 cell cultures incubated overnight in the absence of Ara-C and neomycin sulfate.
Figure 7C:
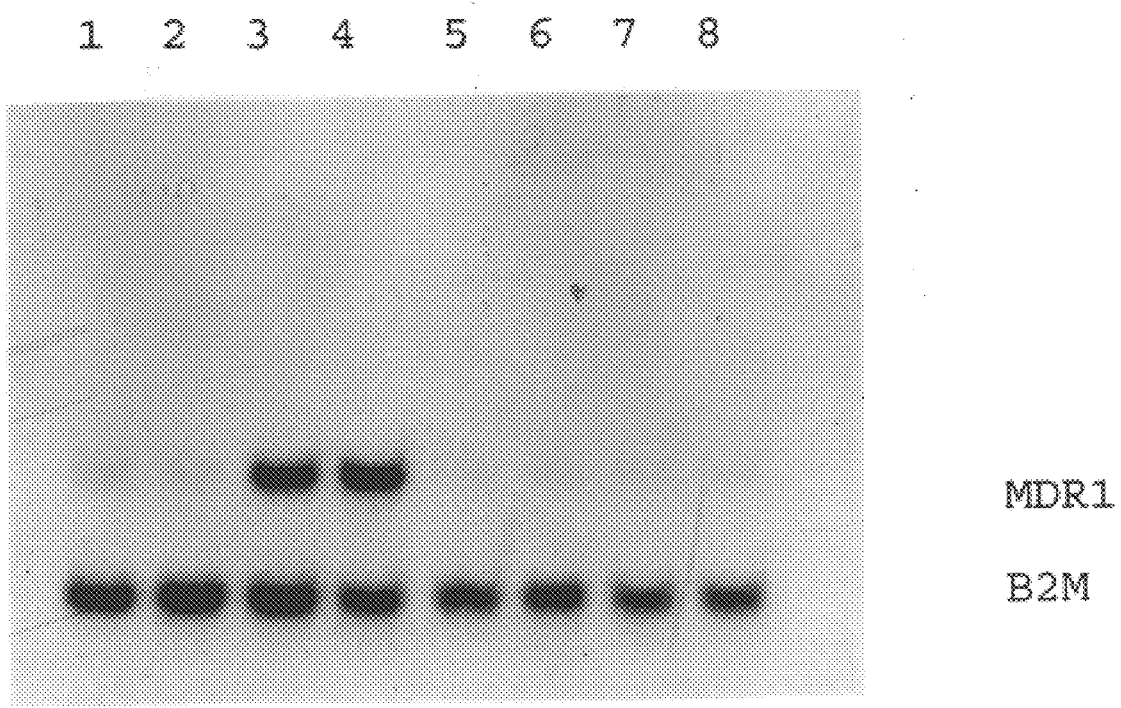
FIG. 7C. Effect of an erbstatin analog on MDR1 induction in H-9 cells by Ara-C. Cells were incubated for 10 hours with 25 μM Ara-C (Lanes 3 and 4) or with Ara-C and the erbstatin analog methyl-2,5-dihydroxycinnamate at a concentration of 32 μM (Lanes 5 and 6) or 64 μM (Lanes 7 and 8). The erbstatin analog at each concentration was added to the respective H-9 cell cultures 45 minutes prior to the addition of Ara-C. Negative control lanes (Lanes 1 and 2) represent H-9 cell cultures incubated overnight in the absence of Ara-C and either protein kinase inhibitor.

The concentration dependence of the ability of the erbstatin analog methyl-2,5-dihydroxycinnamate to inhibit MDR1 expression induced by treatment of H-9 cells with 25 μM Ara-C is shown in FIG. 7C. These results demonstrate that this erbstatin analog inhibits MDR1 expression at both 32 μM and 64 μM to essentially the same degree.

Figure 7D:
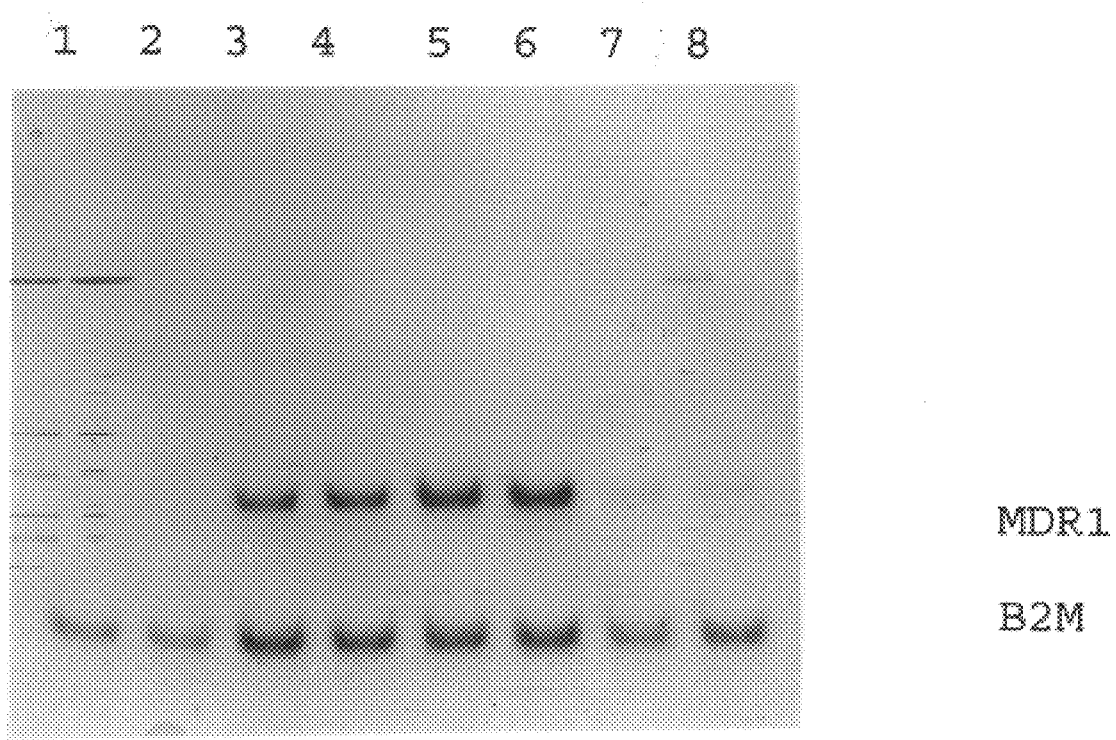
FIG. 7D. Effect of calphostin C on MDR1 induction in H-9 cells by Ara-C. Cells were incubated for 10 hours with 25 μM Ara-C (Lanes 3 and 4) or with Ara-C and calphostin C at a concentration of 0.1 μM (Lanes 5 and 6) or 1 μM (Lanes 7 and 8). Calphostin C at each concentration was added to the respective H-9 cell cultures 45 minutes prior to the addition of Ara-C, and plates were incubated under direct illumination by white light. Negative control lanes (Lanes 1 and 2) represent H-9 cell cultures incubated overnight in the absence of Ara-C and either protein kinase inhibitor.

Inhibition of Ara-C induced MDR1 expression by the combination of calphostin C and direct illumination with white light in shown in FIG. 7D. This compound was found to be capable of inhibiting MDR1 expression when present at concentration of 1 μM (Lanes 7 and 8); the inhibitory capacity of this compound was greatly reduced when the concentration used was reduced to 0.1 μM (Lanes 5 and 6).

Figure 7E:
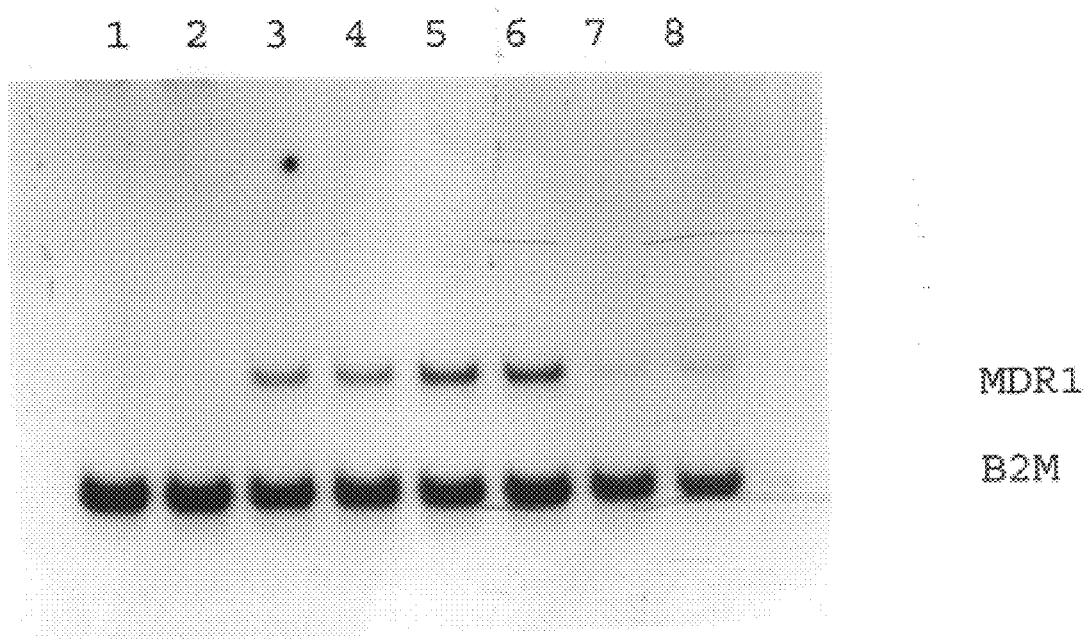
FIG. 7E. Effect of chelerythrine on MDR1 induction in H-9 cells by Ara-C. Cells were incubated for 10 hours with 25 μM Ara-C (Lanes 3 and 4) or with Ara-C and chelerythrine at a concentration of 1 μM (Lanes 5 and 6) or 5 μM (Lanes 7 and 8). Chelerythrine at each concentration was added to the respective H-9 cell cultures 45 minutes prior to the addition of Ara-C. Negative control lanes (Lanes 1 and 2) represent H-9 cell cultures incubated overnight in the absence of Ara-C and either protein kinase inhibitor.

Progressive dose-dependent inhibition of Ara-C induced MDR1 expression was demonstrated for the PKC inhibitor chelerythrine, shown in FIG. 7E. The dose-dependence of inhibition using this compound is seen by a comparison of the intensity of the MDR1-specific band in Lanes 5 and 6 (1 μM chelerythrine) and Lanes 7 and 8 (5 μM chelerythrine).

Figure 7F:
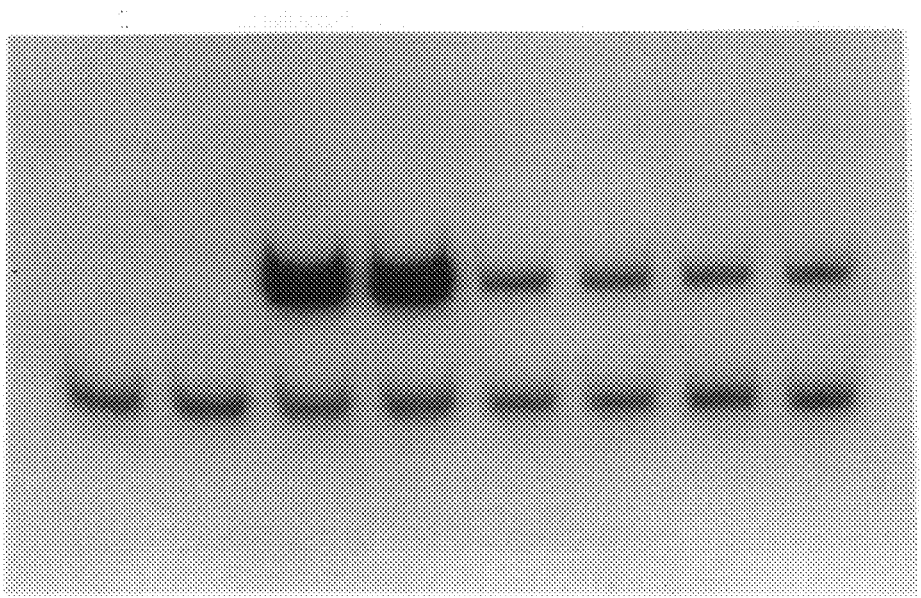
FIG. 7F. Effect of staurosporine and an erbstatin analog on MDR1 induction in H-9 cells by TPA. Cells were incubated overnight with TPA (10 ng/mL, Lanes 3 and 4) or with TPA and the erbstatin analog methyl-2,5-dihydroxycinnamate (32 μM, Lanes 5 and 6) or TPA and staurosporine (30 nM, Lanes 7 and 8). The erbstatin analog or staurosporine were each added to their respective H-9 cell cultures 45 minutes prior to the addition of TPA. Negative control lanes (Lanes 1 and 2) represent H-9 cell cultures incubated overnight in the absence of TPA and either protein kinase inhibitor.

FIG. 7F shows the results of incubation of H-9 cells in the presence of 30 nM staurosporine (Lanes 7 and 8) or 32 μM methyl-2,5-dihydroxycinnamate (erbstatin analog) on the induction of MDR1 expression by TPA, a known PKC agonist. TPA alone (Lanes 3 and 4) efficiently induced readily detectable levels of MDR1 expression, consistent with the results disclosed above. Both staurosporine, a PKC inhibitor, and methyl-2,5-dihydroxycinnamate, completely inhibited TPA-induced MDR1 expression. These results are in agreement with previous observation that erbstatin analogues, which are known to inhibit epidermal growth factor tyrosine kinase, also have PKC inhibitory activity (Bishop et al., ibid.).

A number of other protein kinase inhibitors were found to have little or no capacity to inhibit Ara-C induced MDR1 expression. These compounds include D,L-threo-sphingosine (tested at 5 μM; higher concentrations induced cellular toxicity) and herbimycin A (tested at concentrations from 0.35–3 μM). No significant inhibition was observed with Iso-H7, a structural analog of H7 with 10 fold weaker effect on protein kinases (Pelosin et al., 1990, *Biochem. Biophys. Res. Commun.* 169: 1040–1048). Similar results were observed with Ara-C treated K562 cells. Another protein kinase inhibitor, genistein (150 μM) was found to only weakly inhibit Ara-C induced MDR1 expression (Table II).

These results indicated that certain among a number of protein kinase inhibitors, and particularly protein kinase C inhibitors, were capable of inhibiting MDR1 expression induced by treatment of cancer cells with cytotoxic drugs or protein kinase C agonists. The data presented herein demonstrated that different chemotherapeutic drugs, including those that are not transported by P-glycoprotein, induced MDR1 expression directly, rather than by selection of pre-existing genetic variants. Drug-induced MDR1 expression was limited to a subpopulation of treated cells and was associated with a moderate increase in the resistance of P-glycoprotein-transported drugs (approximately 2–3 fold in the case of K562 cells). This increase may be sufficient to reduce the response to chemotherapy in vivo and to enhance the selection of genetic mutants with higher levels of drug resistance. Drug-mediated induction of MDR1 expression may occur during cancer chemotherapy, and it may largely account for the increased incidence of MDR1 expression in treated tumors. Hence, the demonstration that PKC inhibitors can prevent MDR1 induction suggested using such agents in combination with cytotoxic drugs in cancer chemotherapy in order to achieve a higher degree of eradication of cancer cells.

TABLE II

Inhibition of Ara-C Induced MDR1 Expression by Protein Kinase Inhibitors

| Compound | Conc. tested | Results |
| --- | --- | --- |
| herbimycin A (12 h) | 0.3–3 μM | – |
| tyrphostin A25 (16 hr) | 50–100 μM | +++ |
| tyrphostin B46 (16 hr) | 50–100 μM | +++ |
| D,L-threo-sphingosine | 5 μM | – |
| genistein | 150 μM | + |
| staurosporine | 30 nM | +++ |
| H7 | 50 μM | +++ |
| calphostin C (+ light) | 1 μM | +++ |
| chelerythrine | 5 μM | +++ |
| methyl-1,5-dihydroxycinnamate | 32 μM | ++++ |
| neomycin sulfate | 10 mM | +++ |

MDR1 induced by incubation of H-9 cells with 25 μM Ara-C for 10 h:
++++ = complete inhibition of Ara-C mediated induction;
+ = weak inhibition of Ara-C mediated induction;
– = no inhibition of Ara-C mediated induction

EXAMPLE 5

Functional Assays of P-Glycoprotein Expression in Cells Treated with Phospholipase C Inhibitors As demonstrated in Example 4, the antibacterial agent neomycin sulfate was tested for inhibitory capacity against Ara-C induced MDR1 expression. This compound was found to inhibit MDR1 expression in cells induced with 25 μM Ara-C at concentrations of 10 mM (FIG. 7B, Lanes 7 and 8). These results demonstrate that neomycin sulfate possesses MDR1 inhibitory capacity at clinically relevant and achievable concentration. One of several known activities of neomycin sulfate is inhibition of PI-PLC (Cockroft et al., 1987, ibid.). These results suggested that other phospholipase C inhibitors could inhibit cytotoxic drug induction of MDR1 expression. Accordingly, cDNA-PCR assays were performed as described above in Example 4 on H9 human leukemia cells in which MDR1 gene expression was induced using AraC (25 $\mu$M), in the presence or absence of phospholipase C inhibitors.

H9 cells were seeded into each well of 6-well plates ($10^5$ cells/well in 3 mL of RPMI-1640 medium/10% fetal bovine serum/2 mM L-glutamine/100 U/mL penicillin and 100 $\mu$g/mL streptomycin). Experimental cultures were treated with 25 $\mu$M Ara C in the absence or in the presence of 1 $\mu$M or 10 $\mu$M U73122 (another PI-PLC inhibitor) for 10 hrs at 37° C., 5% $CO_2$ in a humidified atmosphere. The inhibitor was added 45 min. prior to the addition of Ara C. Negative control cultures were incubated as above without the addition of either AraC or U73122.

After each incubation was complete, steady-state levels of MDR1- and $\beta_2$-microglobulin mRNA (internal standard) were determined by RT-PCR as described above in Example 4. PCR products were then analyzed in 7.5% polyacrylamide gel electrophoresis and autoradiographed. The results of these experiments are shown in FIG. 8A. Lane 1 shows cDNA-PCR of MDR1 mRNA (the upper band, 167 bp) and $\beta_2$-microglobulin mRNA (the lower band, 120 bp) in H9 cells untreated with either AraC or U73122. In these cells, the band corresponding to $\beta_2$-microglobulin mRNA was detected, but no MDR1 mRNA-specific band was seen, consistent with the results on uninduced H9 cells shown above in Example 4 and FIGS. 7A through 7F. Lane 2 shows the results of cDNA-PCR analysis of H9 cells treated with 25 $\mu$M AraC; in these cells a clear MDR1-specific band was detected. Lanes 3 and 4 show the results of cDNA-PCR on H9 cell mRNA treated in the presence of 1 and 10 $\mu$M U73122, respectively. Autoradiographic analysis of the intensity of the MDR1-specific band revealed that U73122 inhibited the induction of MDR1 mRNA in these cells by AraC.

The specificity of phospholipase C-targeted inhibition of MDR1 induction by cytotoxic drugs was determined in a comparative experiment using a known inhibitor of phosphocholine-dependent phospholipase C (PC-PLC). This compound, tricyclodecan-9-yl-xanthogenate potassium (D609) was found to be incapable of inhibiting AraC-induced expression of MDR1 even at concentrations (100 $\mu$g/mL) known to be sufficient to inhibit PC-PLC.

These results indicated that certain among a number of phospholipase C inhibitors, and specifically phosphoinositol-dependent PLC inhibitors, were capable of inhibiting MDR1 expression induced by treatment of cancer cells with cytotoxic drugs. This demonstration that PI-PLC inhibitors can prevent MDR1 induction suggested using such agents in combination with cytotoxic drugs in cancer chemotherapy in order to prevent development of MDR1-mediated drug resistance.

EXAMPLE 6

Functional Assays of P-Glycoprotein Expression in Cells Treated with Cytoplasmic Calcium Antagonists and Calmodulin Inhibitors In view of the results disclosed above, other intracellular components of eukaryotic signal transduction pathways were examined as targets of MDR1 gene induction by cytotoxic drugs. In this regard, agents which increased intracellular $Ca^{2+}$ ion concentration were assayed for the ability to induce MDR1 gene expression.

H9 cells were seeded into each well of 6-well plates ($10^5$ cells/well in 3 mL of RPMI-1640 medium/10% fetal bovine serum/2 mM L-glutamine/100 U/mL penicillin and 100 $\mu$g/mL streptomycin). Experimental cultures were treated with either the calcium-specific ionophore A23187 or an inhibitor of $Ca^{2+}$-dependent ATPase, thapsigargin. Cells were incubated with 10 $\mu$M A23187 or 10 $\mu$g/mL thapsigargin for 10 hrs at 37° C., 5% $CO_2$ in a humidified atmosphere. Negative control cultures were incubated as above without the addition of either A23187 or thapsigargin.

After each incubation was complete, steady-state levels of MDR1- and $\beta_2$-microglobulin mRNA (internal standard) were determined by RT-PCR as described above in Example 4. PCR products were then analyzed in 7.5% polyacrylamide gel electrophoresis and autoradiographed. The results of these experiments are shown in FIG. 8B. Lane 1 shows cDNA-PCR bands specific for MDR1 mRNA and $\beta_2$-microglobulin mRNA as above in Example 5 in untreated H9 cells. The absence of the MDR1-specific band and presence of the $\beta_2$-microglobulin specific band was consistent with the results on uninduced H9 cells shown above in Examples 4 and 5 and FIGS. 7A through 7F. Lane 2 shows the results of a similar cDNA-PCR analysis of H9 cells treated with 10 $\mu$M A23187, and Lane 3 shows the cDNA-PCR results from H9 cells treated with 10 $\mu$g/mL thapsigargin. In these cells a clear MDR1-specific band was detected, indicating that an increase in intracellular levels of calcium, an event associated with signal transduction mechanisms in eukaryotic cells, was capable of inducing MDR1 gene expression, which capacity had been discovered for treatment of H9 cells with both cytotoxic drugs and PKC agonists (see Examples 3 and 4, above).

In view of these results, cytoplasmic calcium antagonists and calmodulin inhibitors were tested for the ability to inhibit induction of MDR1 gene expression by a variety of cytotoxic drugs. H9 cells were incubated as described above in the presence of the following cytotoxic drugs: Ara C (at a concentration of 25 $\mu$M), Adriamycin (2 $\mu$M), bleomycin (100 $\mu$g/ml), 2-deoxyglucose (10 mM) and nocodazole (2.5 $\mu$M). In parallel, cultures of H9 cells were incubated in the presence of each of these cytotoxic drugs and of a highly specific chelator of intracellular calcium ion, 1, 2-bis(o-aminophenoxy)-ethane-N,N,N',N'-tetraacetic acid, tetra (acetoxymethyl)-ester (BAPTA/AM) at a concentration of 5 $\mu$M for 10 hrs. under the conditions described above. The inhibitor was added 45 min. prior to the addition of each of the MDR1 inducing agents. cDNA-PCR analysis, including gel electrophoresis and autoradiography as described above, was performed for each culture after drug treatment in the presence or absence of this chelator. The results of these experiments are shown in FIG. 8C.

Each lane in FIG. 8C is labeled to indicate the identity of the cytotoxic drug and the presence (+) or absence (−) of BAPTA/AM in the incubation media. These results demonstrate that pretreatment of H9 cells with 5 $\mu$M BAPTA/AM completely abrogated the induction of MDR1 expression by different cytotoxic agents. This inhibitory effect of BAPTA/AM was detectable when the chelator was given to the cells within first 3 hrs. prior to the addition of MDR1 inducers.

In another series of experiments, an inhibitor of intracellular release of calcium ions from cytoplasmic stores, 8-(dimethylamino)octyl-3,4,5-trimethoxybenzoate hydrochloride (TMB-8), was tested as described above and found to completely abrogate the ability of AraC to induce MDR1 gene expression in H9 cells when present at a concentration of 200 $\mu$M.

Figure 8D:
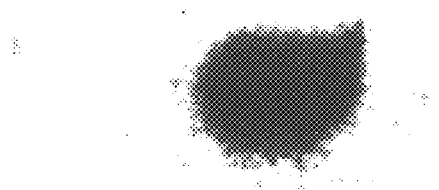
FIG. 8D. Effects of calmodulin inhibitor on MDR1 induction by AraC. H9 cells were either untreated (lane 1) or treated with 25 μM Ara C alone (lane 2) or treated with Ara C for 10 hrs in the presence of 10 μM calmidazolium chloride given 45 min. prior to Ara C (lane 3). Levels of MDR1 mRNA were determined by quantitative RT-PCR.
Figure 8D:
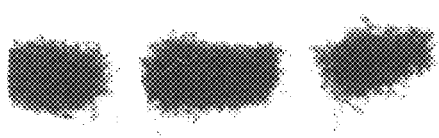

Having demonstrated that BAPTA/AM and TMB-8 could inhibit cytotoxic drug induction of MDR1 gene expression, an inhibitor of a major mediator of the calcium-dependent signal transduction mechanism, calmodulin, was assayed. H9 cells were incubated as above with 25 µM AraC in the presence or absence of 10 µM calmidazolium chloride, and cDNA-PCR analysis as described above was performed. The results of these experiments are shown in FIG. 8D. Calmidazolium chloride was found to efficiently abrogate AraC induction of MDR1 expression under the conditions of this assay. These results, taken with the results of BAPTA/AM inhibition disclosed above, indicate that inhibition of intracellular calcium ion release prevents induction of MDR1.

This demonstration of the role of cytoplasmic calcium ion concentration and calcium-dependent signal transduction on induction of MDR1 gene expression suggested that such agents can be used in combination with cytotoxic drugs in cancer chemotherapy in order to prevent development of MDR1-mediated drug resistance.

EXAMPLE 7

Functional Assays of P-Glycoprotein Expression in Cells Treated with Inhibitors of Transcription Factor NF-κB Activation In view of the efficient induction of MDR1 gene expression by AraC, cellular responses to AraC treatment were investigated as targets, the inhibition of which could abrogate MDR1 induction by AraC. Recently it has been reported that treatment of cells with Ara C results in the release of NF-κB from the inhibitory subunit followed by translocation of the active NF-κB to the nucleus (see Siebenlist et al. and Kopp et al., ibid.) This suggested that agents which inhibit the activation of NF-κB (for example, as the result of stress stimuli) would also be able to prevent induction of MDR1 by chemotherapeutic drugs.

Figure 8E:
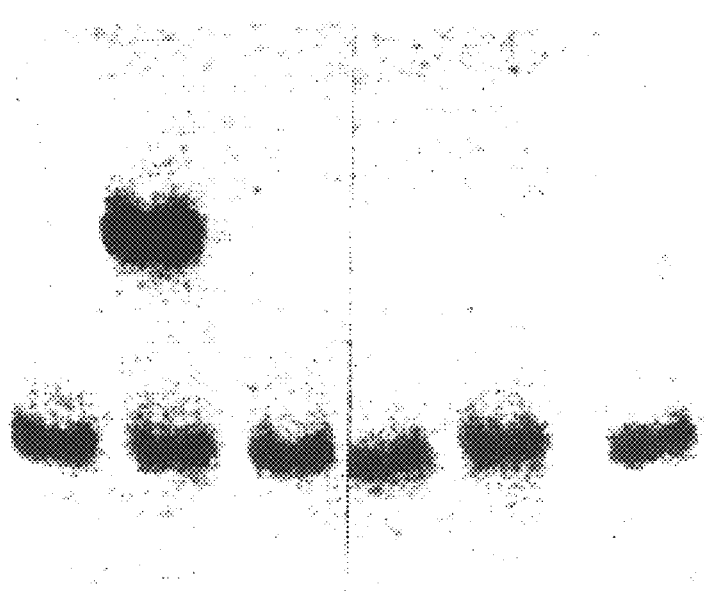
FIG. 8E. Effects of inhibitors of NF-κB activation on MDR1 induction by Ara C. H9 cells were untreated (lane 1) or treated with 25 μM Ara C for 10 hours (lanes 2–6) in the absence (lane 2) or in the presence of 20 μM pyrrolidone dithiocarbamate (lane 3), 25 μM N-tosyl-L-phenylalanine chloromethyl ketone (lane 4), 20 mM sodium salicylate (lane 5) or 10 mM aspirin (lane 6). All inhibitors were given 45 min. prior to Ara C. Quantitative RT-PCR was performed for the analysis of the levels of MDR 1 mRNA.

Accordingly, MDR1 gene expression was induced as above in 9 cells with AraC for 10 hrs. in the presence or absence of 20 µM pyrrolidone dithiocarbamate, 25 µM N-tosyl-L-phenylalanine chloromethyl ketone, 20 µM sodium salicylate or 10 mM acetylsalicylic acid (aspirin). All inhibitors were given 45 min. prior to Ara C treatment. cDNA-PCR analysis was performed as described above, and the results of these experiments shown in FIG. 8E.

Each of the inhibitors tested completely abrogated the induction of MDR1 gene expression by 25 µM AraC. Untreated H9 cells showed the expected pattern of β2-microglobulin expression without detectable MDR1 expression (lane 1), and AraC treated cells showed expression of both genes (lane 2). H9 cells pretreated with 20 µM pyrrolidone dithiocarbamate (lane 3), 25 µM N-tosyl-L-phenylalanine chloromethyl ketone (lane 4), 20 mM sodium salicylate (lane 5) or 10 mM aspirin (lane 6) all showed complete suppression of AraC-induced MDR1 expression.

Figure 8F:
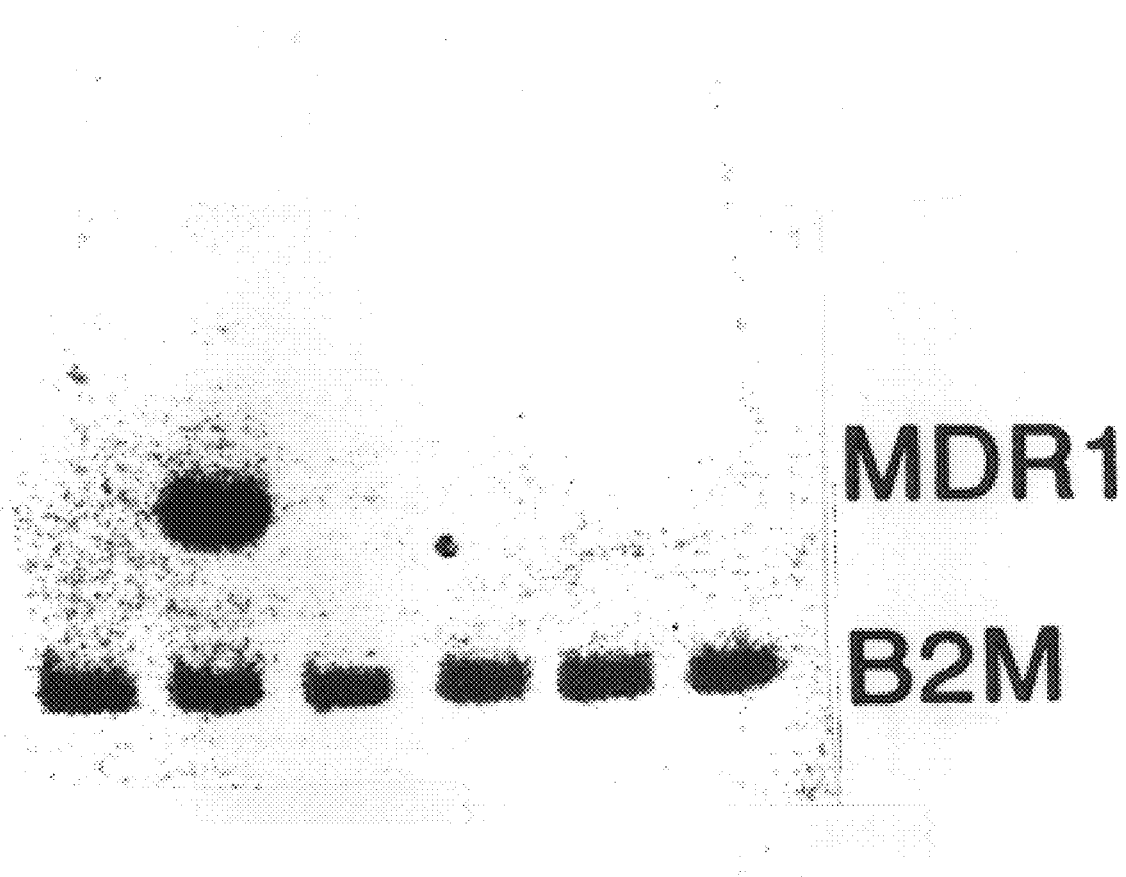
FIG. 8F. Effects of inhibitors of NF-κB activation on MDR1 induction by Adriamycin. H9 cells were treated under the same conditions as in FIG. 8E using Adriamycin (2 μM) instead of Ara C.

This experiment was repeated using 2 µM Adriamycin instead of Ara C to induce MDR1 expression As shown in FIG. 8F, essentially the same results obtained using AraC were obtained for each of the inhibitors tested when MDR1 expression was induced by Adriamycin.

These results indicated that certain inhibitors of NF-κB activation, including aspirin, were capable of inhibiting MDR1 expression induced by treatment of cancer cells with cytotoxic drugs. These data suggested using such agents in combination with cytotoxic drugs in cancer chemotherapy in order to prevent development of MDR1-mediated drug resistance. Sodium salicylate and aspirin are already in clinical use, for the attenuation of inflammatory symptoms in patient with infectious and autoimmune diseases and for a broad spectrum of more recently-appreciated therapeutical properties (see Marnett, 1992, Cancer Res. 52: 5575–5589; Anderson et al., 1993, Cancer Res. 53: 806–809; Rao et al., 1995, Cancer Res. 55: 1464–1472). The use of such compounds in combination with administration of cancer chemotherapeutic drugs provides the capacity to increase the clinical efficacy of current antineoplastic treatment protocols.

EXAMPLE 8

Protein Kinase Inhibitors Prevent MRP Expression in Tumor Cells

1. Materials and Methods 1.1 MRP Expression Inhibition Assays

Cells were plated in 6-well Falcon tissue culture plates at 3,300 cells per well, and incubated in the appropriate concentrations of drugs. Each of the protein kinase inhibitors to be tested were added at their appropriate final concentrations, and the cells then incubated for 10 hours at 37° C. under an atmosphere of 5% $CO_2$.

cDNA-PCR analyses on each culture treated with drugs, or in control cultures incubated without drugs, were performed as described in Example 1 above. PCR was performed using the following primers:

```
β₂M (sense)       5'-ACCCCCACTGAAAAAGATGA-3'    (SEQ ID No.: 1)

β₂M (antisense)   5'-ATCTTCAAACCTCCATGATG-3'    (SEQ ID No.: 2)

MRP (sense)       5'-GGACCTGGACTTCGTTCTCA-3'    (SEQ ID No.: 5)

MRP (antisense)   5'-CGTCCAGACTTCCTTCATCCG-3'   (SEQ ID No.: 6)
```

(where $β_2M$ represents $β_2$microglobulin). PCR was performed for $β_2M$ experiments under a regime consisting of 1 cycle comprising denaturation at 94° C. for 3 minutes, primer annealing at 60° C. for 30 seconds, and primer extension at 72° C. for 1 minute, followed by 19 cycles comprising denaturation at 94° C. for 30 seconds, primer annealing at 60° C. for 30 seconds, and primer extension at 72° C. for 1 minute, followed by a final cycle comprising denaturation at 94° C. for 30 seconds, primer annealing at 60° C. for 30 seconds, and primer extension at 72° C. for 5 minutes. MRP cDNA sequences were amplified using a protocol consisting of 1 cycle comprising denaturation at 94° C. for 3 minutes, 26 cycles of denaturation at 94° C. for 30 seconds, primer annealing at 62° C. for 30 seconds, and primer extension at 72° C. for 1 minute, followed by 1 cycle comprising primer extension at 72° C. for 5 minutes, resulting in an MRP-specific amplified fragment of 292 bp. $^{32}$P-labeled PCR products were detected by autoradiography.

EXAMPLE 9

Figure 9A:
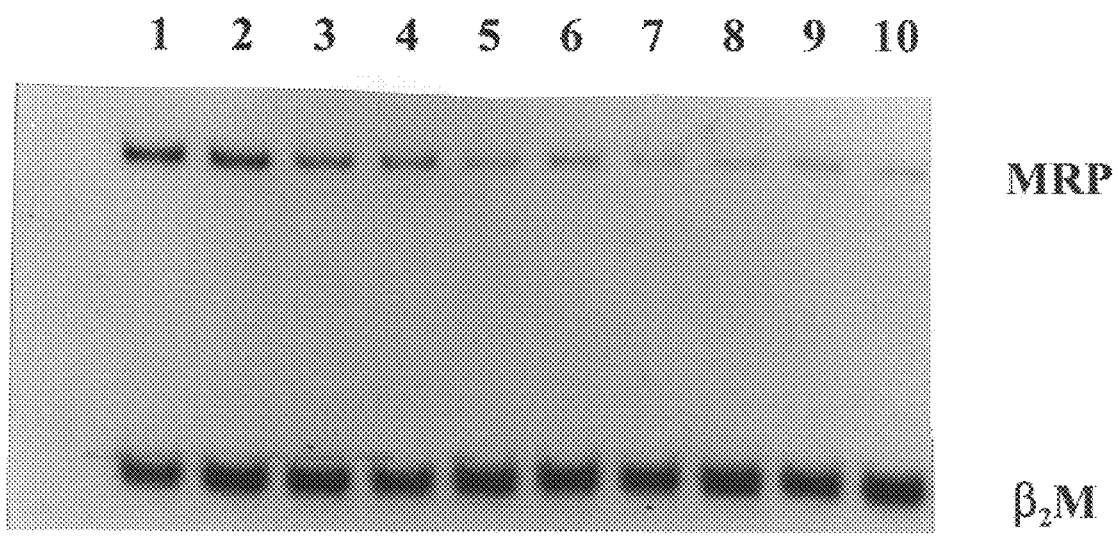
FIG. 9A. MRP mRNA expression inhibition in drug-treated H-9 cells. Cells were incubated for 10 hours with 30 nM staurosporine (Lanes 3 and 4), 5 μM chelerythrine (Lanes 5 and 6), 32 μM methyl-2,5-dihydroxycinnamate (erbstatin analog; Lanes 7 and 8) or 10 mM neomycin sulfate (Lanes 9 and 10). Negative control lanes (Lanes 1 and 2) represent H-9 cell cultures incubated overnight in the absence of any drug.

Functional Assays of MRP Expression in Cells Treated with Protein Kinase Activators and Inhibitors H-9 cells were used to analyze the effect of various protein kinase inhibitors on the expression of the multidrug resistance associated protein MRP (Grant et al., ibid.). The results of these experiments are shown in FIGS. 9A. When MRP mRNA expression was evaluated in H-9 cells in the absence of any drugs, these cells were found to express the MRP gene robustly (FIGS. 9A, Lanes 1 and 2). In contrast to MDR1, incubation of H-9 cells in 25 $\mu$M Ara-C resulted in a slight decrease in MRP expression (data not shown). Following incubation with staurosporine (100 nM; Lanes 3 and 4), chelerythrine (1–5 $\mu$M; Lanes 5 and 6); methyl-2,5-dihydroxycinnamate (32 $\mu$M; Lanes 7 and 8) or neomycin sulfate (10 mM; Lanes 9 and 10), MRP expression was strongly inhibited.

These results demonstrate that a variety of protein kinase inhibitory compounds have the capacity to inhibit both cytotoxic drug-induced MDR1 expression and expression of the multidrug resistance phenotype-related MRP gene. These results strongly suggest that such protein kinase inhibitors have great utility in preventing the emergence of multidrug resistance in cancer patients receiving chemotherapeutic treatment.

TABLE III

Inhibition of MRP Expression by Protein Kinase Inhibitors

| Compound | Conc. tested | Results |
|---|---|---|
| staurosporine | 100 nM | ++++ |
| chelerythrine | 1–5 $\mu$M | ++++ |
| methyl-l,5-dihydroxycinnamate | 32 $\mu$M | ++++ |
| neomycin sulfate | 10 mM | ++++ |

++++ = complete inhibition of MRP expression

The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method of inhibiting MDR1 induction in a cancer cell by treatment with a cytotoxic drug, comprising contacting the cell with a phosphoinositol-dependent phospholipase C inhibitor coincident with treatment with the cytotoxic drug.

2. The method according to claim 1, wherein the phosphoinositol-dependent phospholipase C inhibitor is neomycin sulfate, 1-(6-((17β-3-methoxyestra-1,3,5(10)-trien-17-yl)amino)hexyl)-1-H-pyrrole-2,5-dione, or phospholipase C-inhibiting analogues thereof.

3. The method according to claim 1, wherein the cytotoxic drug is a chemotherapeutic drug.

4. The method of claim 1 wherein the cancer cells contain little or no detectable MDR1-encoded P-glycoprotein, as determined by immunoreactivity with anti-P-glycoprotein antibodies, accumulation or efflux of P-glycoprotein transported dyes, or MDR1 mRNA expression assay.

5. The method of claim 1 in which the cancer cells are derived from hematopoietic tumors.

6. The method of claim 1 in which the cancer cells are derived from solid tumors.

7. A method of inhibiting MDR1 induction in a cancer cell by treatment with a cytotoxic drug, comprising contacting the cell with an cytoplasmic calcium antagonist or calmodulin inhibitor, coincident with treatment with the cytotoxic drug.

8. The method according to claim 7, wherein the cytoplasmic calcium antagonist is 1,2-bis(o-aminophenoxy)-ethane-N,N,N',N'-tetraacetic acid, tetra(acetoxymethyl)-ester, 8-(dimethylamino)octyl-3,4,5-trimethoxybenzoate hydrochloride, or analogues thereof that are cytoplasmic calcium ion antagonists.

9. The method according to claim 7, wherein the calmodulin inhibitor is 1-{6-{{17β-3-methoxyestra-1,3,5(10)-trien-17-yl}amino}hexyl}-1-H-pyrrole-2,3-dione, or calmodulin-inhibiting analogues thereof.

10. The method according to claim 7, wherein the cytotoxic drug is a chemotherapeutic drug.

11. The method of claim 7 wherein the cancer cells contain little or no detectable MDR1-encoded P-glycoprotein, as determined by immunoreactivity with anti-P-glycoprotein antibodies, accumulation or efflux of P-glycoprotein transported dyes, or MDR1 mRNA expression assay.

12. The method of claim 7 in which the cancer cells are derived from hematopoietic tumors.

13. The method of claim 7 in which the cancer cells are derived from solid tumors.

14. A method of inhibiting MDR1 induction in a cancer cell by treatment with a cytotoxic drug, comprising contacting the cell with an inhibitor of activation of eukaryotic transcription factor NF-κB, coincident with treatment with the cytotoxic drug.

15. The method according to claim 14, wherein the inhibitor of activation of eukaryotic transcription factor NF-κB is pyrrolidone dithiocarbamate, N-tosyl-L-phenylalanine chloromethyl ketone, sodium salicylate or acetysalicylic acid, or analogues thereof that inhibit activation of eukaryotic transcription factor NF-κB.

16. The method according to claim 14, wherein the cytotoxic drug is a chemotherapeutic drug.

17. The method of claim 14 wherein the cancer cells contain little or no detectable MDR1-encoded P-glycoprotein, as determined by immunoreactivity with anti-P-glycoprotein antibodies, accumulation or efflux of P-glycoprotein transported dyes, or MDR1 mRNA expression assay.

18. The method of claim 14 in which the cancer cells are derived from hematopoietic tumors.

19. The method of claim 14 in which the cancer cells are derived from solid tumors.

20. A pharmaceutical composition comprising therapeutically-effective amount of a phosphoinositol-dependent phospholipase C inhibitor and a pharmaceutically-acceptable carrier.

21. A pharmaceutical composition comprising therapeutically-effective amount of an cytoplasmic calcium antagonist or calmodulin inhibitor, and a pharmaceutically-acceptable carrier.

22. A pharmaceutical composition comprising therapeutically-effective amount of an inhibitor of activation of eukaryotic transcription factor NF-κB, and a pharmaceutically-acceptable carrier.

23. The pharmaceutical composition of claim 20 also comprising a chemotherapeutic drug.

24. The pharmaceutical composition of claim 21 also comprising a chemotherapeutic drug.

25. The pharmaceutical composition of claim 22 also comprising a chemotherapeutic drug.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

ACCCCCACTG AAAAAGATGA      20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

ATCTTCAAAC CTCCATGATG      20

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

```
           (xi) SEQUENCE DESCRIPTION: SEQ ID NO:3:

CCCATCATTG CAATAGCAGG                                                      20

(2) INFORMATION FOR SEQ ID NO:4:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:4:

GTTCAAACTT CTGCTCCTGA                                                      20

(2) INFORMATION FOR SEQ ID NO:5:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:5:

GGACCTGGAC TTCGTTCTCA                                                      20

(2) INFORMATION FOR SEQ ID NO:6:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:6:

CGTCCAGACT TCCTTCATCC G                                                    21
```